US010413589B2

(12) United States Patent
Bandala Sanchez et al.

(10) Patent No.: US 10,413,589 B2
(45) Date of Patent: Sep. 17, 2019

(54) SOLUBLE MEDIATOR

(71) Applicant: The Walter and Eliza Hall Institute of Medical Research, Melbourne, Victoria (AU)

(72) Inventors: Esther Bandala Sanchez, Melbourne (AU); James Dromey, Melbourne (AU); Leonard Charles Harrison, Melbourne (AU); Yuxia Zhang, Melbourne (AU)

(73) Assignee: The Walter and Eliza Hall Institute of Medical Research, Parkville (AU)

( * ) Notice: Subject to any disclaimer, the term of this patent is extended or adjusted under 35 U.S.C. 154(b) by 0 days.

(21) Appl. No.: 16/218,287

(22) Filed: Dec. 12, 2018

(65) Prior Publication Data

US 2019/0192624 A1 Jun. 27, 2019

Related U.S. Application Data

(60) Continuation of application No. 15/975,591, filed on May 9, 2018, which is a division of application No. 15/384,137, filed on Dec. 19, 2016, now Pat. No. 10,010,582, which is a continuation of application No. 14/351,501, filed as application No. PCT/AU2012/001411 on Nov. 15, 2012, now Pat. No. 9,585,969.

(60) Provisional application No. 61/705,633, filed on Sep. 26, 2012, provisional application No. 61/560,254, filed on Nov. 15, 2011.

(51) Int. Cl.
| A61K 38/17 | (2006.01) |
| C07K 14/705 | (2006.01) |
| A61K 38/10 | (2006.01) |
| C12N 5/0783 | (2010.01) |
| G01N 33/50 | (2006.01) |
| C12Q 1/6883 | (2018.01) |
| C07K 16/18 | (2006.01) |
| A61K 47/68 | (2017.01) |
| G01N 33/68 | (2006.01) |
| A61K 48/00 | (2006.01) |

(52) U.S. Cl.
CPC ............ A61K 38/177 (2013.01); A61K 47/68 (2017.08); C07K 14/70592 (2013.01); C07K 16/18 (2013.01); C12N 5/0637 (2013.01); C12Q 1/6883 (2013.01); G01N 33/505 (2013.01); G01N 33/6872 (2013.01); A61K 38/10 (2013.01); A61K 48/00 (2013.01); C07K 2319/30 (2013.01)

(58) Field of Classification Search
CPC .................. A61K 38/177; A61K 38/10; C07K 14/70592; C07K 2319/30; C12N 5/0637
See application file for complete search history.

(56) References Cited

U.S. PATENT DOCUMENTS

| 9,585,969 B2 * | 3/2017 | Bandala Sanchez ........................ C07K 14/70592 |
| 10,010,582 B2 * | 7/2018 | Bandala Sanchez ........................ C07K 14/70592 |
| 2007/0286857 A1 * | 12/2007 | Arthaud ............ C07K 16/2893 424/133.1 |

FOREIGN PATENT DOCUMENTS

| WO | WO 2002/030460 | 4/2002 |
| WO | WO 2003/024993 | 3/2003 |
| WO | WO 2005/036123 | 4/2005 |
| WO | WO 2008/028229 | 3/2008 |
| WO | WO 2009/148568 | 12/2009 |
| WO | WO 2011/109662 | 9/2011 |

OTHER PUBLICATIONS

Turner et al., Reduction of inflammation and preservation of neurological function by anti-CD52 therapy in murine experimental autoimmune encephalomyelitis. Journal of neuroimmunology, 285:4-12, 2015.*
Albitar et al. (2004) "Free Circulating Soluble CD52 as a Tumer Marker in Chronic Lymphocytic Leukemia and Its Implication in Therapy with Anti-CD52 Antibodies," *Cancer*, 101:999-1008.
Allan et al. (2007) "Activation-induced FOXP3 in human T effector cells does not suppress proliferation or cytokine production," *Int. Immunol.* 19: 345-354.
Altschul et al. (1993) "Basic Local Alignment Search Tool," *J. Mol. Biol.* 215: 403410.
Armour (2003) "Differential binding to human FcγRIIa and FcγRIIa receptors by human IgG wildtype and mutant antibodies," *Mol. Immunol.* 40: 585-93.
Bach et al (1997) "High Affinity Presentation of an Autoantigenic Peptide in Type I Diabetes by an HLA Class II Protein Encoded in a Haplotype Protecting From Disease," *J Autoimmun* 10:375-386.
Bandala-Sanchez et al (2013) "T cell regulation mediated by interaction of soluble CD52 with the inhibitory receptor Siglec-10," *Nature Immunol.* 14: 741-748.

(Continued)

*Primary Examiner* — Ruixiang Li
(74) *Attorney, Agent, or Firm* — Shweta Chandra; Bozicevic, Field & Francis LLP

(57) ABSTRACT

The present disclosure relates to a soluble CD52 glycoprotein and its use in treating diseases regulated by effector T-cells, for example autoimmune diseases such as type I diabetes. The present disclosure also relates to fusion proteins comprising the soluble glycoprotein, to cells expressing high levels of CD52, and to diagnostic methods based on the detection of CD52 expression levels in a subject.

13 Claims, 28 Drawing Sheets

Figure 1:
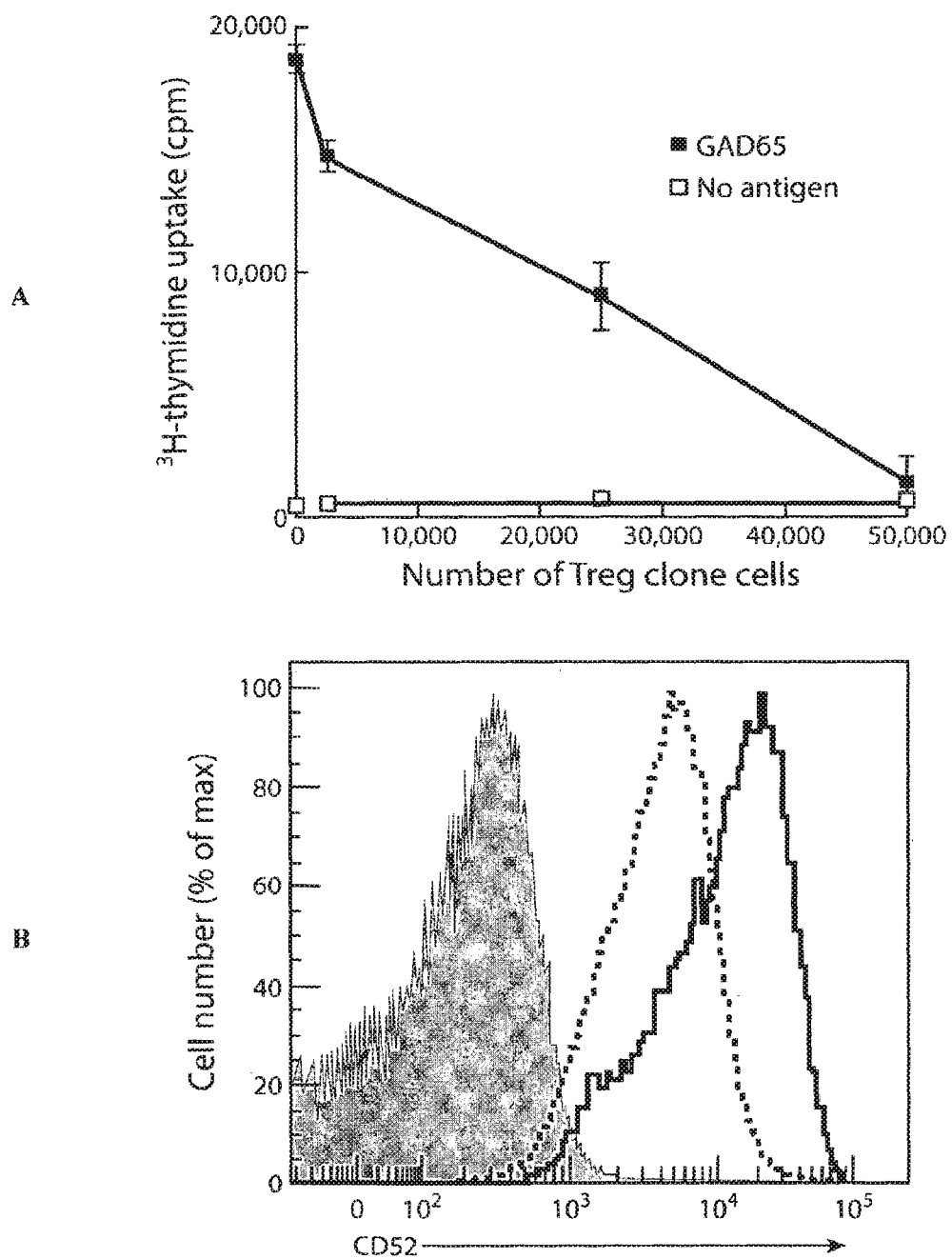

Specification includes a Sequence Listing.

(56) References Cited

OTHER PUBLICATIONS

Barnden et al. (1998) "Defective TCR expression in transgenic mice constructed using cDNA-based α- and β-chain genes under the control of heterologous regulatory elements," *Immunol. Cell Biol.* 76: 34.
Belov et al. (2003) "Identification of repertoires of surface antigens on leukemias using an antibody microarray," *Proteomics* 3: 2147-2154.
Bergerot et al. (1994) "Oral Administration of Human Insulin to NOD Mice Generates CD4 T Cells that Suppress Adoptive Transfer of Diabetes," *J. Autoimmun.* 7: 655-663.
Collison et al. (2007) "The inhibitory cytokine IL-35 contributes to regulatory T-cell function," *Nature* 450: 566-569.
Crocker et al. (2007) "Siglecs and their roles in the immune system," *Nat. Rev. Immunol.* 7: 255-266.
Dromey et al. (2011) "Generation and expansion of regulatory human CD4ϕ T-cell clones specific for pancreatic islet autoantigens," *J. Autoimmunity* 36: 47-55.
Every et al. (2006) "Intranasal Vaccination with Proinsulin DNA Induces Regulatory CD4 + T Cells That Prevent Experimental Autoimmune Diabetes," *J. Immunol.* 176: 4608-4615.
Fontenot et al. (2003) "Foxp3 programs the development and function of CD4+CD25+ regulatory T cells," *Nat. Immunol.* 4: 330-336.
Gavin et al. (2006) "Single-cell analysis of normal and FOXP3-mutant human T cells: FOXP3 expression without regulatory T cell development," *Proc. Natl. Acad. Sci. U.S.A.* 103: 6659-6664.
Hale (2001) "CD52 (CAMPATH-1)" *J. Biol. Regul. Homeost. Agents* 15: 386-91.
Harayama (1998) "Artificial evolution by DNA Shuffling," *Trends Biotechnol.* 16: 76-82.
Hearnden et al. (2012) "New developments and opportunities in oral mucosal drug delivery for local and systemic disease," *Ad. Drug Deliver. Rev.* 64:16-28.
Herold et al. (2008) "Inducible and reversible gene silencing by stable integration of an shRNA-encoding lentivirus in transgenic rats," *Proc. Natl. Acad. Sci. U.S.A.* 105: 18507-18512.
Higgins and Sharp (1989) "Fast and sensitive multiple sequence alignments on a microcomputer," *CABIOS.* 5: 151-153.
Hogquist et al. (1993) "Positive Selection of CD8 + T Cells Induced by Major Histocompatibility Complex Binding Peptides in Fetal Thymic Organ Culture," *J. Exp. Med.* 177: 1469.
Hori et al. (2003) "Control of Regulatory T Cell Development by the Transcription Factor Foxp3," *Science* 299: 1057-1061.
Hu et al. (2009) "Silencing of genes required for glycosylphosphatidylinositol anchor biosynthesis in Burkitt lymphoma," *Exp. Hematol.* 237: 423-434.
Kirchhoff et al., (2001) "New Insights into the Origin, Structure and Role of CD52: a Major Component of the Mammalian Sperm Glycocalyx," *Cells Tissues Organs*, 168:93-104.
Lapalombella et al (2008) "A Novel Raji-Burkitt's LymphomaModel for Preclinical and Mechanistic Evaluation of CD52-Targeted Immunotherapeutic Agents," *Clin Cancer Res* 14: 569-578.
Lee (2001) "Mucosal Drug Delivery," *J. Natl. Inst. Monogr.* (2001) 29: 41-44.
Lernmark (2001) "Autoimmune diseases: are markers ready for prediction?" *J Clin Invest* 108:1091-1096.
Liu et al. (2006) "CD 127 expression inversely correlates with FoxP3 and suppressive function of human CD4""T reg cells," *J Exp Med* 203: 1701-1711.
Mannering et al. (2003) "A sensitive method for detecting proliferation of rare autoantigen-specific human T cells," *J. Immunol. Meth.* 283:173-83.
Mittag et al. (2011) "Human Dendritic Cell Subsets from Spleen and Blood Are Similar in Phenotype and Function but Modified by Donor Health Status," *J. Immunol.* 186: 6207-17.

Miyara et al. (2009) "Functional Delineation and Differentiation Dynamics of Human CD4+ T Cells Expressing the FoxP3 Transcription Factor," *Immunity* 30: 899-911.
Munday et al. (2001) "Identification, characterization and leucocyte expression of Siglec-10, a novel human sialic acid-binding receptor," *Biochem. J.* 355: 489-497.
Ngyuen et al. (2006) "Loss of Siglec expression on T lymphocytes during human evolution," *Proc. Natl. Acad. Sci.* 103: 7765-7770.
Roncarolo and Gregori (2008) "The validity of Foxp3 to define human and mouse regulatory T cells," *Eur. J. Immunol.* 38: 925-927.
Sakaguchi et al. (2008) "Regulatory T Cells and Immune Tolerance," *Cell* 133: 775-787.
Sakaguchi et al. (2009) "Regulatory T cells: how do they suppress immune responses?" *Int. Immunol.* 21: 1105-1111.
Samten (2013) "CD52 as both a marker and an effector molecule of T cells with regulatory action: Identification of novel regulatory T cells," *Cellular and Immunology* 10: 456-458.
Schmidt and Skerra (2007) "The Strep-tag system for one-step purification and high-affinity detection or capturing of proteins," *Nat. Protoc.* 2: 1528-35.
Schröter et al (1999) "Male-specific Modification of Human CD52*," *J. Biol. Chem.* 274: 29862-29873.
Seddiki et al. (2006) "Expression of interleukin (IL)-2 and IL-7 receptors discriminates between human regulatory and activated T cells," *J. Exp. Med.* 203: 1693-1700.
Shao et al. (2003) "Chemical Synthesis of CD52 Glycopeptides Containing the Acid-Labile Fucosyl Linkage," *Journal of Organic Chemistry*, 68:9003-9011.
Shevach (2006) "From Vanilla to 28 Flavors: Multiple Varieties of T Regulatory Cells," *Immunity* 25: 195-201.
Shevach (2009) "Mechanisms of Foxp3+ T Regulatory Cell-Mediated Suppression," *Immunity* 30: 636-645.
Song et al. (2004) "Mucosal Drug Delivery: Membranes, Methodologies, and Applications," *Crit. Rev. Ther. Drug Carrier Syst.* 21:195-256.
Swarts et al. (2008) "Synthesis and CD structural studies of CD52 peptides and glycopeptides," *Carbohydrate Research*, 343:2894-2902.
Tang et al. (2004) "In Vitro—expanded Antigen-specific Regulatory T Cells Suppress Autoimmune Diabetes," *J. Exp. Med.* 199: 1455-1465.
Tisch et al. (1999) "Induction of Glutamic Acid Decarboxylase 65-Specific Th2 Cells and Suppression of Autoimmune Diabetes at Late Stages of Disease Is Epitope Dependent," *J. Immunol.* 163: 1178-1187.
Tone et al. (1999) "Structure and chromosomal location of mouse and human CD52 genes," *Biochim. Biophys. Acta.* 1446: 334-340.
Treumann et al. (1995) "Primary Structure of CD52," *J. Biol. Chem.* 270: 6088-6099.
Vignali et al. (2008) "How regulatory T cells work," *Nat. Rev. Immunol.* 8: 523-532.
Von Herrath and Harrison (2003) "Antigen-Induced Regulatory T Cells in Autoimmunity," *Nat. Rev. Immunol.* 3: 223-232.
Xia et al. (1991) "Characterization of the CAMPATH-1 (CDw52) antigen: biochemical analysis and cDNA cloning reveal an unusually small peptide backbone," *Eur. J. Immunol.* 21: 1677-1684.
Costelloe, Lisa, et al., (2012) "Secondary autoimmune diseases following alemtuzumab therapy for multiple sclerosis", Expert Rev. Neurother. 12(3):335-341.
Dinarello, Charles A., (2007) "Historical insights into cytokines", Eur. J. Immunol., 37:S34-45.
Ditzel, HJ, (2004) "The K/BxN mouse: a model of human inflammatory arthritis", Trends Mol Med, 10: 40-45.
Dominguez-Villar, Margarita, and Hafler, David A., (2018) "Regulatory T cells in autoimmune disease" Nat Immunol, 19:665-673.
Lawlor, KE, et al., (2015) "RIPK3 promotes cell death and NLRP3 inflammasome activation in the absence of MLKL", Nat Commun, 6:6282-86.
Ruck, Tobia, et al., (2015) "Alemtuzumab in Multiple Sclerosis: Mechanism of Action and Beyond", Int. J. Mol. Sci., 16:16414-16439.

\* cited by examiner

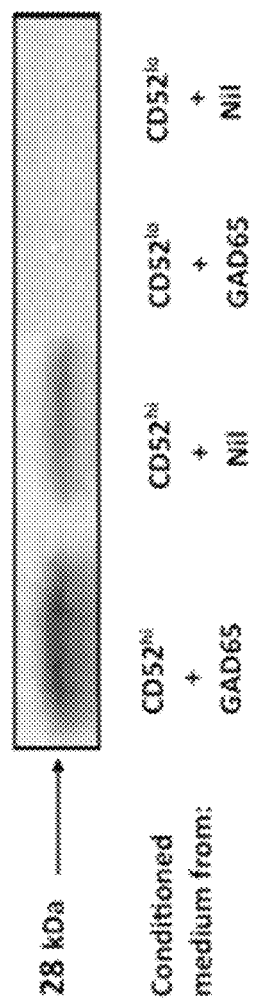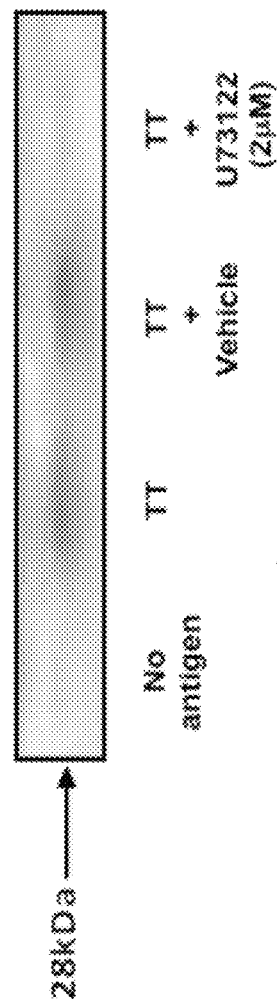
Figure 8A
Figure 8B insulitis score of male NOD mice injected with
CD3+ T cells or CD52lo CD3+ T cells after 4 weeks The insulitis score was determined as follows:
0= no infiltration,
1= peri-ductal infiltrate,
2= peri-islet infiltrate,
3= intra-islet infiltrate,
4= beta cell destruction

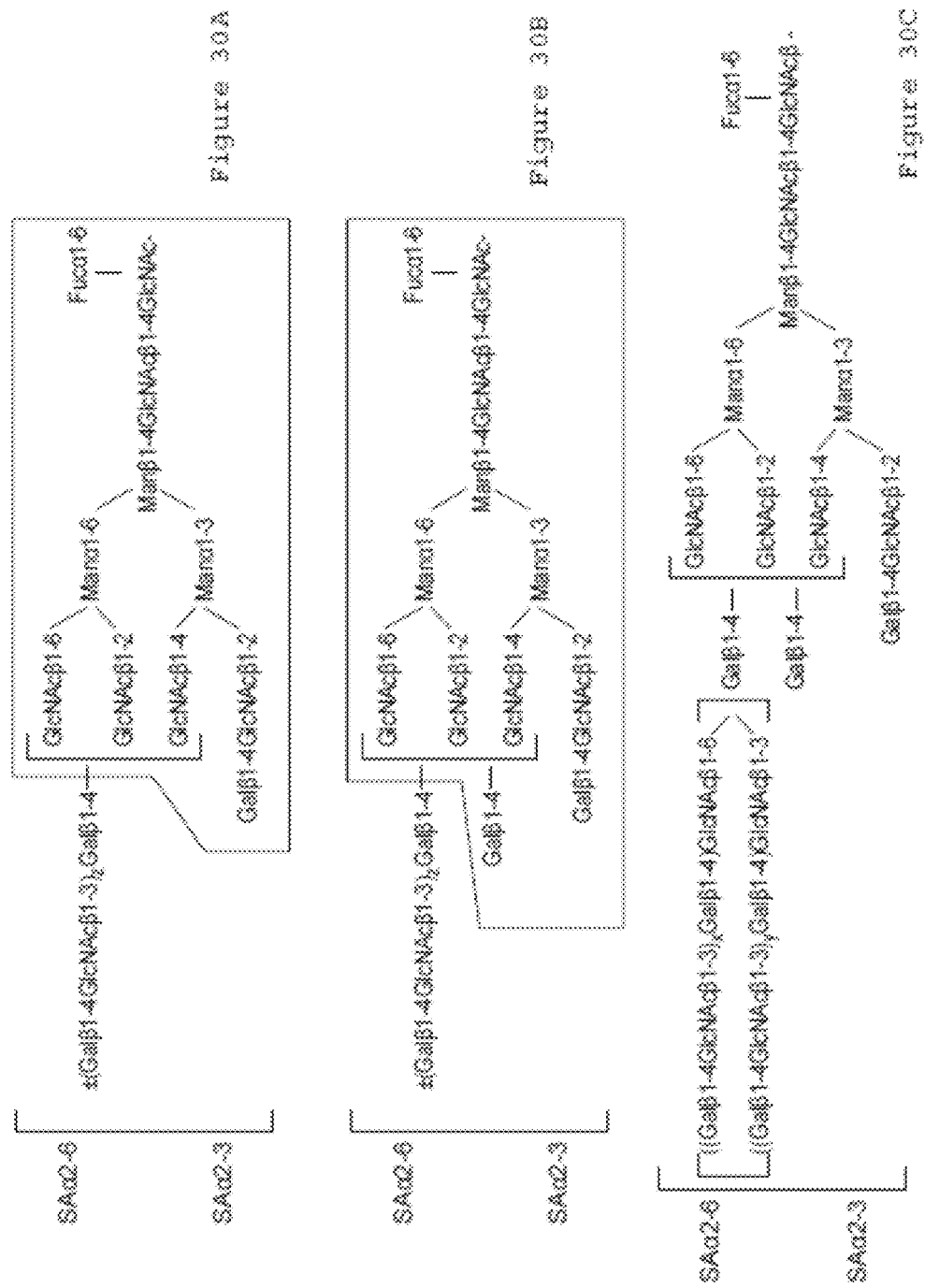

SEQUENCE LISTING

<160> NUMBER OF SEQ ID NOS: 69

<210> SEQ ID NO 1
<211> LENGTH: 523
<212> TYPE: DNA
<213> ORGANISM: Homo sapiens

<400> SEQUENCE: 1

```
ctcctggttc aaaagcagct aaaccaaaag aagcctccag acagccctga gatcacctaa        60
aaagctgcta ccaagacagc cacgaagatc ctaccaaaat gaagcgcttc ctcttcctcc       120
tactcaccat cagcctcctg gttatggtac agatacaaac tggactctca ggacaaaacg       180
acaccagcca aaccagcagc ccctcagcat ccagcaacat aagcggaggc attttcctt       240 tcttcgtggc caatgccata atccacctct tctgcttcag ttgaggtgac acgtctcagc       300
cttagccctg tgcccctga aacagctgcc accatcactc gcaagagaat ccctccatc        360 tttgggaggg gttgatgcca gacatcacca ggttgtagaa gttgacaggc agtgccatgg       420
gggcaacagc caaaataggg gggtaatgat gtagggcca agcagtgccc agctgggggt       480
caataaagtt acccttgtac ttgcaaaaaa aaaaaaaaaa aaa                         523
```

-continued

```
<210> SEQ ID NO 2
<211> LENGTH: 61
<212> TYPE: PRT
<213> ORGANISM: Homo sapiens

<400> SEQUENCE: 2

Met Lys Arg Phe Leu Phe Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60

<210> SEQ ID NO 3
<211> LENGTH: 12
<212> TYPE: PRT
<213> ORGANISM: Homo sapiens

<400> SEQUENCE: 3

Gly Gln Asn Asp Thr Ser Gln Thr Ser Ser Pro Ser
1               5                   10

<210> SEQ ID NO 4
<211> LENGTH: 11
<212> TYPE: PRT
<213> ORGANISM: Pan troglodytes

<400> SEQUENCE: 4

Ser Gln Asn Ala Thr Ser Gln Ser Ser Pro Ser
1               5                   10

<210> SEQ ID NO 5
<211> LENGTH: 24
<212> TYPE: PRT
<213> ORGANISM: Mus musculus

<400> SEQUENCE: 5

Gly Gln Ala Thr Thr Ala Ala Ser Gly Thr Asn Lys Asn Ser Thr Ser
1               5                   10                  15

Thr Lys Lys Thr Pro Leu Lys Ser
            20

<210> SEQ ID NO 6
<211> LENGTH: 46
<212> TYPE: PRT
<213> ORGANISM: Rattus norvegicus

<400> SEQUENCE: 6

Gly Gln Asn Ser Thr Ala Val Thr Thr Pro Ala Asn Lys Ala Ala Thr
1               5                   10                  15

Thr Ala Ala Ala Thr Thr Lys Ala Ala Ala Thr Thr Ala Thr Lys Thr
            20                  25                  30

Thr Thr Ala Val Arg Lys Thr Pro Gly Lys Pro Pro Lys Ala
        35                  40                  45

<210> SEQ ID NO 7
<211> LENGTH: 19
<212> TYPE: PRT
<213> ORGANISM: Canis familiaris

<400> SEQUENCE: 7
```

```
Gly Asn Ser Thr Thr Pro Arg Met Thr Thr Lys Lys Val Lys Ser Ala
1               5                   10                  15

Thr Pro Ala

<210> SEQ ID NO 8
<211> LENGTH: 22
<212> TYPE: DNA
<213> ORGANISM: Artificial Sequence
<220> FEATURE:
<223> OTHER INFORMATION: CD52-F primer

<400> SEQUENCE: 8
caaactggac tctcaggaca aa                                              22

<210> SEQ ID NO 9
<211> LENGTH: 22
<212> TYPE: DNA
<213> ORGANISM: Artificial Sequence
<220> FEATURE:
<223> OTHER INFORMATION: CD52-R primer

<400> SEQUENCE: 9
caactgaagc agaagaggtg ga                                              22

<210> SEQ ID NO 10
<211> LENGTH: 22
<212> TYPE: DNA
<213> ORGANISM: Artificial sequence
<220> FEATURE:
<223> OTHER INFORMATION: FOXP3-F primer

<400> SEQUENCE: 10
atggtttctg aagaaggcaa ac                                              22

<210> SEQ ID NO 11
<211> LENGTH: 23
<212> TYPE: DNA
<213> ORGANISM: Artificial Sequence
<220> FEATURE:
<223> OTHER INFORMATION: FOXP3-R primer

<400> SEQUENCE: 11
ggactacttc aagttccaca aca                                             23

<210> SEQ ID NO 12
<211> LENGTH: 22
<212> TYPE: DNA
<213> ORGANISM: Artificial Sequence
<220> FEATURE:
<223> OTHER INFORMATION: CTLA-4 F primer

<400> SEQUENCE: 12
aacctacatg atggggaatg ag                                              22

<210> SEQ ID NO 13
<211> LENGTH: 22
<212> TYPE: DNA
<213> ORGANISM: Artificial Sequence
<220> FEATURE:
<223> OTHER INFORMATION: CTLA-4 R primer

<400> SEQUENCE: 13
ttacataaat ctgggttccg tt                                              22
```

```
<210> SEQ ID NO 14
<211> LENGTH: 21
<212> TYPE: DNA
<213> ORGANISM: Artificial Sequence
<220> FEATURE:
<223> OTHER INFORMATION: GITR-F primer

<400> SEQUENCE: 14
gggaaattca gttttggctt c                                              21

<210> SEQ ID NO 15
<211> LENGTH: 20
<212> TYPE: DNA
<213> ORGANISM: Artificial Sequence
<220> FEATURE:
<223> OTHER INFORMATION: GITR-R primer

<400> SEQUENCE: 15
acagcgttgt gggtcttgtt                                                20

<210> SEQ ID NO 16
<211> LENGTH: 22
<212> TYPE: DNA
<213> ORGANISM: Artificial Sequence
<220> FEATURE:
<223> OTHER INFORMATION: CD127 F primer

<400> SEQUENCE: 16
ccttttgacc tgagtgtcgt ct                                             22

<210> SEQ ID NO 17
<211> LENGTH: 22
<212> TYPE: DNA
<213> ORGANISM: Artificial Sequence
<220> FEATURE:
<223> OTHER INFORMATION: CD127 R primer

<400> SEQUENCE: 17
cgtccatttg ttttcatcct tt                                             22

<210> SEQ ID NO 18
<211> LENGTH: 22
<212> TYPE: DNA
<213> ORGANISM: Artificial Sequence
<220> FEATURE:
<223> OTHER INFORMATION: IL2 alpha forward primer

<400> SEQUENCE: 18
tacaggatgc aactcctgtc tt                                             22

<210> SEQ ID NO 19
<211> LENGTH: 22
<212> TYPE: DNA
<213> ORGANISM: Artificial Sequence
<220> FEATURE:
<223> OTHER INFORMATION: IL2 alpha reverse primer

<400> SEQUENCE: 19
gctccagttg tagctgtgtt tt                                             22

<210> SEQ ID NO 20
<211> LENGTH: 22
<212> TYPE: DNA
<213> ORGANISM: Artificial sequence
<220> FEATURE:
<223> OTHER INFORMATION: IL2 beta forward primer
```

<400> SEQUENCE: 20
gctgttctcc atggctccct ac                                              22

<210> SEQ ID NO 21
<211> LENGTH: 20
<212> TYPE: DNA
<213> ORGANISM: Artificial sequence
<220> FEATURE:
<223> OTHER INFORMATION: IL2 beta reverse primer

<400> SEQUENCE: 21
gtcgggcttg atgatgtgct                                                 20

<210> SEQ ID NO 22
<211> LENGTH: 22
<212> TYPE: DNA
<213> ORGANISM: Artificial sequence
<220> FEATURE:
<223> OTHER INFORMATION: IL12 alpha forward primer

<400> SEQUENCE: 22
ctccagaagg ccagacaaac tc                                              22

<210> SEQ ID NO 23
<211> LENGTH: 22
<212> TYPE: DNA
<213> ORGANISM: Artificial sequence
<220> FEATURE:
<223> OTHER INFORMATION: IL12 alpha reverse primer

<400> SEQUENCE: 23
ccaatggtaa acaggcctcc ac                                              22

<210> SEQ ID NO 24
<211> LENGTH: 37
<212> TYPE: DNA
<213> ORGANISM: Artificial sequence
<220> FEATURE:
<223> OTHER INFORMATION: 1F1 primer

<400> SEQUENCE: 24
gaagttctgt tccaggggcc catcgaaggt cgtggtg                              37

<210> SEQ ID NO 25
<211> LENGTH: 48
<212> TYPE: DNA
<213> ORGANISM: Artificial sequence
<220> FEATURE:
<223> OTHER INFORMATION: 1R1 primer

<400> SEQUENCE: 25 tcattttcg aactgcgggt ggctccaggc gcttttaccc ggagacag                   48

<210> SEQ ID NO 26
<211> LENGTH: 30
<212> TYPE: DNA
<213> ORGANISM: Artificial sequence
<220> FEATURE:
<223> OTHER INFORMATION: 1F2 primer

<400> SEQUENCE: 26
gggggttccg ggggactgga agttctgttc                                      30

<210> SEQ ID NO 27
<211> LENGTH: 30

```
<212> TYPE: DNA
<213> ORGANISM: Artificial sequence
<220> FEATURE:
<223> OTHER INFORMATION: 1R2 primer

<400> SEQUENCE: 27
cttgatatcg aattctcatt tttcgaactg                                      30

<210> SEQ ID NO 28
<211> LENGTH: 35
<212> TYPE: DNA
<213> ORGANISM: Artificial sequence
<220> FEATURE:
<223> OTHER INFORMATION: 2F primer

<400> SEQUENCE: 28
cgctgttacg gatccccacc atgaagcgct tcctc                                35

<210> SEQ ID NO 29
<211> LENGTH: 30
<212> TYPE: DNA
<213> ORGANISM: Artificial sequence
<220> FEATURE:
<223> OTHER INFORMATION: 2R1 primer

<400> SEQUENCE: 29
tccaccgcta cctcctgagg ggctgctggt                                      30

<210> SEQ ID NO 30
<211> LENGTH: 30
<212> TYPE: DNA
<213> ORGANISM: Artificial sequence
<220> FEATURE:
<223> OTHER INFORMATION: 2R2 primer

<400> SEQUENCE: 30
tccaccgcta cctcctgaga gtccagtttg                                      30

<210> SEQ ID NO 31
<211> LENGTH: 24
<212> TYPE: DNA
<213> ORGANISM: Artificial sequence
<220> FEATURE:
<223> OTHER INFORMATION: CD52 forward primer

<400> SEQUENCE: 31
gttgtgattc agatacaaac agga                                            24

<210> SEQ ID NO 32
<211> LENGTH: 22
<212> TYPE: DNA
<213> ORGANISM: Artificial sequence
<220> FEATURE:
<223> OTHER INFORMATION: CD52 reverse primer

<400> SEQUENCE: 32
aggtattggc aaagaagagg aa                                              22

<210> SEQ ID NO 33
<211> LENGTH: 23
<212> TYPE: DNA
<213> ORGANISM: Artificial sequence
<220> FEATURE:
<223> OTHER INFORMATION: IL-2 forward primer

<400> SEQUENCE: 33
```
tcaagctcca cttcaagctc tac                                           23

<210> SEQ ID NO 34
<211> LENGTH: 22
<212> TYPE: DNA
<213> ORGANISM: Artificial sequence
<220> FEATURE:
<223> OTHER INFORMATION: IL-2 reverse primer

<400> SEQUENCE: 34
cctgtaattc tccatcctgc tc                                            22

<210> SEQ ID NO 35
<211> LENGTH: 22
<212> TYPE: DNA
<213> ORGANISM: Artificial sequence
<220> FEATURE:
<223> OTHER INFORMATION: IL-4 forward primer

<400> SEQUENCE: 35
tgagagagat catcggcatt tt                                            22

<210> SEQ ID NO 36
<211> LENGTH: 22
<212> TYPE: DNA
<213> ORGANISM: Artificial sequence
<220> FEATURE:
<223> OTHER INFORMATION: IL-4 reverse primer

<400> SEQUENCE: 36
ctctctgtgg tgttcttcgt tg                                            22

<210> SEQ ID NO 37
<211> LENGTH: 22
<212> TYPE: DNA
<213> ORGANISM: Artificial sequence
<220> FEATURE:
<223> OTHER INFORMATION: IL-10 forward primer

<400> SEQUENCE: 37
tcggaaatga tccagtttta cc                                            22

<210> SEQ ID NO 38
<211> LENGTH: 21
<212> TYPE: DNA
<213> ORGANISM: Artificial sequence
<220> FEATURE:
<223> OTHER INFORMATION: IL-10 reverse primer

<400> SEQUENCE: 38
atcctgaggg tcttcagctt c                                             21

<210> SEQ ID NO 39
<211> LENGTH: 21
<212> TYPE: DNA
<213> ORGANISM: Artificial sequence
<220> FEATURE:
<223> OTHER INFORMATION: IL-13 forward primer

<400> SEQUENCE: 39
gagctgagca acatcacaca a                                             21

<210> SEQ ID NO 40
<211> LENGTH: 21
<212> TYPE: DNA
<213> ORGANISM: Artificial sequence

```
<220> FEATURE:
<223> OTHER INFORMATION: IL-13 reverse primer

<400> SEQUENCE: 40
aatccagggc tacacagaac c                                          21

<210> SEQ ID NO 41
<211> LENGTH: 22
<212> TYPE: DNA
<213> ORGANISM: Artificial sequence
<220> FEATURE:
<223> OTHER INFORMATION: Fox3P forward primer

<400> SEQUENCE: 41
atgttcgcct acttcagaaa cc                                         22

<210> SEQ ID NO 42
<211> LENGTH: 22
<212> TYPE: DNA
<213> ORGANISM: Artificial sequence
<220> FEATURE:
<223> OTHER INFORMATION: FoxP3 reverse primer

<400> SEQUENCE: 42
caaattcatc tacggtccac ac                                         22

<210> SEQ ID NO 43
<211> LENGTH: 22
<212> TYPE: DNA
<213> ORGANISM: Artificial sequence
<220> FEATURE:
<223> OTHER INFORMATION: CD127 forward primer

<400> SEQUENCE: 43
gcccaccaga aacagttaga ag                                         22

<210> SEQ ID NO 44
<211> LENGTH: 22
<212> TYPE: DNA
<213> ORGANISM: Artificial sequence
<220> FEATURE:
<223> OTHER INFORMATION: CD127 reverse primer

<400> SEQUENCE: 44
agtcagggga cctagaggaa ag                                         22

<210> SEQ ID NO 45
<211> LENGTH: 22
<212> TYPE: DNA
<213> ORGANISM: Artificial sequence
<220> FEATURE:
<223> OTHER INFORMATION: CTLA-4 forward primer

<400> SEQUENCE: 45
agtttcctgg tcactgctgt tt                                         22

<210> SEQ ID NO 46
<211> LENGTH: 22
<212> TYPE: DNA
<213> ORGANISM: Artificial sequence
<220> FEATURE:
<223> OTHER INFORMATION: CTLA-4 reverse primer

<400> SEQUENCE: 46
ttttcacatt ctggctctgt tg                                         22
```

```
<210> SEQ ID NO 47
<211> LENGTH: 22
<212> TYPE: DNA
<213> ORGANISM: Artificial sequence
<220> FEATURE:
<223> OTHER INFORMATION: FASLG forward primer

<400> SEQUENCE: 47
cggtggtatt tttcatggtt ct                                              22

<210> SEQ ID NO 48
<211> LENGTH: 23
<212> TYPE: DNA
<213> ORGANISM: Artificial sequence
<220> FEATURE:
<223> OTHER INFORMATION: FASLG reverse primer

<400> SEQUENCE: 48
tgatacttta aggctttggt tgg                                             23

<210> SEQ ID NO 49
<211> LENGTH: 22
<212> TYPE: DNA
<213> ORGANISM: Artificial sequence
<220> FEATURE:
<223> OTHER INFORMATION: TGFb1 forward primer

<400> SEQUENCE: 49
tattgcttca gctccacaga ga                                              22

<210> SEQ ID NO 50
<211> LENGTH: 22
<212> TYPE: DNA
<213> ORGANISM: Artificial sequence
<220> FEATURE:
<223> OTHER INFORMATION: TGFb1 reverse primer

<400> SEQUENCE: 50
cagacagaag ttggcatggt ag                                              22

<210> SEQ ID NO 51
<211> LENGTH: 22
<212> TYPE: DNA
<213> ORGANISM: Artificial sequence
<220> FEATURE:
<223> OTHER INFORMATION: TGFb2 forward primer

<400> SEQUENCE: 51
taagagggat cttggatgga aa                                              22

<210> SEQ ID NO 52
<211> LENGTH: 22
<212> TYPE: DNA
<213> ORGANISM: Artificial sequence
<220> FEATURE:
<223> OTHER INFORMATION: TGFb2 reverse primer

<400> SEQUENCE: 52
ctgaggactt tggtgtgttg ag                                              22

<210> SEQ ID NO 53
<211> LENGTH: 22
<212> TYPE: DNA
<213> ORGANISM: Artificial sequence
<220> FEATURE:
<223> OTHER INFORMATION: IFNg forward primer
```

```
<400> SEQUENCE: 53
caaaaggatg gtgacatgaa aa                                            22

<210> SEQ ID NO 54
<211> LENGTH: 22
<212> TYPE: DNA
<213> ORGANISM: Artificial sequence
<220> FEATURE:
<223> OTHER INFORMATION: IFNg reverse primer

<400> SEQUENCE: 54
ttgctgttgc tgaagaaggt ag                                            22

<210> SEQ ID NO 55
<211> LENGTH: 22
<212> TYPE: DNA
<213> ORGANISM: Artificial sequence
<220> FEATURE:
<223> OTHER INFORMATION: IL-12 alpha forward primer

<400> SEQUENCE: 55
tcacgctacc tcctcttttt gg                                            22

<210> SEQ ID NO 56
<211> LENGTH: 23
<212> TYPE: DNA
<213> ORGANISM: Artificial sequence
<220> FEATURE:
<223> OTHER INFORMATION: IL-12 alpha reverse primer

<400> SEQUENCE: 56
catctgtggt cttcagcagg ttt                                           23

<210> SEQ ID NO 57
<211> LENGTH: 22
<212> TYPE: DNA
<213> ORGANISM: Artificial sequence
<220> FEATURE:
<223> OTHER INFORMATION: Ebi3 forward primer

<400> SEQUENCE: 57
ccttcccgga catcttctct ct                                            22

<210> SEQ ID NO 58
<211> LENGTH: 21
<212> TYPE: DNA
<213> ORGANISM: Artificial sequence
<220> FEATURE:
<223> OTHER INFORMATION: Ebi3 reverse primer

<400> SEQUENCE: 58
gcaatacttg gcatggggtt t                                             21

<210> SEQ ID NO 59
<211> LENGTH: 22
<212> TYPE: DNA
<213> ORGANISM: Artificial sequence
<220> FEATURE:
<223> OTHER INFORMATION: RARA forward primer

<400> SEQUENCE: 59
ggacaagaac tgcatcatca ac                                            22

<210> SEQ ID NO 60
```

```
<211> LENGTH: 20
<212> TYPE: DNA
<213> ORGANISM: Artificial sequence
<220> FEATURE:
<223> OTHER INFORMATION: RARA reverse primer

<400> SEQUENCE: 60
gcttgggtgc ctctttcttc                                          20

<210> SEQ ID NO 61
<211> LENGTH: 22
<212> TYPE: DNA
<213> ORGANISM: Artificial sequence
<220> FEATURE:
<223> OTHER INFORMATION: GITR forward primer

<400> SEQUENCE: 61
cctaggtcag ccgagtgtag tt                                       22

<210> SEQ ID NO 62
<211> LENGTH: 22
<212> TYPE: DNA
<213> ORGANISM: Artificial sequence
<220> FEATURE:
<223> OTHER INFORMATION: GITR reverse primer

<400> SEQUENCE: 62
cacatatgca cctttctttt gg                                       22

<210> SEQ ID NO 63
<211> LENGTH: 23
<212> TYPE: DNA
<213> ORGANISM: Artificial sequence
<220> FEATURE:
<223> OTHER INFORMATION: GRANZB forward primer

<400> SEQUENCE: 63
tccttattcg agaggacttt gtg                                      23

<210> SEQ ID NO 64
<211> LENGTH: 22
<212> TYPE: DNA
<213> ORGANISM: Artificial sequence
<220> FEATURE:
<223> OTHER INFORMATION: GRANZB reverse primer

<400> SEQUENCE: 64
ctgggtcttc tcctgttctt tg                                       22

<210> SEQ ID NO 65
<211> LENGTH: 22
<212> TYPE: DNA
<213> ORGANISM: Artificial sequence
<220> FEATURE:
<223> OTHER INFORMATION: ALDH1A forward primer

<400> SEQUENCE: 65
acaggagagc aagtgtgtga ag                                       22

<210> SEQ ID NO 66
<211> LENGTH: 22
<212> TYPE: DNA
<213> ORGANISM: Artificial sequence
<220> FEATURE:
<223> OTHER INFORMATION: ALDH1A2 reverse primer

<400> SEQUENCE: 66
```

```
tccacacaga accaagagag aa                                              22

<210> SEQ ID NO 67
<211> LENGTH: 20
<212> TYPE: DNA
<213> ORGANISM: Artificial sequence
<220> FEATURE:
<223> OTHER INFORMATION: ACTIN forward primer

<400> SEQUENCE: 67
gatctggcac cacaccttct                                                 20

<210> SEQ ID NO 68
<211> LENGTH: 20
<212> TYPE: DNA
<213> ORGANISM: Artificial sequence
<220> FEATURE:
<223> OTHER INFORMATION: ACTIN reverse primer

<400> SEQUENCE: 68
ggggtgttga aggtctcaaa                                                 20

<210> SEQ ID NO 69
<211> LENGTH: 697
<212> TYPE: PRT
<213> ORGANISM: Homo sapiens

<400> SEQUENCE: 69
```

Met Leu Leu Pro Leu Leu Leu Ser Ser Leu Leu Gly Gly Ser Gln Ala
1               5                   10                  15

Met Asp Gly Arg Phe Trp Ile Arg Val Gln Glu Ser Val Met Val Pro
            20                  25                  30

Glu Gly Leu Cys Ile Ser Val Pro Cys Ser Phe Ser Tyr Pro Arg Gln
        35                  40                  45

Asp Trp Thr Gly Ser Thr Pro Ala Tyr Gly Tyr Trp Phe Lys Ala Val
    50                  55                  60

Thr Glu Thr Thr Lys Gly Ala Pro Val Ala Thr Asn His Gln Ser Arg
65                  70                  75                  80

Glu Val Glu Met Ser Thr Arg Gly Arg Phe Gln Leu Thr Gly Asp Pro
                85                  90                  95

Ala Lys Gly Asn Cys Ser Leu Val Ile Arg Asp Ala Gln Met Gln Asp
            100                 105                 110

Glu Ser Gln Tyr Phe Phe Arg Val Glu Arg Gly Ser Tyr Val Arg Tyr
        115                 120                 125

Asn Phe Met Asn Asp Gly Phe Phe Leu Lys Val Thr Ala Leu Thr Gln
    130                 135                 140

Lys Pro Asp Val Tyr Ile Pro Glu Thr Leu Glu Pro Gly Gln Pro Val
145                 150                 155                 160

Thr Val Ile Cys Val Phe Asn Trp Ala Phe Glu Glu Cys Pro Pro Pro
                165                 170                 175

Ser Phe Ser Trp Thr Gly Ala Ala Leu Ser Ser Gln Gly Thr Lys Pro
            180                 185                 190

Thr Thr Ser His Phe Ser Val Leu Ser Phe Thr Pro Arg Pro Gln Asp
        195                 200                 205

His Asn Thr Asp Leu Thr Cys His Val Asp Phe Ser Arg Lys Gly Val
    210                 215                 220

Ser Val Gln Arg Thr Val Arg Leu Arg Val Ala Tyr Ala Pro Arg Asp
225                 230                 235                 240

```
Leu Val Ile Ser Ile Ser Arg Asp Asn Thr Pro Ala Leu Glu Pro Gln
                245                 250                 255

Pro Gln Gly Asn Val Pro Tyr Leu Glu Ala Gln Lys Gly Gln Phe Leu
            260                 265                 270

Arg Leu Leu Cys Ala Ala Asp Ser Gln Pro Pro Ala Thr Leu Ser Trp
        275                 280                 285

Val Leu Gln Asn Arg Val Leu Ser Ser His Pro Trp Gly Pro Arg
    290                 295                 300

Pro Leu Gly Leu Glu Leu Pro Gly Val Lys Ala Gly Asp Ser Gly Arg
305                 310                 315                 320

Tyr Thr Cys Arg Ala Glu Asn Arg Leu Gly Ser Gln Gln Arg Ala Leu
                325                 330                 335

Asp Leu Ser Val Gln Tyr Pro Pro Glu Asn Leu Arg Val Met Val Ser
            340                 345                 350

Gln Ala Asn Arg Thr Val Leu Glu Asn Leu Gly Asn Gly Thr Ser Leu
        355                 360                 365

Pro Val Leu Glu Gly Gln Ser Leu Cys Leu Val Cys Val Thr His Ser
    370                 375                 380

Ser Pro Pro Ala Arg Leu Ser Trp Thr Gln Arg Gly Asn Val Leu Ser
385                 390                 395                 400

Pro Ser Gln Pro Ser Asp Pro Gly Val Leu Glu Leu Pro Arg Val Gln
                405                 410                 415

Val Glu His Glu Gly Glu Phe Thr Cys His Ala Arg His Pro Leu Gly
            420                 425                 430

Ser Gln His Val Ser Leu Ser Leu Ser Val His Tyr Ser Pro Lys Leu
        435                 440                 445

Leu Gly Pro Ser Cys Ser Trp Glu Ala Glu Gly Leu His Cys Ser Cys
    450                 455                 460

Ser Ser Gln Ala Ser Pro Ala Pro Ser Leu Arg Trp Trp Leu Gly Glu
465                 470                 475                 480

Glu Leu Leu Glu Gly Asn Ser Ser Gln Asp Ser Phe Glu Val Thr Pro
                485                 490                 495

Ser Ser Ala Gly Pro Trp Ala Asn Ser Ser Leu Ser Leu His Gly Gly
            500                 505                 510

Leu Ser Ser Gly Leu Arg Leu Arg Cys Glu Ala Trp Asn Val His Gly
        515                 520                 525

Ala Gln Ser Gly Ser Ile Leu Gln Leu Pro Asp Lys Lys Gly Leu Ile
    530                 535                 540

Ser Thr Ala Phe Ser Asn Gly Ala Phe Leu Gly Ile Gly Ile Thr Ala
545                 550                 555                 560

Leu Leu Phe Leu Cys Leu Ala Leu Ile Ile Met Lys Ile Leu Pro Lys
                565                 570                 575

Arg Arg Thr Gln Thr Glu Thr Pro Arg Pro Arg Phe Ser Arg His Ser
            580                 585                 590

Thr Ile Leu Asp Tyr Ile Asn Val Val Pro Thr Ala Gly Pro Leu Ala
        595                 600                 605

Gln Lys Arg Asn Gln Lys Ala Thr Pro Asn Ser Pro Arg Thr Pro Leu
    610                 615                 620

Pro Pro Gly Ala Pro Ser Pro Glu Ser Lys Lys Asn Gln Lys Lys Gln
625                 630                 635                 640

Tyr Gln Leu Pro Ser Phe Pro Gly Pro Lys Ser Ser Thr Gln Ala Pro
                645                 650                 655
```

```
Glu Ser Gln Glu Ser Gln Glu Glu Leu His Tyr Ala Thr Leu Asn Phe
            660                 665                 670
Pro Gly Val Arg Pro Arg Pro Glu Ala Arg Met Pro Lys Gly Thr Gln
        675                 680                 685
Ala Asp Tyr Ala Glu Val Lys Phe Gln
        690                 695
```

SOLUBLE MEDIATOR

FIELD OF THE INVENTION

The present disclosure generally relates to cell populations and soluble mediators capable of suppressing T-cell activation, and to the use of such cell populations and soluble mediators to suppress T-cell activation, such as in the treatment of diseases or conditions mediated by effector T-cell function. The disclosure also relates to methods of detecting the presence of a marker in a subject, which marker is indicative of the subject's susceptibility to diseases or conditions mediated by effector T-cell function.

BACKGROUND OF THE INVENTION

Regulatory T-cells (Treg cells; also known as suppressor T-cells) are subpopulations of T-cells that maintain immune homeostasis and help avert autoimmune disease (Sakaguchi et al., 2008; Shevach, 2006; Vignali et al., 2008). Interest in Treg cells is focused predominantly on prototypic CD4$^+$ CD25$^+$ Treg cells that are programmed by the transcription factor FoxP3 (Fontenot et al., 2003; Hori et al., 2003). In resting polyspecific populations these Treg cells are characterised in the mouse both as 'natural', thymus-derived and induced 'adaptive' cells that suppress the activation, proliferation and functions of other T-cells (Sakaguchi et al., 2008; Shevach, 2006). However, in human blood CD4$^+$ Treg cells are not as reliably distinguished by FoxP3 expression (Roncarolo and Gregori, 2008; Allan et al., 2007; Gavin et al., 2006). Thus, CD4$^+$ T-cells with markers of either naïve or memory cells were shown to have similar suppressor functions despite low and high expression, respectively, of FoxP3 (Miyara et al., 2009). Other surface markers of human CD4$^+$ CD25$^+$ FoxP3$^+$ Treg cells such as decreased expression of the IL-7 receptor, CD127 (Liu et al., 2006; Seddiki et al., 2006), are not specific for Treg cells.

Aside from the paucity of specific cell surface markers, the mechanisms underlying suppression by CD4$^+$ CD25$^+$ FoxP3$^+$ Treg cells remain controversial. In the mouse, suppression ex vivo has been shown to require cell-cell contact but has been attributed to multiple mechanisms (Vignali et al., 2008; Shevach, 2009; Sakaguchi et al., 2009); even less is known about the function of similar human Treg cells. Furthermore, other types of both CD4$^+$ and CD8$^+$ Treg cells that differ in proposed mechanisms of suppressor function have been described in the context of various tissue sites or diseases (Vignali et al., 2008).

Treg cells induced by administration of autoantigens have been shown to protect against some autoimmune diseases in certain animal models (reviewed by von Herrath and Harrison, 2003). For example, in the nonobese diabetic (NOD) mouse model of type 1 diabetes (T1D) CD4$^+$ Treg cells induced by administered pancreatic islet autoantigens such as insulin (Bergerot et al., 1994) or glutamic acid decarboxylase 65 (GAD65) (Tisch et al., 1999), or transfer of CD4$^+$ Treg cells induced by proinsulin (Every et al., 2006) or a putative pancreatic islet antigen (Tang et al., 2004), have been shown to protect against autoimmune diabetes. However, in these models Treg cells have been studied in resting, polyspecific populations and not during the host's response to a particular antigen. Recently, proinsulin- and GAD65-specific human CD4$^+$ T-cell clones were generated and Treg clones were distinguished by their suppressor function in vitro (Dromey et al., 2011). The cell surface membrane-anchored glycoprotein CD52 was shown to be upregulated in these expanded CD4$^+$ Treg clones. However, the mechanism of immune suppression has not previously been characterized.

SUMMARY OF THE INVENTION

The present inventors have identified a soluble mediator of Treg cell suppression. Accordingly, the present disclosure provides a pharmaceutical composition comprising any one or more of:
  i) soluble CD52 glycoprotein,
  ii) a fusion protein comprising soluble CD52 glycoprotein as a first protein, and a second protein;
  iii) a polynucleotide encoding the peptide portion of soluble CD52 glycoprotein of part i) or the fusion protein of part ii);
  iv) a vector comprising the polynucleotide of part iii);
  v) an isolated cell comprising the polynucleotide of part iii) or the vector of part iv);
  vi) an isolated CD52$^{hi}$ cell capable of producing soluble CD52 glycoprotein;
  vii) an isolated cell population comprising a plurality of CD52$^{hi}$ cells capable of producing soluble CD52 glycoprotein;
  viii) cell culture medium, or a fraction thereof comprising soluble CD52 glycoprotein, isolated from a cell culture comprising the cell of part vi) or the cell population of part vii); and
  ix) an agent capable of increasing the level of expression of soluble CD52 glycoprotein by a cell;
  and a pharmaceutically acceptable carrier.

In a preferred embodiment, the soluble CD52 glycoprotein comprises an amino acid sequence at least 60% identical to the amino acid sequence of any one or more of GQNDTSQTSSPS (SEQ ID NO: 3), SQNATSQSSPS (SEQ ID NO: 4), GQATTAASGTNKNSTSTKKTPLKS (SEQ ID NO: 5), GQNSTAVTTPANKAATTAAATTKAAATTATKTTTAVRKTPGKPPKA (SEQ ID NO: 6) or GNSTTPRMTTKKVKSATPA (SEQ ID NO:7) and a carbohydrate. More preferably, the glycoprotein comprises an amino acid sequence which is at least 65%, at least 70%, at least 75%, at least 80%, at least 85%, at least 90%, at least 95% identical, or is 100% identical, to any one or more of the amino acid sequences identified in SEQ ID NOs: 3, 4, 5, 6 or 7.

In one example, the glycoprotein comprises an amino acid sequence at least 60% at least 65%, at least 70%, at least 75%, at least 80%, at least 85%, at least 90%, at least 95% identical, or is 100% identical to the amino acid sequence of SEQ ID NO: 3, which represents the human soluble CD52 fragment.

Preferably, any one or more of the soluble CD52 glycoprotein, fusion protein, polynucleotide, vector, cell, cell population, cell culture medium and agent is present in an amount sufficient to suppress effector T-cell function and/or an immune response.

In a further embodiment, the soluble CD52 glycoprotein, fusion protein, polynucleotide, vector, cell, cell population, cell culture medium and agent is present in an amount sufficient such that the suppression of the immune response results in tolerance to at least one antigen such an autoantigen.

In another embodiment, any one or more of the soluble CD52 glycoprotein, fusion protein, cell, cell population, cell culture medium and agent is capable of suppressing effector T-cell function and/or is capable of reducing an immune response such as an immune response to an autoantigen.

In an embodiment, the composition comprises one or more of the soluble CD52 glycoprotein, fusion protein, cell culture medium or agent, and is formulated for mucosal and/or transdermal administration.

In a further embodiment, the composition further comprises insulin and/or an autoantigen.

The present disclosure also provides a fusion protein comprising soluble CD52 glycoprotein as a first protein, and a second protein.

Preferably, the soluble CD52 glycoprotein of the fusion protein comprises an amino acid sequence which is at least 60%, at least 65%, at least 70%, at least 75%, at least 80%, at least 85%, at least 90%, at least 95% identical, or is 100% identical, to any one or more of the amino acid sequences identified in SEQ ID NOs: 3, 4, 5, 6 or 7.

Preferably, the fusion protein is capable of suppressing effector T-cell function and/or is capable of reducing an immune response such as an immune response to an autoantigen. In an embodiment, the fusion protein reduces the immune response to an extent that it results in tolerance to at least one antigen such an autoantigen.

The second protein may be any protein capable of increasing the stability and/or solubility of the soluble CD52 glycoprotein, of enhancing the process of making the soluble CD52 glycoprotein by recombinant methods, or of enhancing the therapeutic effect of the soluble CD52 glycoprotein. In one example, the second protein may comprise an antibody fragment, such as an Fc.

Preferably, the fusion protein is soluble.

The present disclosure also provides an isolated or recombinant polynucleotide encoding the fusion protein disclosed herein.

The present disclosure also provides a vector comprising the polynucleotide disclosed herein.

The present disclosure also provides an isolated cell comprising the polynucleotide and/or the vector disclosed herein. The cell may be a mammalian cell.

In one example, the cell is as HEK293T cell. In another example, the cell is a Daudi B lymphoblast cell.

In addition, the present disclosure provides a method of producing the fusion protein, comprising expressing the polynucleotide or vector disclosed herein under glycosylation-permitting conditions.

In an embodiment, the glycosylation-permitting conditions comprise expressing the fusion protein in a host cell, such as a mammalian cell.

The present disclosure also provides for the use of any one or more of:
i) soluble CD52 glycoprotein,
ii) a fusion protein comprising soluble CD52 glycoprotein as a first protein, and a second protein;
iii) a polynucleotide encoding the peptide portion of soluble CD52 glycoprotein of part i) or the fusion protein of part ii);
iv) a vector comprising the polynucleotide of part iii);
v) an isolated cell comprising the polynucleotide of part iii) or the vector of part iv);
vi) an isolated $CD52^{hi}$ cell capable of producing soluble CD52 glycoprotein;
vii) an isolated cell population comprising a plurality of $CD52^{hi}$ cells capable of producing soluble CD52 glycoprotein;
viii) cell culture medium, or a fraction thereof comprising soluble CD52 glycoprotein, isolated from a cell culture comprising the cell of part vi) or the cell population of part vii);
ix) an agent capable of increasing the level of expression of soluble CD52 glycoprotein by a cell; and
x) the pharmaceutical composition of the invention,
to suppress effector T-cell function and/or to reduce an immune response, such as an immune response to an autoantigen.

The present disclosure also provides a method of treating or preventing a disease or condition mediated by effector T-cell function, inflammation or sepsis, in a subject, the method comprising administering a therapeutically effective amount of any one or more of:
i) soluble CD52 glycoprotein,
ii) a fusion protein comprising soluble CD52 glycoprotein as a first protein, and a second protein;
iii) a polynucleotide encoding the peptide portion of soluble CD52 glycoprotein of part i) or the fusion protein of part ii);
iv) a vector comprising the polynucleotide of part iii);
v) an isolated cell comprising the polynucleotide of part iii) or the vector of part iv);
vi) an isolated $CD52^{hi}$ cell capable of producing soluble CD52 glycoprotein;
vii) an isolated cell population comprising a plurality of $CD52^{hi}$ cells capable of producing soluble CD52 glycoprotein;
viii) cell culture medium, or a fraction thereof comprising soluble CD52 glycoprotein, isolated from a cell culture comprising the cell of part vi) or the cell population of part vii);
ix) an agent capable of increasing the level of expression of soluble CD52 glycoprotein by a cell; and
x) the pharmaceutical composition of the invention,
to the subject.

In an embodiment, the soluble CD52 glycoprotein, fusion protein, cell culture medium, agent or composition is administered at a mucosal or transdermal site.

The present disclosure also provides any one or more of:
i) soluble CD52 glycoprotein,
ii) a fusion protein comprising soluble CD52 glycoprotein as a first protein, and a second protein;
iii) a polynucleotide encoding the peptide portion of soluble CD52 glycoprotein of part i) or the fusion protein of part ii);
iv) a vector comprising the polynucleotide of part iii);
v) an isolated cell comprising the polynucleotide of part iii) or the vector of part iv);
vi) an isolated $CD52^{hi}$ cell capable of producing soluble CD52 glycoprotein;
vii) an isolated cell population comprising a plurality of $CD52^{hi}$ cells capable of producing soluble CD52 glycoprotein;
viii) cell culture medium, or a fraction thereof comprising soluble CD52 glycoprotein, isolated from a cell culture comprising the cell of part vi) or the cell population of part vii);
ix) an agent capable of increasing the level of expression of soluble CD52 glycoprotein by a cell; and
x) the pharmaceutical composition of the invention,
for use in treating or preventing a disease or condition mediated by effector T-cell function, inflammation or sepsis.

Furthermore, the present disclosure provides for the use of any one or more of:
i) soluble CD52 glycoprotein,
ii) a fusion protein comprising soluble CD52 glycoprotein as a first protein, and a second protein;

iii) a polynucleotide encoding the peptide portion of soluble CD52 glycoprotein of part i) or the fusion protein of part ii);
iv) a vector comprising the polynucleotide of part iii);
v) an isolated cell comprising the polynucleotide of part iii) or the vector of part iv);
vi) an isolated CD52$^{hi}$ cell capable of producing soluble CD52 glycoprotein;
vii) an isolated cell population comprising a plurality of CD52$^{hi}$ cells capable of producing soluble CD52 glycoprotein;
viii) cell culture medium, or a fraction thereof comprising soluble CD52 glycoprotein, isolated from a cell culture comprising the cell of part vi) or the cell population of part vii);
ix) an agent capable of increasing the level of expression of soluble CD52 glycoprotein by a cell; and
x) the pharmaceutical composition of the invention,
in the manufacture of a medicament for the treatment or prevention of a disease or condition mediated by effector T-cell function, inflammation or sepsis.

In an embodiment, the medicament is formulated for administration at a mucosal or transdermal site.

In one example, the disease mediated by effector T-cell function is an autoimmune disease, such as type I diabetes or rheumatoid arthritis. In another example, the condition mediated by effector T-cell function is an allograft rejection or a graft-versus-host reaction.

The present disclosure also provides a method of diagnosing a subject's susceptibility to developing a disease or condition mediated by effector T-cell function, inflammation or sepsis, the method comprising:
detecting the level of soluble CD52 glycoprotein in a sample taken from the subject; and
comparing the level of soluble CD52 glycoprotein detected in the sample taken from the subject with a reference level determined from one or more healthy subjects, wherein a lower level of soluble CD52 glycoprotein detected in the sample taken from the subject compared to the reference level indicates that the subject has an increased susceptibility to developing a disease or condition mediated by effector T-cell function, inflammation or sepsis.

The present disclosure also provides a method of diagnosing a subject's susceptibility to developing a disease or condition mediated by effector T-cell function, inflammation or sepsis, the method comprising:
detecting the frequency of CD52$^{hi}$ cells in a sample taken from a subject; and
comparing the frequency of CD52$^{hi}$ cells detected in the sample taken from the subject with a reference level determined from one or more healthy subjects, wherein a lower frequency of CD52$^{hi}$ cells detected in the sample taken from the subject compared to the reference level indicates that the subject has an increased susceptibility to developing a disease or condition mediated by effector T-cell function, inflammation or sepsis.

The present disclosure also provides a method of diagnosing a subject's susceptibility to developing a disease or condition mediated by effector T-cell function, inflammation or sepsis, the method comprising:
detecting the activity of CD52$^{hi}$ cells in a sample taken from a subject; and
comparing the activity of CD52$^{hi}$ cells detected in the sample taken from the subject with a reference level determined from one or more healthy subjects, wherein a reduced activity of CD52$^{hi}$ cells detected in the sample taken from the subject compared to the reference level indicates that the subject has an increased susceptibility to developing a disease or condition mediated by effector T-cell function, inflammation or sepsis.

In one example, the frequency of CD52$^{hi}$ cells is determined by detecting the level of membrane bound CD52 in the sample, by detecting the level of expression of CD52 protein in the sample, and/or by detecting the level of expression of CD52 mRNA in the sample.

In an embodiment, the sample is taken from a subject to which an antigen has been administered.

In another embodiment, the sample is taken from a local disease site in the subject.

The present disclosure also provides a method of determining a subject's suitability for entry into a drug screening trial, comprising performing the method of the invention and identifying the subject as being more suitable for entry into a drug screening trial if the subject has a lower level of soluble CD52 glycoprotein, a lower frequency of CD52$^{hi}$ cells, or a reduced activity of CD52$^{hi}$ cells than the reference sample. For example, the drug screening trial is an anti-diabetic drug screening trial.

In addition, the present disclosure also provides a method of identifying an agent capable of mimicking the effector T-cell-suppressing, and/or immune response suppressing, function of a soluble CD52 glycoprotein, the method comprising determining whether a test agent suppresses effector T-cell function and/or an immune response.

The present disclosure also provides a method of identifying a potential therapeutic agent for the treatment or prevention of a disease or condition mediated by effector T-cell function, inflammation or sepsis, the method comprising contacting a test agent with a CD52$^{hi}$ cell or CD52$^{hi}$ cell population, and detecting any one or more of the level of soluble CD52 glycoprotein produced by the cell or cell population, the frequency of CD52$^{hi}$ cells and/or the activity of CD52$^{hi}$ cells, and identifying the test agent as a potential therapeutic agent for the treatment or prevention of a disease or condition mediated by effector T-cell function, inflammation or sepsis, if the level of soluble CD52 glycoprotein, the frequency of CD52$^{hi}$ cells and/or the activity of CD52$^{hi}$ cells is increased after contact with the test agent.

The features of any embodiment described herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1: GAD65-specific CD4$^+$ suppressor T-cell clones display higher expression of CD52.
(A) Proliferation of a GAD65-specific T-cell clone in the presence of an autologous suppressor clone. GAD65 used was human recombinant glutamic acid decarboxylase 65. A fixed number (25,000) of GAD65-specific non-Treg clone (3.19) cells was co-cultured with increasing numbers of an autologous GAD65-specific Treg clone (1.4) in the presence or absence of GAD65 and irradiated PBMCs (100,000) as antigen presenting cells. $^3$H-thymidine uptake was measured after 72 hr. Results (mean±sem of triplicates) are representative of multiple autologous suppressor and non-suppressor clone pairs as previously described (Dromey et al., 2011). (B) Activated GAD65-specific suppressor clones have higher expression of CD52. Flow cytometric histograms of CD52 expression by autologous GAD65-specific suppressor (solid line) and non-suppressor (dashed line) clones following overnight stimulation by plate-bound anti-CD3 antibody. Staining by isotype control antibody is shown in grey. The result is representative of 3 clone pairs from 3 individuals.

FIGS. 2A-2D: High expression of CD52 is a marker of antigen-activated blood CD4$^+$ T-cells with suppressor function.

Figure 2A:
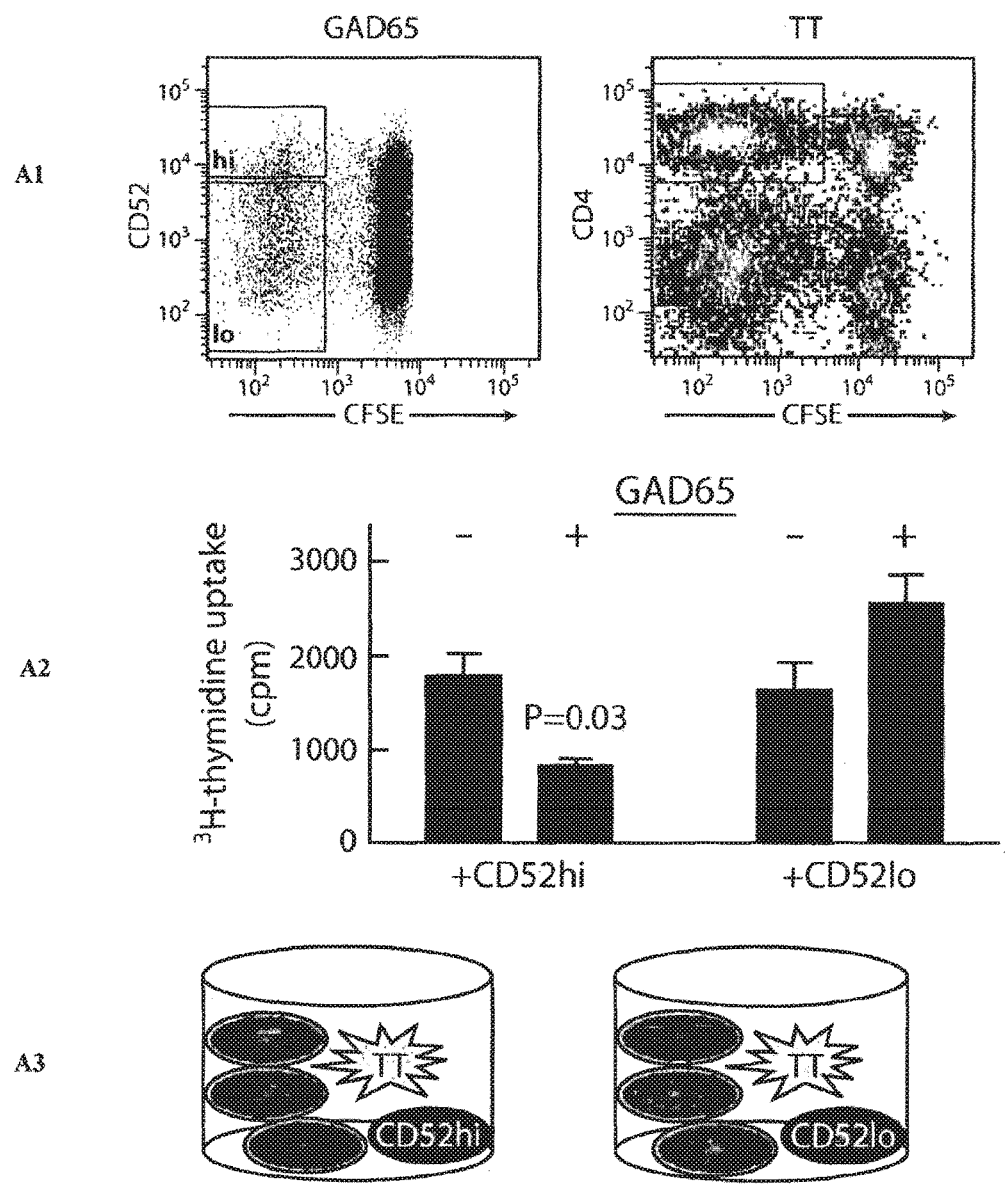

FIG. 2A. Proliferation of tetanus toxoid (TT)-stimulated, FACS-sorted CD4$^+$ T-cells re-activated with TT in the presence of GAD65-activated and sorted CD52$^{hi}$ or CD52$^{lo}$ CD4$^+$ cells. Activated CD4$^+$ cells were generated by incubating CFSE-labelled PBMCs with either GAD65 or TT for 7 days (A1). GAD65-activated CD52$^{hi}$ CD4$^+$ and CD52$^{lo}$ CD4$^+$ T-cells, and TT-activated CD4$^+$ T-cells, were then isolated by FACS. In the presence of GAD65, proliferation of cells re-activated by TT is suppressed by GAD65-activated CD52$^{hi}$ CD4$^+$ cells. 3H-thymidine uptake was measured over the last 16 h of a 3-day culture (A2). Results (mean±sem of triplicates) are representative of independent experiments on cells from 5 individuals.

Figure 2B:
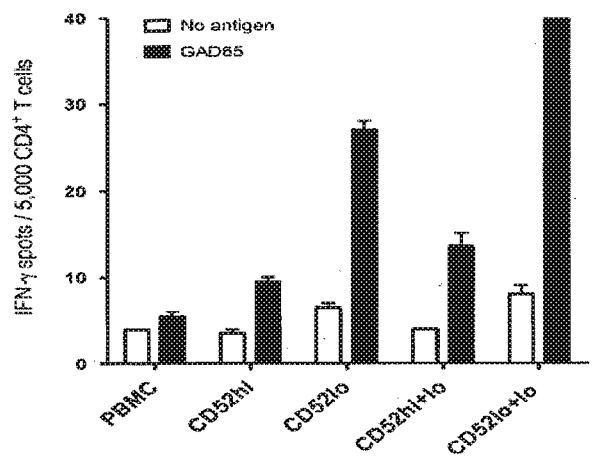

FIG. 2B. IFN-γ-secretion by GAD65-activated and sorted CD4$^+$ T-cells in the absence or presence of GAD65. CFSE-labelled PBMCs were incubated with GAD65 for 7 days and sorted into CD52$^{hi}$ and CD52$^{lo}$ CD4$^+$ T-cells. Sorted cells (5,000) were incubated in ELISpot plates with irradiated PBMCs (20,000). Results (mean+sem of triplicates) are representative of multiple independent experiments on cells from 5 individuals.

Figure 2C:
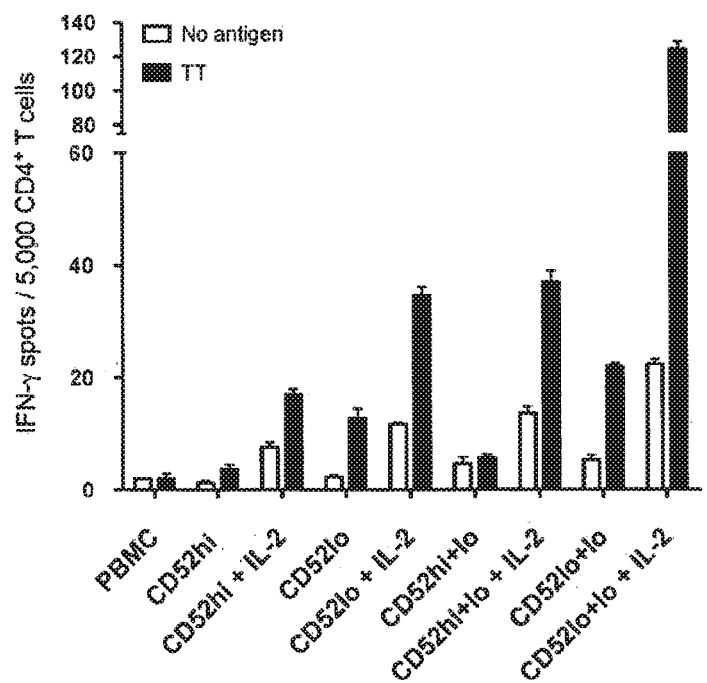

FIG. 2C. IFN-γ secretion by TT-activated and sorted CD4$^+$ T-cells in the absence or presence of TT±IL-2 (10 U/ml). As in FIG. 2B, except that CD52$^{hi}$ and CD52$^{lo}$ CD4$^+$ populations were sorted from CFSE-labelled PBMCs activated by TT. Results are mean+sem of triplicates.

Figure 2D:
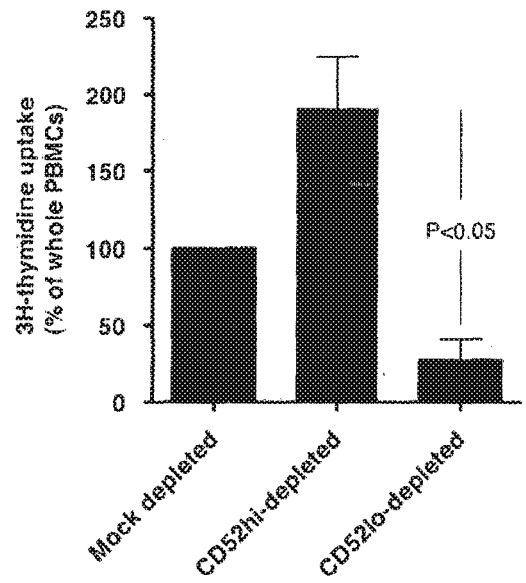

FIG. 2D. Proliferation of PBMCs initially depleted by FACS of either CD52$^{hi}$ or CD52$^{lo}$ CD4$^+$ cells before CFSE labelling and incubation in the absence or presence of GAD65 for 7 days. Results are representative of two experiments.

Figure 3:
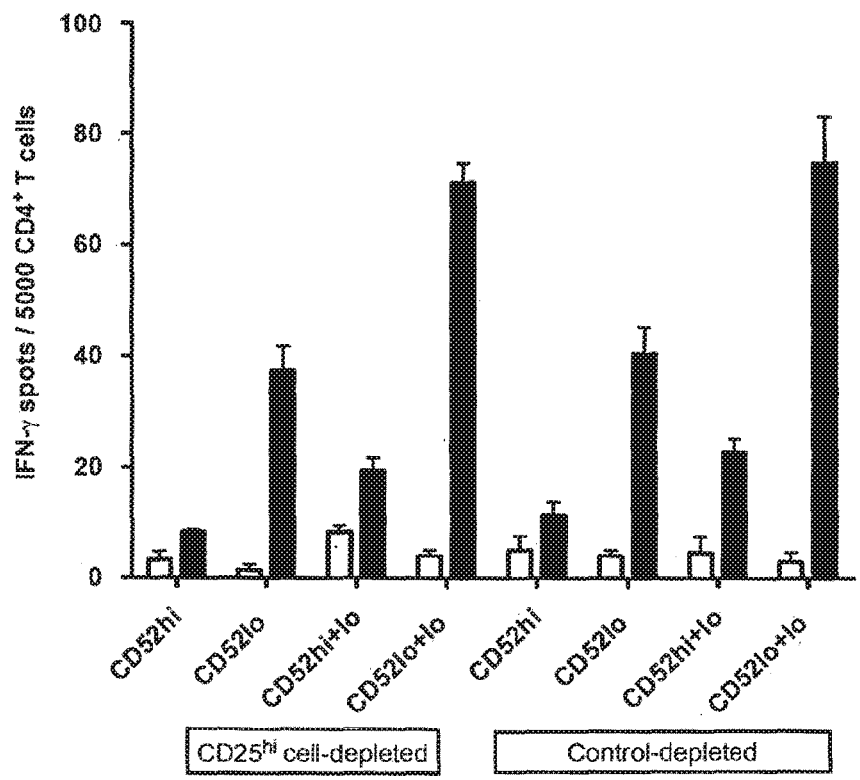

FIG. 3: CD4$^+$ CD52$^{hi}$ T-cells are not derived from resting CD4$^+$ CD25$^+$ T-cells. IFN-γ-secretion by TT-activated and sorted CD4$^+$ T-cells in the absence (open bars) or presence (filled bars) of TT, after initially depleting CD25$^{hi}$ cells from PBMCs.

Figure 4:
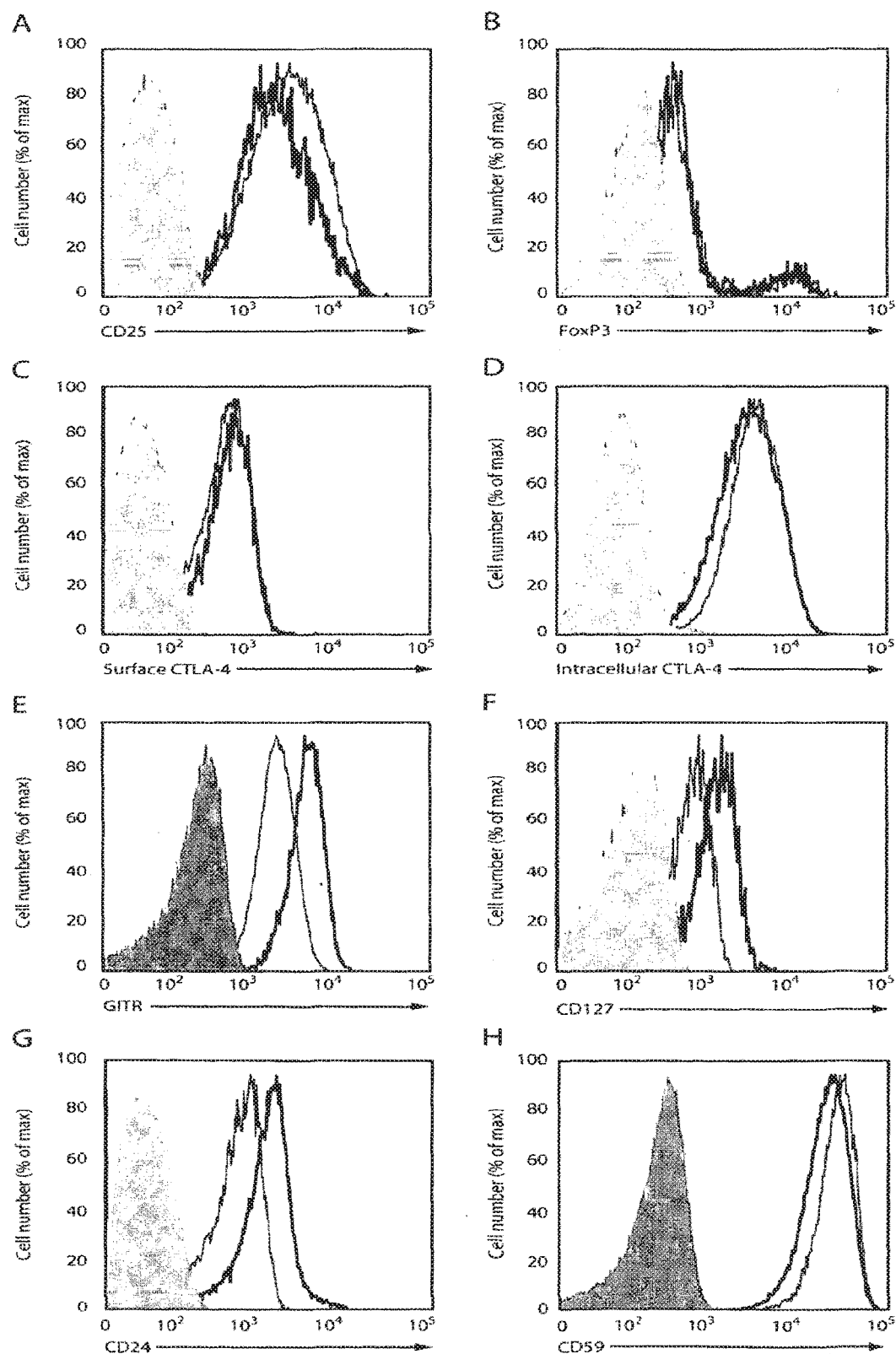

FIG. 4: Antigen-activated CD52$^{hi}$ CD4$^+$ T-cells are not distinguished by markers of conventional CD4$^+$ CD25$^+$ Treg cells.

Flow cytometric expression of (A) CD25, (B) FoxP3, (C) surface and (D) intracellular CTLA-4, (E) GITR, (F) CD127, (G) CD24 and (H) CD59 on divided CD52$_{hi}$ (black line) and CD52$^{lo}$ (grey line) CD4$^+$ T-cells, following incubation of PBMCs with TT for 7 days. Staining by isotype control antibody is shown as grey fill. Results are representative of 5 individuals.

Figure 5:
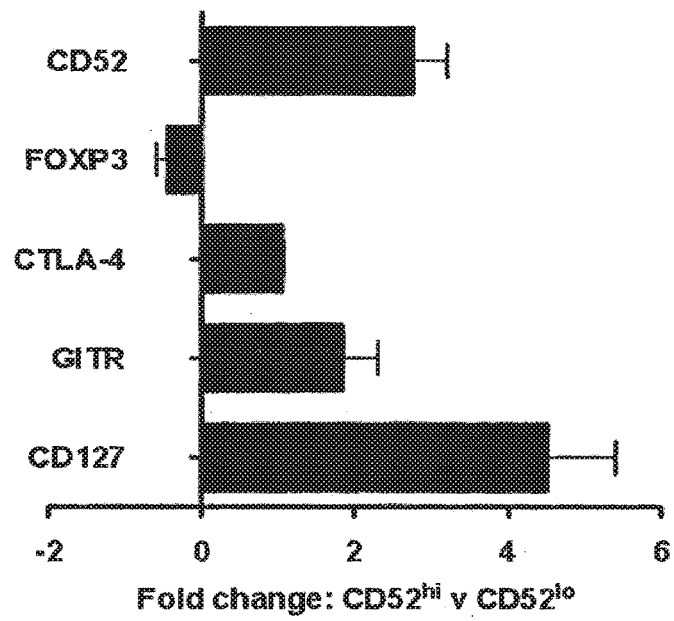

FIG. 5: CD52 gene expression is higher in CD52$^{hi}$ CD4$^+$ T-cells relative to CD52$^{lo}$ CD4$^+$ T-cells.

Expression of genes in CD52$^{hi}$ relative to CD52$^{lo}$ CD4$^+$ T-cells. Quantitative RT-PCR was performed in triplicate RNA samples extracted from sorted CFSE-labelled CD52$^{hi}$ and CD52$^{lo}$ CD4$^+$ T-cells from three individuals, 7 days after activation by GAD65. Results are expressed as median+interquartile range.

Figure 6:
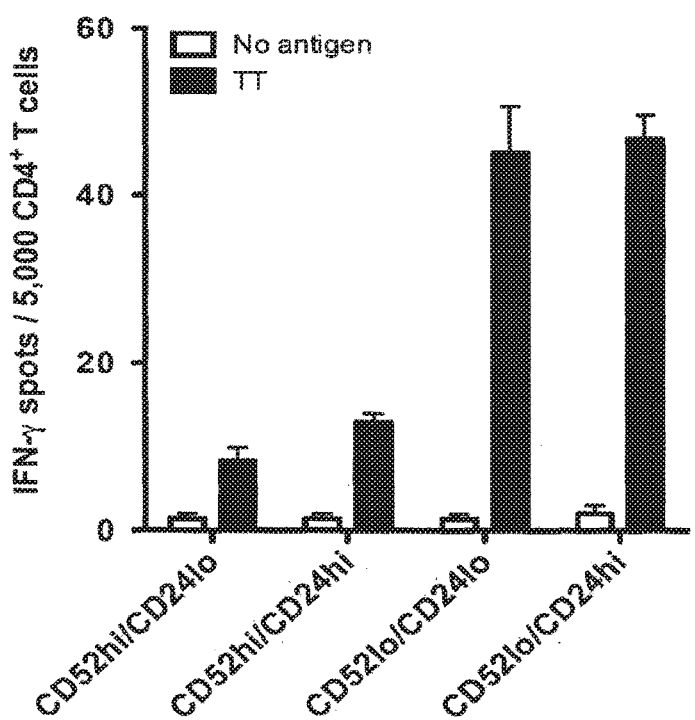

FIG. 6: CD24 expression does not delineate CD52$^{hi}$ CD4$^+$ T-cells with suppressor function.

IFN-γ secretion by TT-activated and sorted CD52$^{lo}$ CD4$^+$ T-cells re-stimulated with TT in the presence of TT-stimulated and sorted CD52 and CD24 subpopulations. Results are mean+sem of triplicates.

Figure 7:
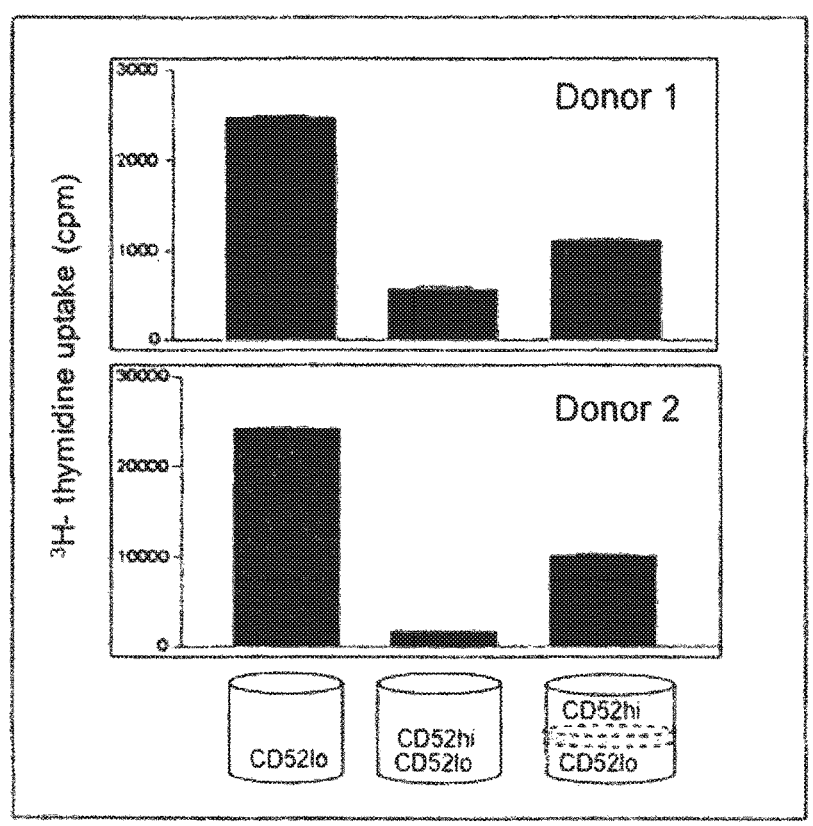

FIG. 7: Cell-cell contact is not required for suppression by CD52h CD4$^+$ T-cells.

FIGS. 8A-8B: Release of soluble CD52 accounts for suppression by CD52$^{hi}$ CD4$^+$ T-cells.

FIG. 8A. Immunoblotting of media conditioned by GAD65-activated CD52$^{hi}$ or CD52$^{lo}$ CD4$^+$ T-cells then re-activated by GAD65. CFSE-labelled PBMCs were incubated with GAD65 for 7 days and sorted into CD52$^{hi}$ and CD52$^{lo}$ CD4$^+$ T-cells. Sorted cells were re-activated with GAD65 and media collected after 24 hrs. Media were concentrated 10-fold, fractionated by SDS-PAGE, transferred to a PDVF membrane and blotted with a rabbit polyclonal antibody to CD52. The approximate molecular weight of native soluble CD52 is indicated.

FIG. 8B. Immunoblotting of media conditioned by TT-activated PBMCs+/−the phospholipase C inhibitor U73122. CFSE-labelled PBMCs were incubated with TT and media collected after 1 hr was processed as in (A).

Figure 8C:
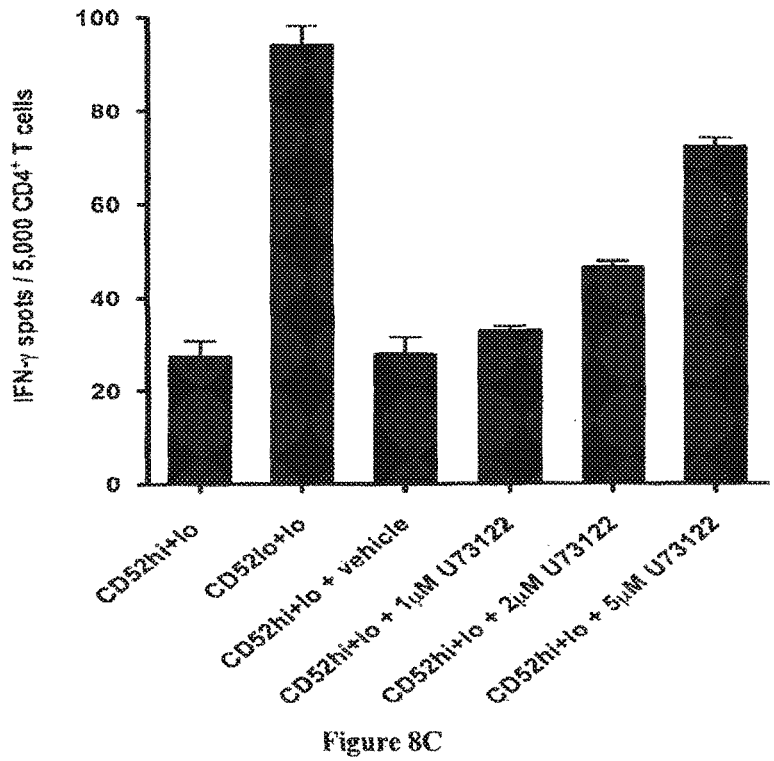

FIG. 8C. Effect of phospholipase C inhibitor on suppression by TT-activated CD52$^{hi}$ CD4$^+$ T-cells. CFSE-labelled PBMCs were incubated with TT for 7 days and sorted into CD52$^{hi}$ and CD52$^{lo}$ CD4$^+$ T-cells, which then were incubated together (5,000 of each) in ELISpot plates with irradiated PBMCs (20,000) and TT±the phospholipase C inhibitor U73122. Results are mean+sem of triplicates. There was no effect of U73122 in the absence of TT.

Figure 8D:
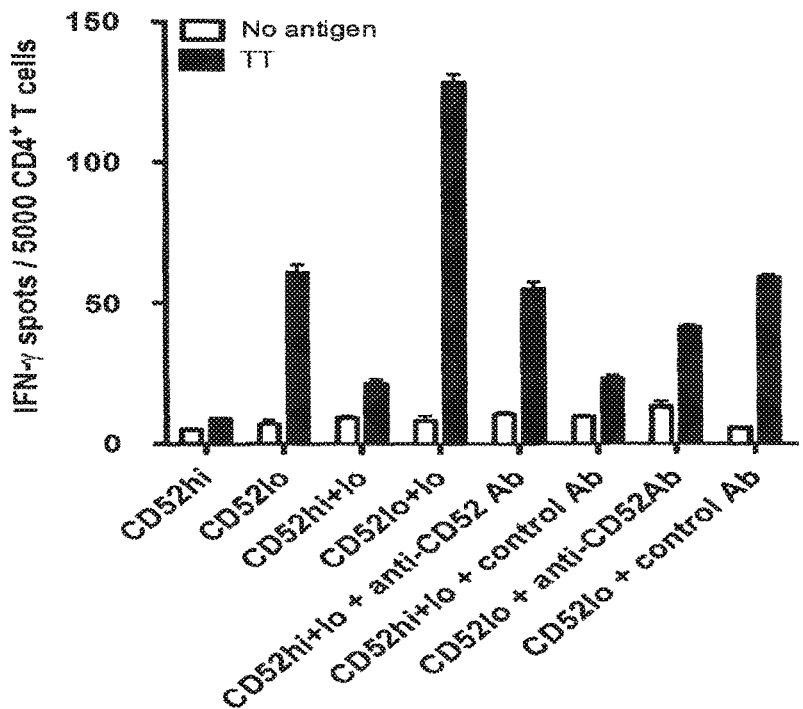

FIG. 8D. Effect of antibody to the carbohydrate moiety of CD52 on suppression by TT-activated CD52$^{hi}$ CD4$^+$ T-cells. Procedures were as in (C) except that cells in the ELISpot assay were incubated with or without TT and either 10 µg/ml anti-CD52 (CF1D12) or isotype control (IgG3) monoclonal antibody. Results (mean±sem) are representative of three independent experiments.

Figure 9A:
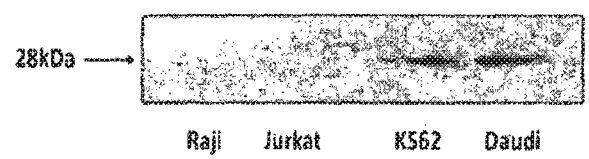
Figure 9B:
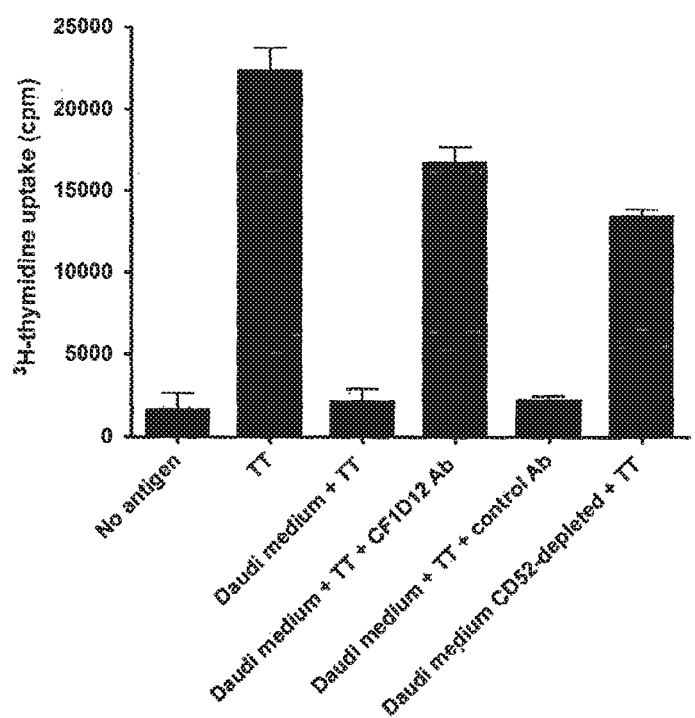

FIGS. 9A-9B: Soluble CD52 produced from Daudi cells directly suppresses T-cell proliferation and effector function.

FIG. 9A. Immunoblotting of media conditioned by cells lines. Media were concentrated 10-fold, fractionated by SDS-PAGE, transferred to a PDVF membrane and blotted with a rabbit polyclonal antibody to CD52.

FIG. 9B. Suppression of T-cell proliferation by Daudi cell conditioned medium. PBMCs (200,000 cells) were cultured for 7 days in IMDM containing 20% Daudi cell conditioned medium with TT and either anti-CD52 (CF1D12) or isotype control antibody (10 µg/mL). To deplete soluble CD52, Daudi medium was incubated overnight with rabbit anti-CD52 polyclonal antibody (1 µg/ml medium) followed by precipitation with protein G-Sepharose for 1 h at 4° C. Results (mean±sem) are representative of three independent experiments.

Figure 10:
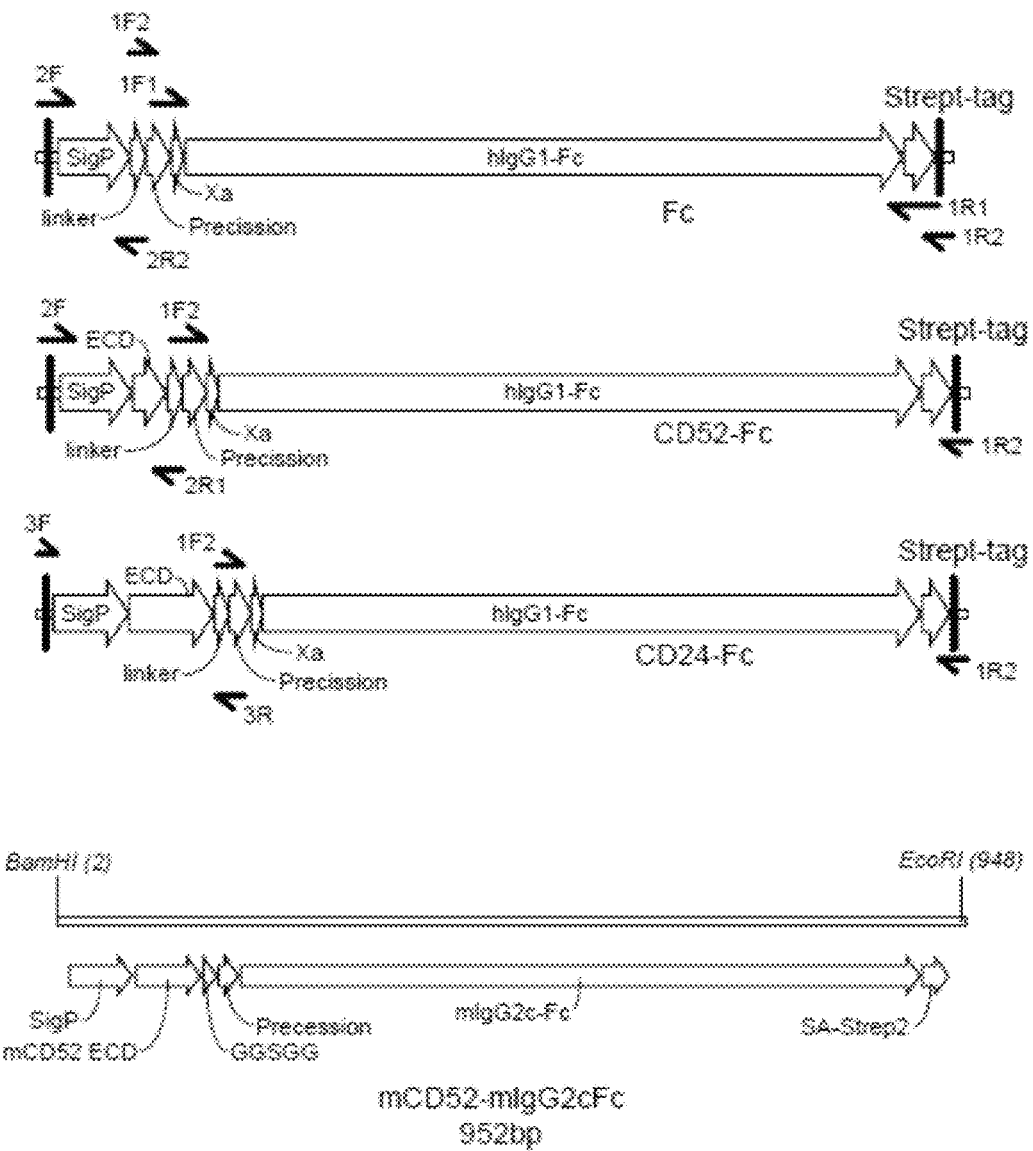

FIG. 10: DNA constructs for expression in lentivirus vector.

SigP=signal peptide; ECD=extracellular domain; Strep2=purification tag encoding 8 amino acids that binds to Strep-Tactin, a specifically engineered streptavidin.

FIGS. 11A-11D: Soluble CD52 fusion protein directly suppresses T-cell proliferation and effector function.

Suppression of T-cell proliferation by recombinant CD52-Fc. PBMCs (200,000) were cultured with TT for 7 days (FIG. 11A) and purified CD4+ T-cells (20,000) with anti-CD3 (100 ng/ml) and anti-CD28 (200 ng/ml) antibody for 48 hrs (FIG. 11B), with 4 times the number of irradiated PBMCs in 200 µl round bottom wells, in the presence of recombinant CD52-Fc or Fc protein control protein at the indicated concentrations. $^3$H-thymidine uptake was measured over the final 16 hrs of incubation. Results (mean±sem of triplicates) are representative of six independent experiments.

Figure 11A:
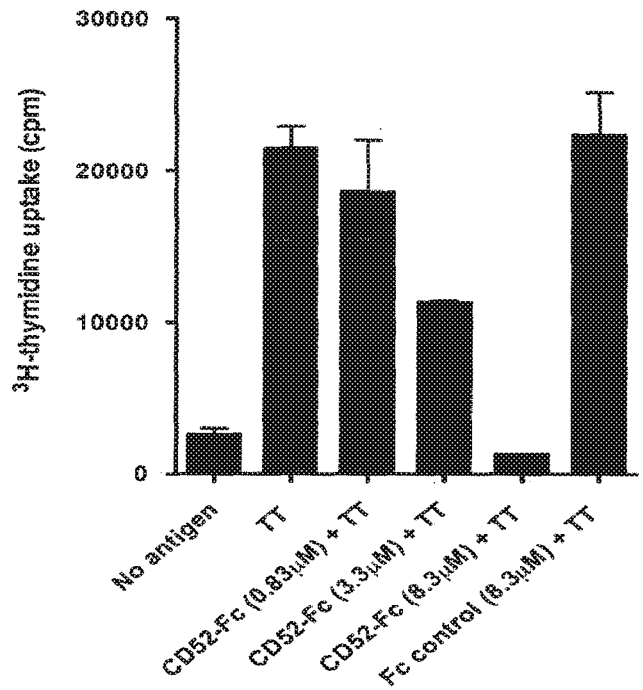
Figure 11B:
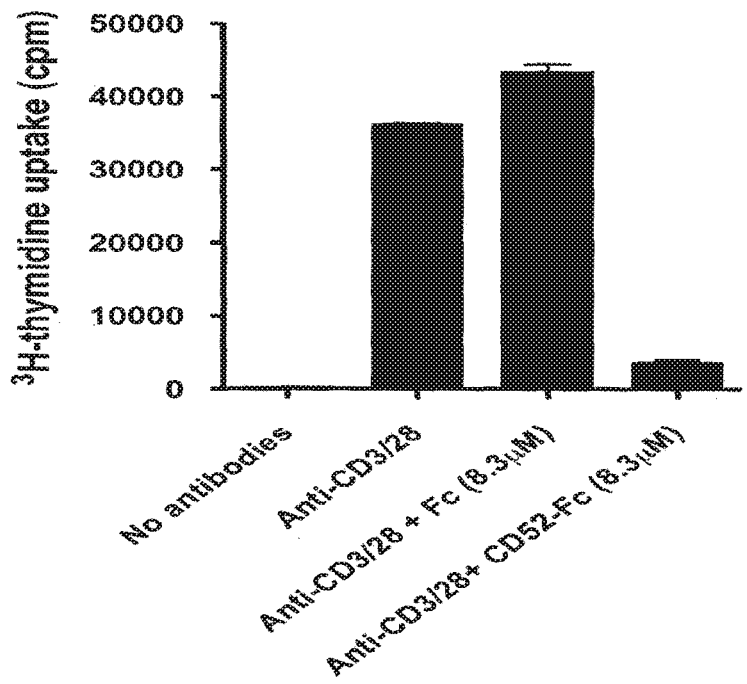
Figure 11C:
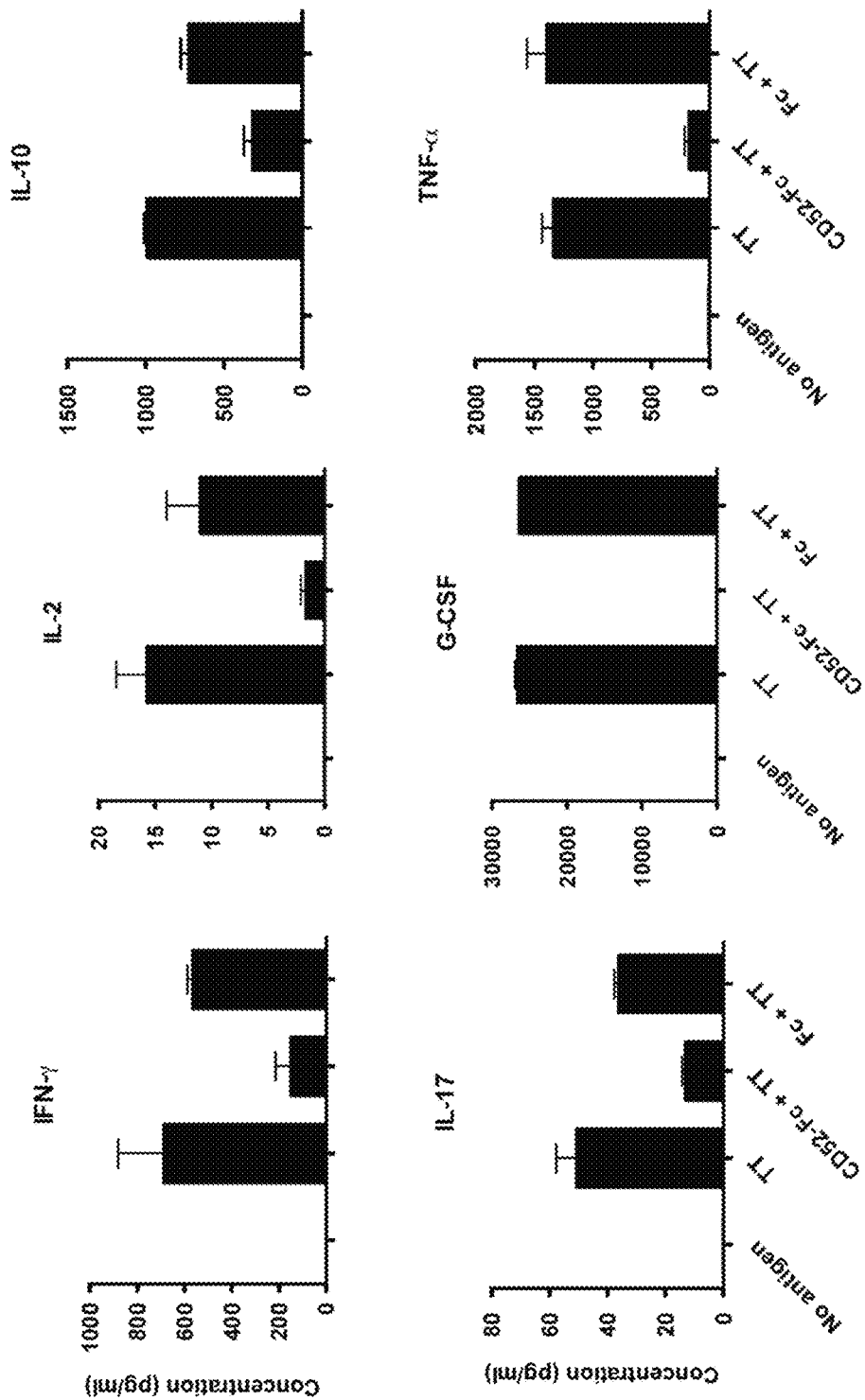

FIG. 11C. Suppression of cytokine secretion by recombinant CD52-Fc. Media from PBMCs activated with TT in (C)±3.3 µM CD52-Fc or Fc proteins were sampled after 48 hrs incubation and assayed for cytokines by multiplex bead array.

Figure 11D:
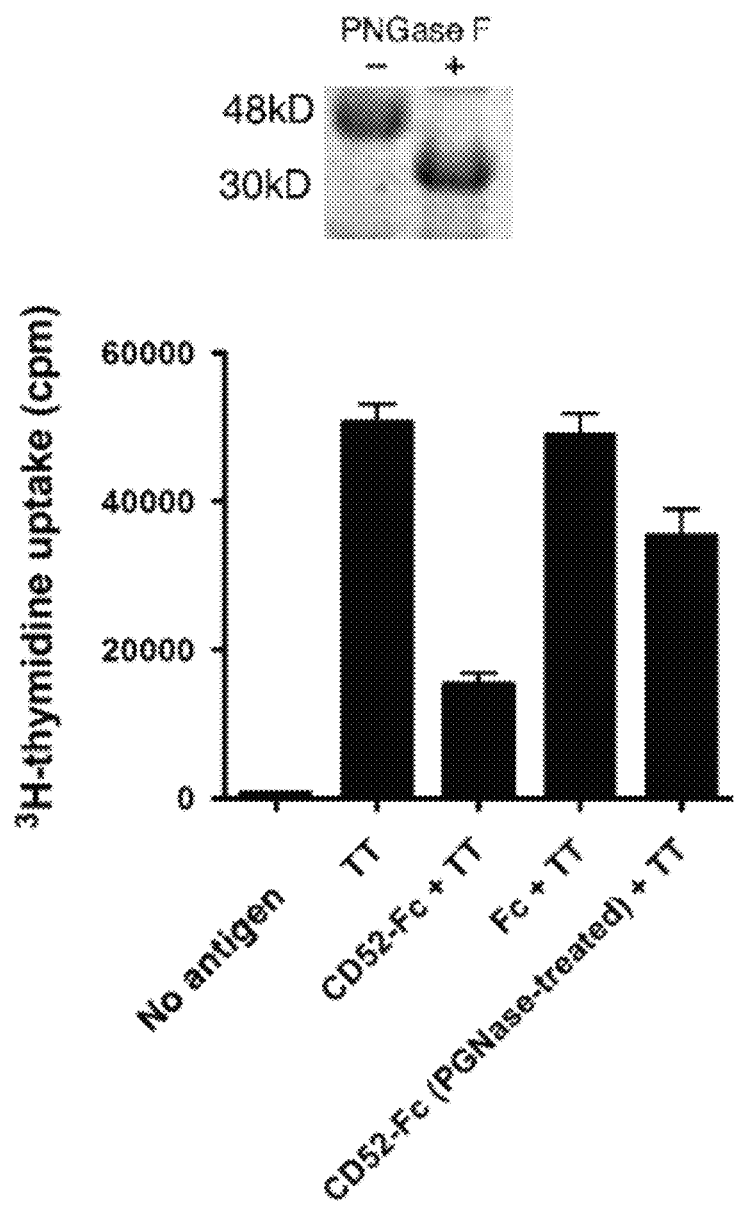

FIG. 11D. Impaired suppression by CD52-Fc after cleavage of N-linked carbohydrate. CD52-Fc (20 µg) was incubated with or without PNGase F (1,000 units) in 20 µl PBS for 1 h at 37° C., and the reaction terminated by heating at 75° C. for 10 min PBMCs incubated with TT and treated or untreated CD52-Fc (final 2.5 µM) for 7 days at 37° C., and 3H-thymidine uptake then measured as in (FIG. 11C). Upper panel shows the determination by SDS-PAGE and Coomassie staining of the decrease in size of CD52-Fc after PNGase F treatment.

FIGS. 12A-12E: CD52 carbohydrate binding to Siglec-10 is required for soluble CD52 effector function.

Figure 12A:
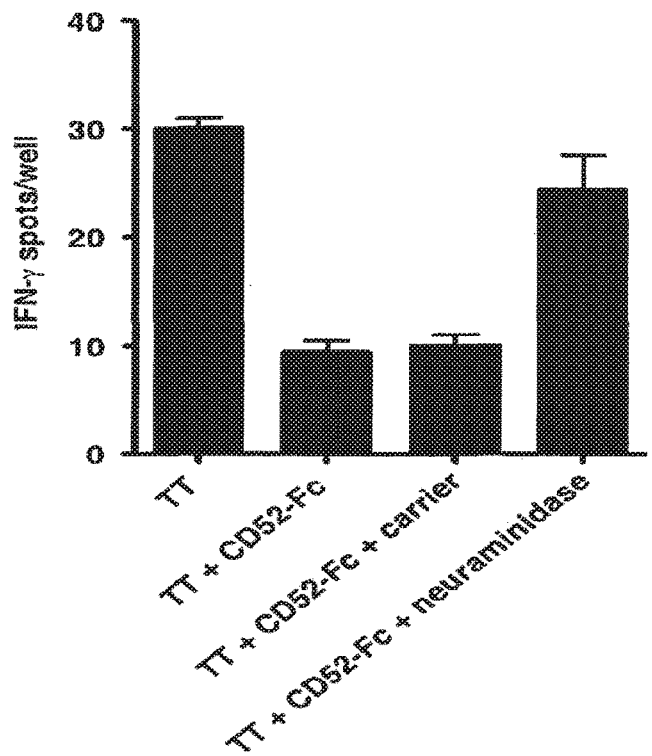

FIG. 12A. Suppression of T-cell activation by CD52-Fc±treatment with neuraminidase. CD52-Fc (3.3 µM) was incubated with neuraminidase (1 unit) or carrier buffer only in 20 µl for 30 min at 37° C. PBMCs were then incubated with TT±neuraminidase-treated or untreated CD52-Fc (final 0.33 µM) in a 48-well plate for 1 h at 37° C. before non-adherent cells were transferred to an ELISpot plate and developed after 24 h at 37° C. for IFN-γ spots.

Figure 12B:
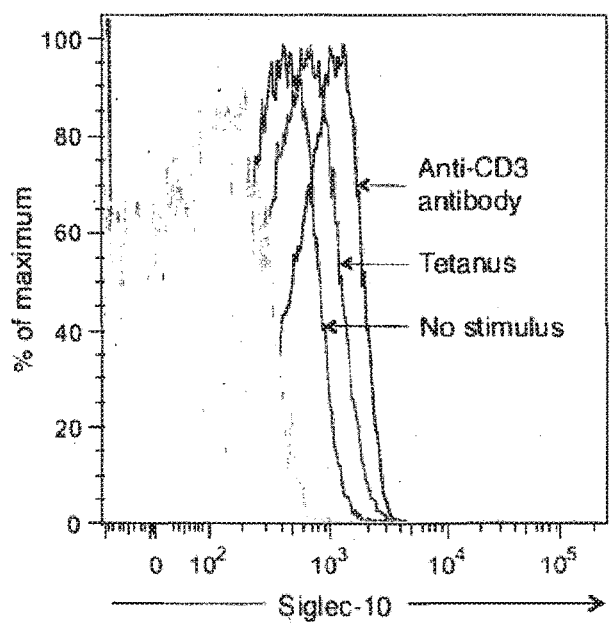

FIG. 12B. Siglec-10 expression on human T-cells after T-cell activation. Flow cytometric histograms of Siglec-10 expression on CD4+ T-cells after incubation of PBMCs with TT or soluble anti-CD3 antibody for 4 days.

Figure 12C:
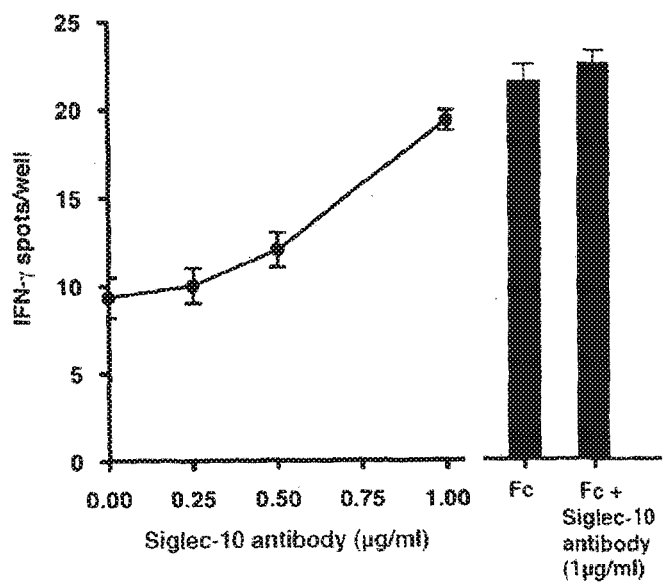

FIG. 12C. Suppression of T-cell function by CD52-Fc when co-incubated with anti-Siglec-10 antibody. PBMCs were incubated in an ELISpot plate with TT and CD52-Fc (3.4 µM) and different concentrations of affinity-purified goat antibody to the extracellular domain of Siglec-10, or Fc (0.34 µM)±antibody before non-adherent cells were transferred to an ELISpot plate for 24 h for development of IFN-γ spots.

Figure 12D:
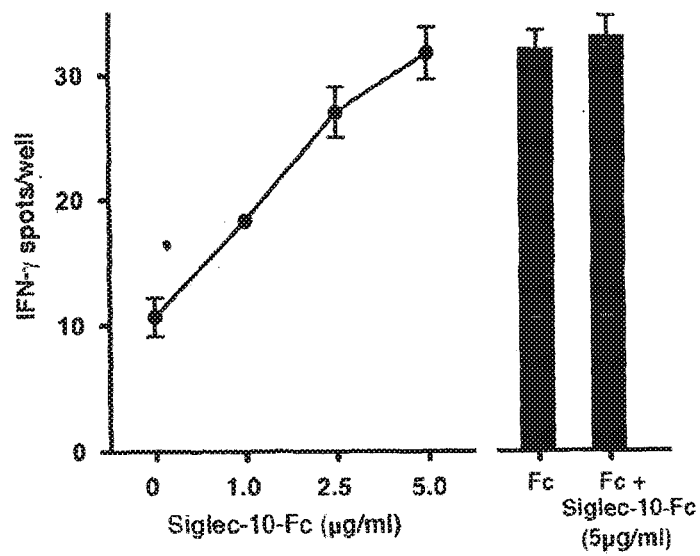

FIG. 12D. Suppression of T-cell function by CD52-Fc when co-incubated with soluble recombinant Siglec-10-Fc. PBMCs were incubated in a 48-well plate with TT and CD52-Fc (3.4 µM) and different concentrations of recombinant Siglec-10-Fc before non-adherent cells were transferred to an ELISpot plate for 24 hrs for development of IFN-γ spots.

Figure 12E:
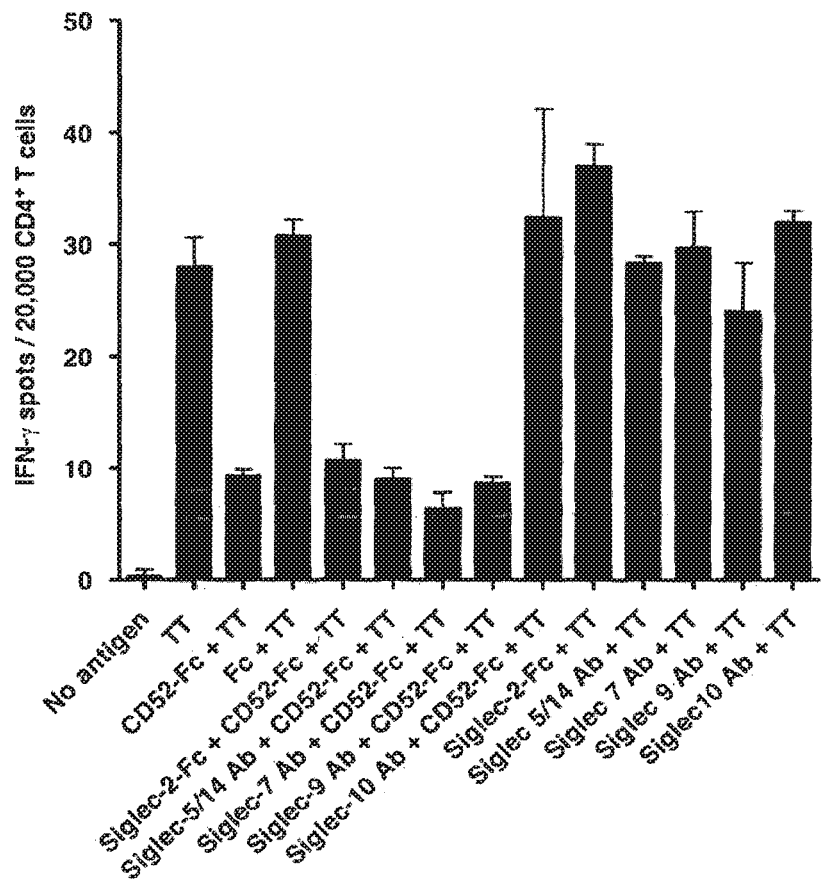

FIG. 12E. Blockade of Siglec-10 but not other Siglecs reduces T-cell suppression by CD52-Fc. CD4+ T-cells (20,000) were incubated in triplicate ELISpot plate wells at 37° C. with TT, together with CD52-Fc or Fc (3.4 µM each) and anti-human Siglec antibodies (10 µg/ml each) or recombinant human Siglec 2-Fc (20 µg/ml), as indicated. After 20 hrs, wells were washed and developed for IFN-γ spots.

Figure 13:
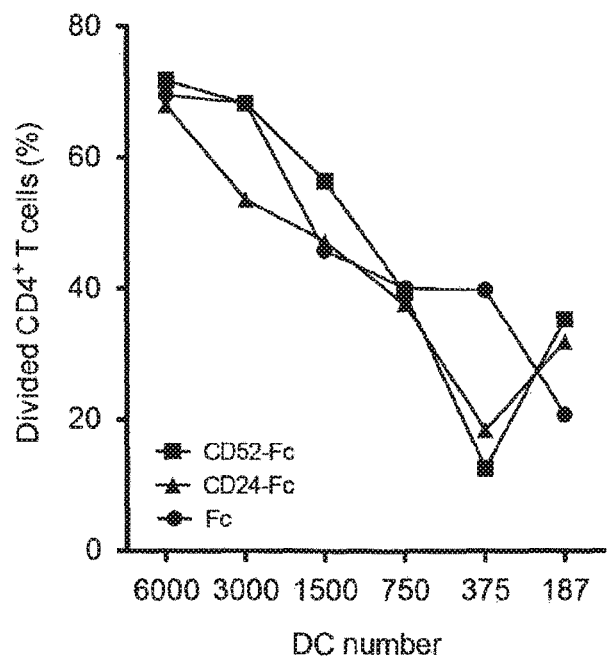

FIG. 13: CD52-Fc does not affect the T-cell stimulatory capacity of purified blood dendritic cells.

FACS-sorted human blood CD1b/c+ DC were pre-incubated with CD52-Fc or Fc protein, washed twice and co-cultured with allogeneic CFSE-labeled CD4+ T-cells for 6 days. The frequency of dividing CD4+ T-cells identified as CFSE$^{lo}$ was determined by flow cytometry. The result is representative of two independent experiments with different donors. Similar results were obtained for CD304+ plasmacytoid DC and for CD14+ monocytes (data not shown).

Figure 14:
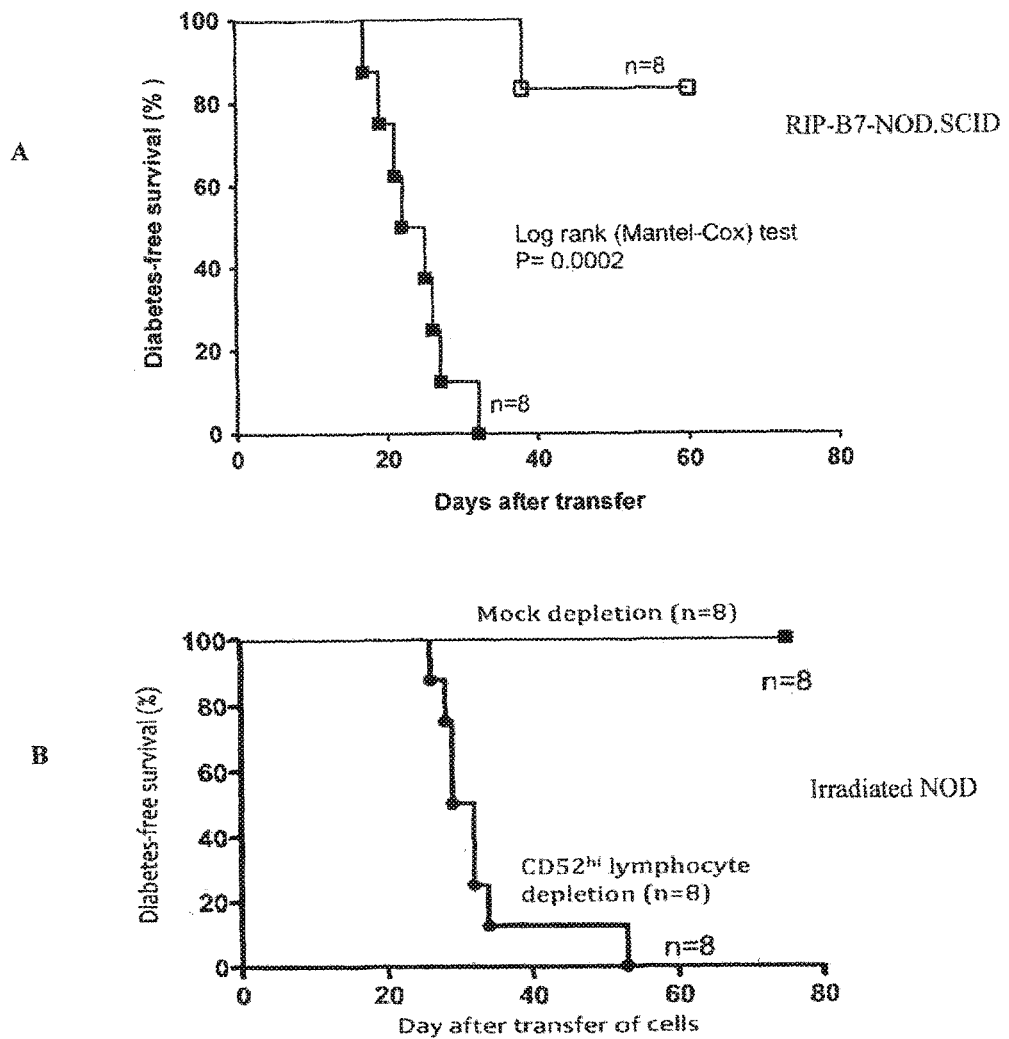

FIG. 14: Transfer of CD52$^{hi}$-depleted splenocytes induces rapid onset of diabetes in NOD. SCID mice.

Total splenocytes from wild-type NOD mice depleted or sham depleted of CD52$^{hi}$ cells were injected iv into (A) 8 week-old RIP.B7/NOD.SCID mice (2×10$^6$ cells) and (B) irradiated (750 rad) 8 week-old male NOD mice (1.2×10$^7$ cells). Mice were monitored by measuring urine glucose twice weekly using Diastix (Bayer) and diabetes confirmed by a blood glucose measurement >14 mM on consecutive days. Results show percentage survival over time after transfer of the respective cell populations.

Figure 15:
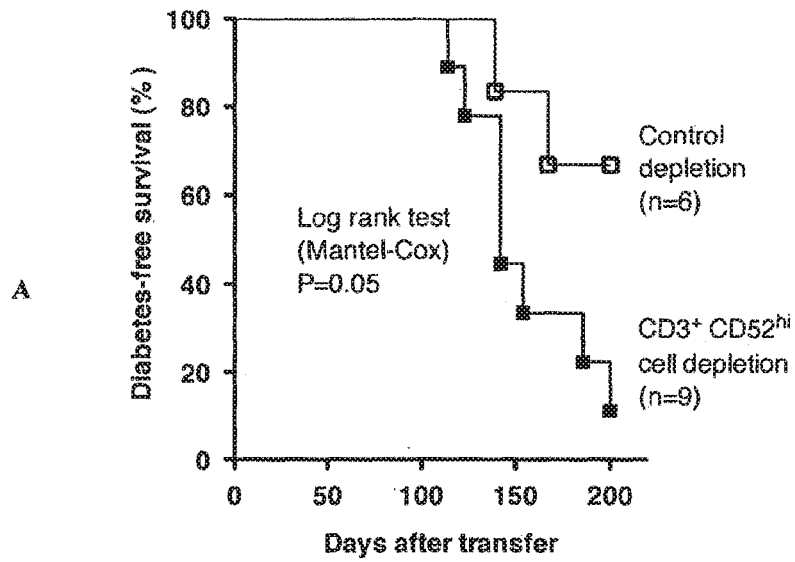
Figure 15:
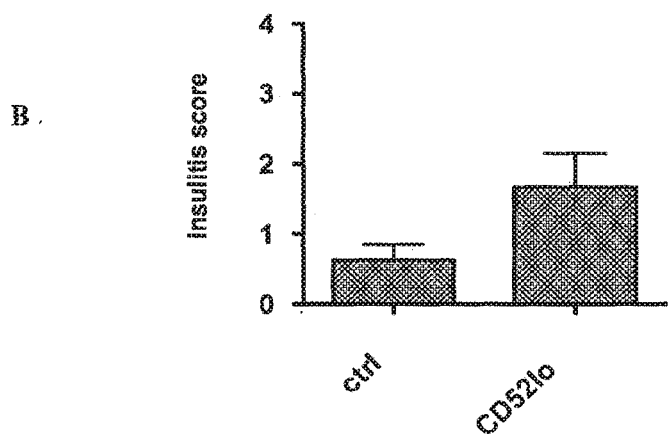

FIG. 15: CD52$^{hi}$-depleted CD3+ T-cells accelerate onset of diabetes in irradiated NOD mice.

Irradiated (750 rad) 8 week-old male NOD mice were injected with 1.2×10$^7$ splenocytes or CD3+CD52$^{hi}$ depleted splenocytes derived from 10 week-old non-diabetic female NOD mice. Mice were monitored by measuring urine glucose twice weekly using Diastix (Bayer) and diabetes confirmed by a blood glucose measurement >14 mM on consecutive days. Results show (A) percentage survival over time after transfer of the respective cell populations and (B) insulitis score (n=4/group) after 4 weeks.

Figure 16:
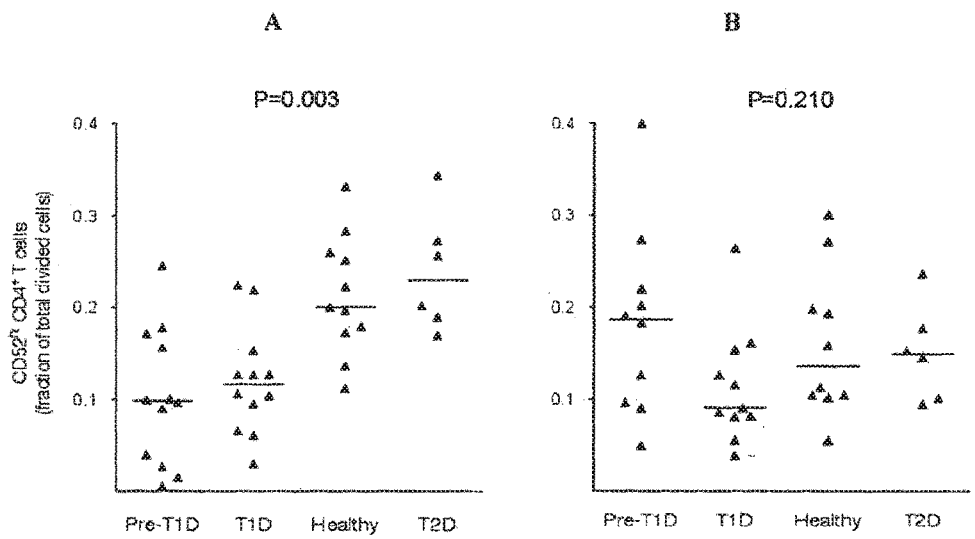

FIG. 16: The frequency of CD52$^{hi}$ CD4+ T-cells generated in response to simulation by GAD65 is impaired in type 1 diabetes.

The proportion of CD52$^{hi}$ CD4+ T-cells expanded from PBMCs in response to (A) GAD65 and (B) TT is shown for individuals in the following categories: Pre-T1D—at risk for type 1 diabetes; T1D—with type 1 diabetes; Healthy—disease-free HLA DR3 and/or DR4 young adults; T2D—type 2 diabetes. The horizontal bar is the median for each group. Overall P values for analysis of variance shown were determined by the Kruskal-Wallis test; Dunn's multiple comparison test then revealed significant differences between both Pre-T1D and T1D compared Healthy or T2D at P<0.05.

Figure 17:
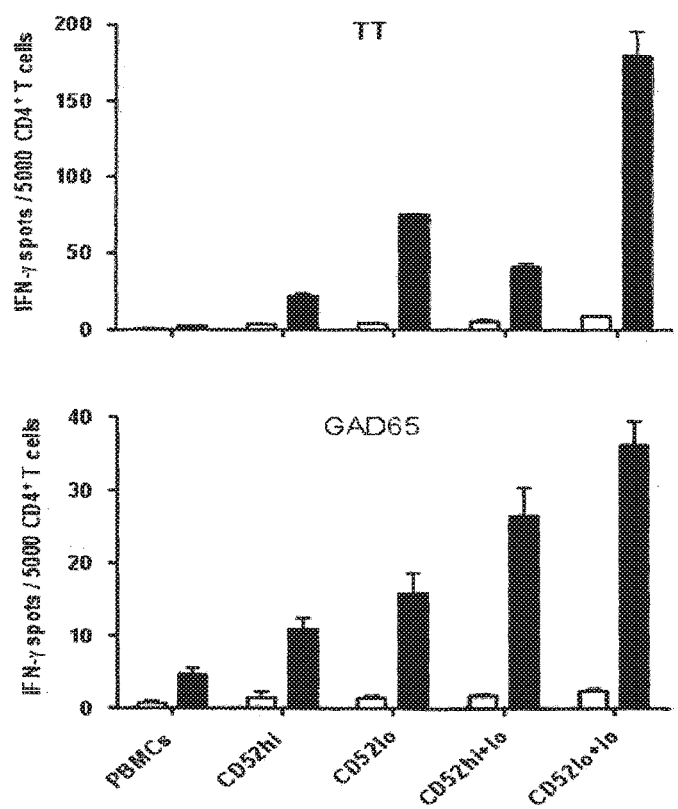

FIG. 17: Suppression by CD52$^{hi}$ CD4+ cells generated in response to GAD65 is impaired in pre-clinical T1D.

IFN-γ-secretion by TT- or GAD65-activated and sorted CD4+ T-cells in the absence (open) or presence (filled) of the antigen. Results (mean+sem of triplicates) are representative of experiments on cells from six individuals with islet cell autoantibodies at risk for type 1 diabetes.

Figure 18:
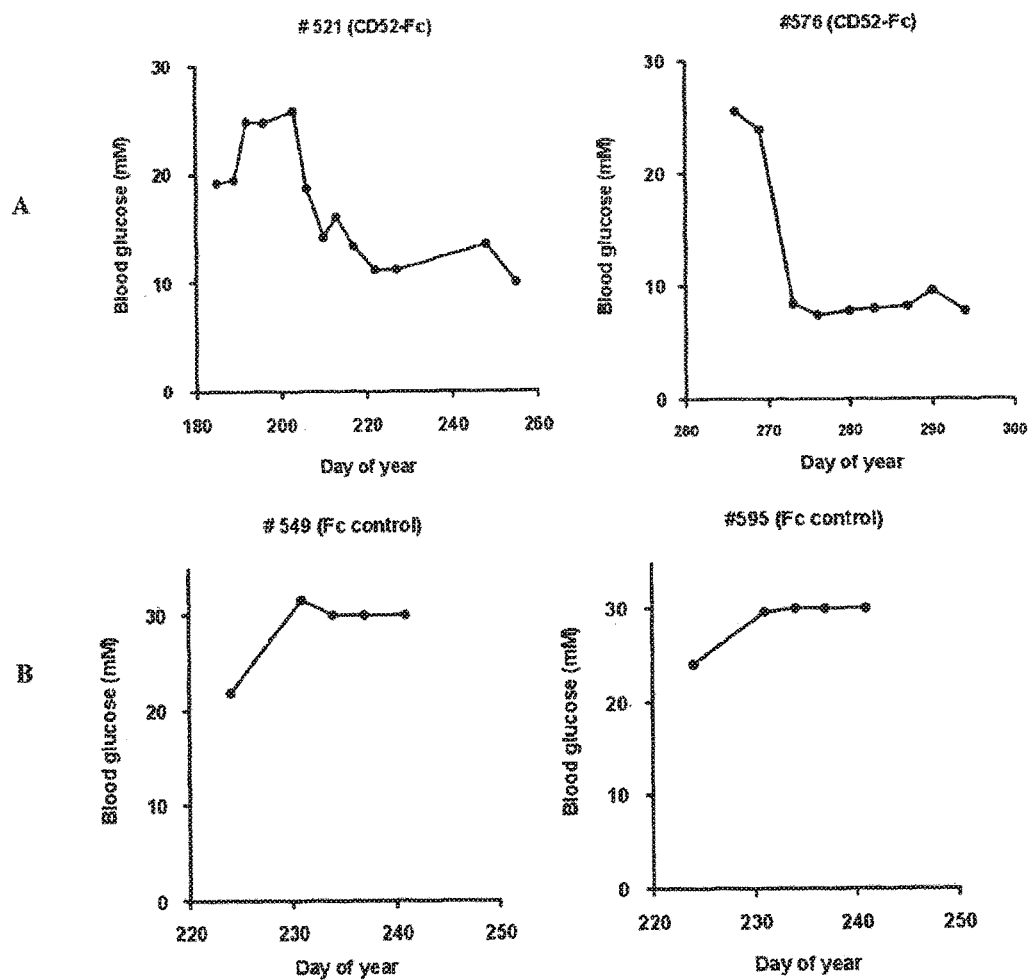

FIG. 18: Treatment with CD52-Fc reverses hyperglycemia in NOD mice with recent-onset diabetes.

Blood glucose levels in female NOD mice were monitored by weekly testing for urine glucose and diabetes was diagnosed in mice with a positive urine test by a blood glucose concentration >14 mM. As soon as hyperglycemia was confirmed mice were given either CD52-Fc or Fc, 20 µg i.p., six doses on alternate days, and their blood glucose concentrations then monitored twice weekly. Results are shown for two pairs of mice that received either CD52-Fc (A) or Fc control (B).

Figure 19:
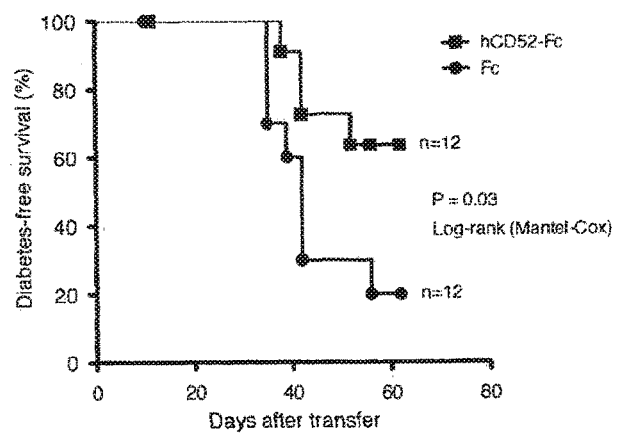

FIG. 19: Development of diabetes in NOD.SCID mice after transfer from diabetic NOD mice of splenocytes treated ex vivo with hCD52-Fc or Fc.

Recombinant human CD52 Fc- or Fc-treated diabetic NOD splenocytes were injected into NOD.SCID mice. Splenocytes from female diabetic mice were isolated and incubated with either recombinant hCD52-Fc or Fc protein in 'CD52 buffer'. Cells were re-suspended and injected into male NOD.SCID mice (6 per group; see ☐ ethods Example 18).

Figure 20:
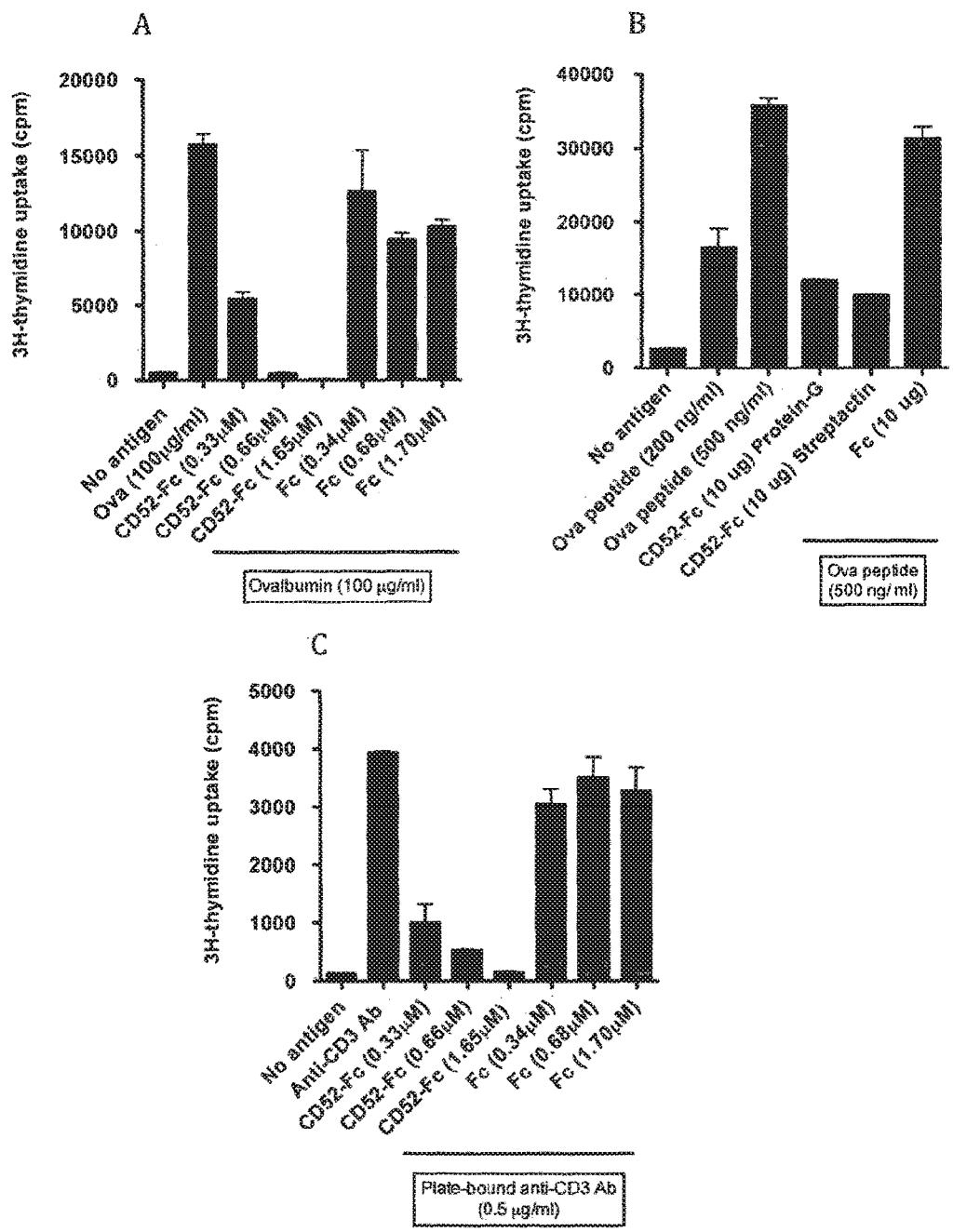

FIG. 20: Human CD52-Fc suppresses proliferation of mouse ovalbumin (Ova)-specific TCR transgenic CD4 (OT-II) T-cells.

Splenocytes (1×10$^5$) from 10 week-old female OT-II mice were incubated for 3 days in round bottom 96-well plates in 200 ml RPMI-1640 medium containing 5% FCS and the indicated concentrations of ova protein (A) or peptide (B), or anti-CD3 antibody (clone 2C-11) (C), and recombinant human CD52-Fc or Fc protein. $^3$H-thymidine uptake was measured over the last 16 h of culture. Results are mean±sem of triplicates.

Figure 21:
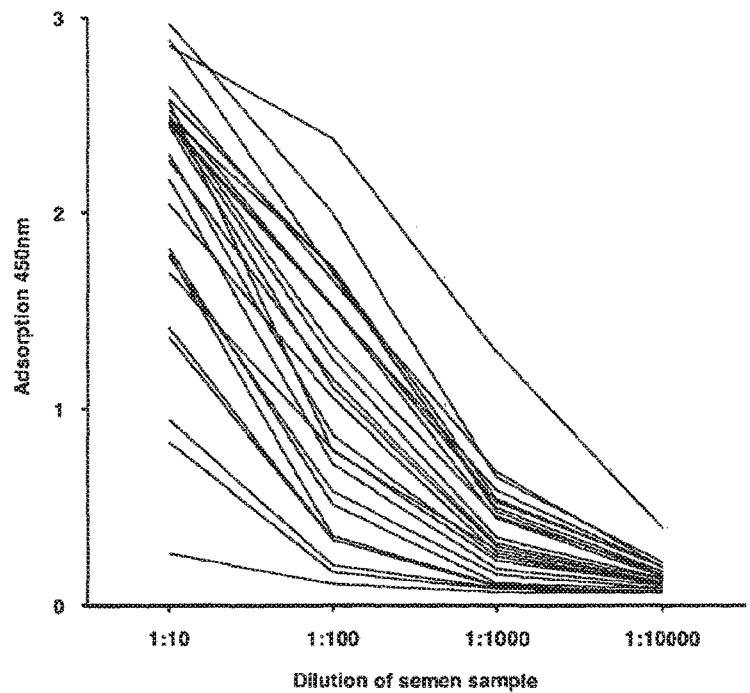

FIG. 21: Identification by ELISA of CD52 in human semen samples.

Absorbance at 450 nm is shown for soluble CD52 in serial dilutions of semen samples (n=26).

Figure 22:
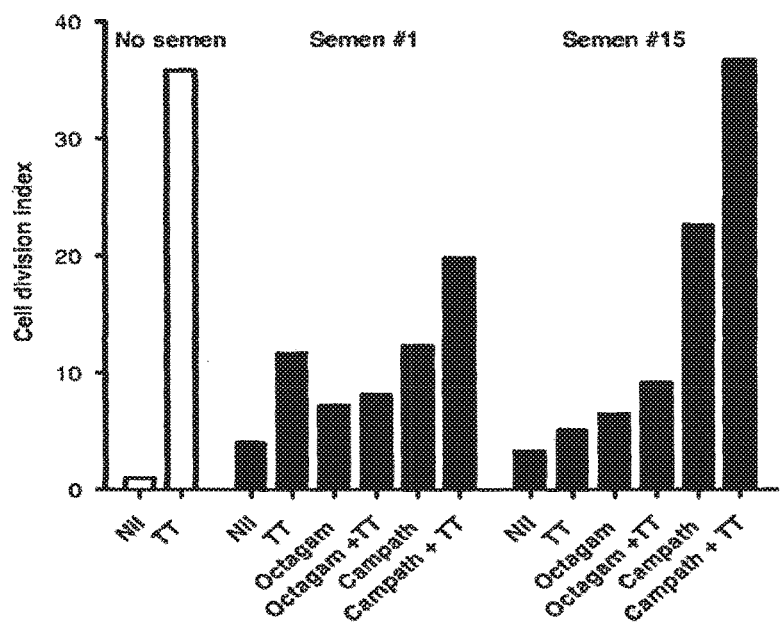

FIG. 22: Semen-derived CD52 suppresses human T-cell proliferation.

The effect on T-cell proliferation (Cell Division Index; CDI) calculated from CFSE dye dilution in response to tetanus toxoid (TT, 5 Lfu/ml) is shown for two semen samples (at a dilution of 1:20) without immunodepletion or depleted with control IgG ('Octagam') or anti-CD52 IgG (Campath).

Figure 23:
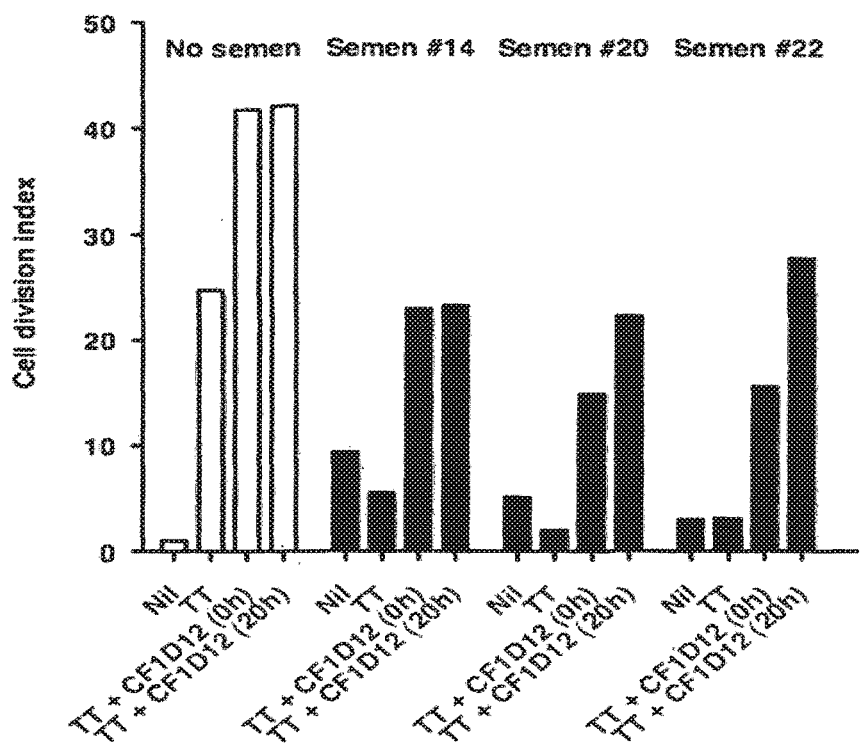

FIG. 23: T-cell proliferation (CFSE dye dilution) to tetanus toxoid: effect of semen±blocking antibody to CD52.

The effect on T-cell proliferation (CDI, calculated from CFSE dye dilution) in response to tetanus toxoid (TT, 5 Lfu/ml) is shown for semen samples (1:20)±blocking antibody CF1D12 (20 µg/ml).

Figure 24:
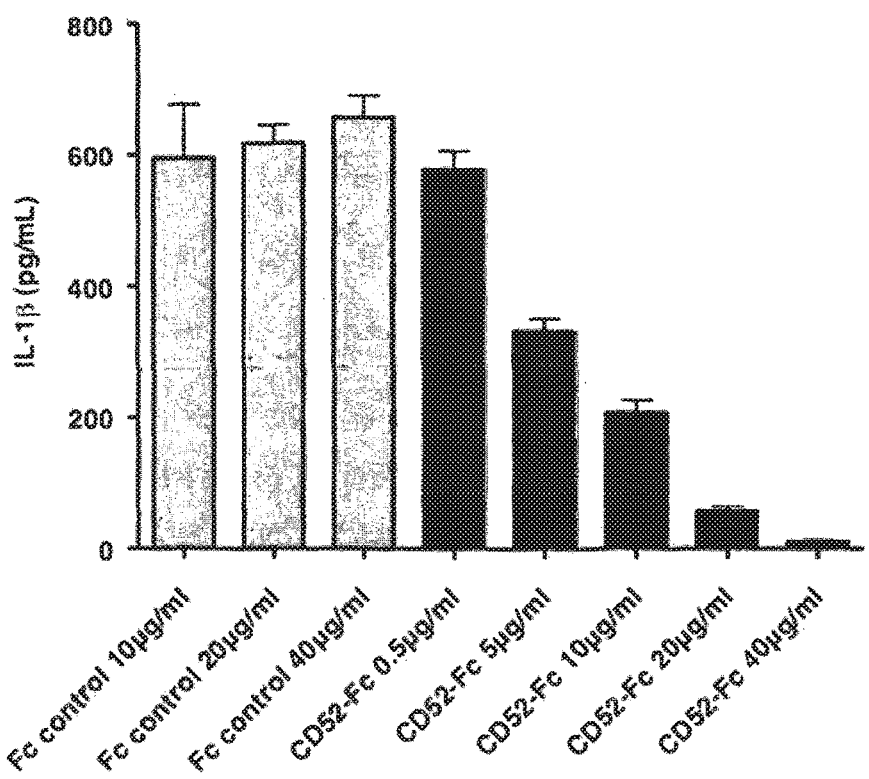

FIG. 24: hCD52-Fc suppresses IL-1β secretion by THP1 cells in response to LPS. THP-1 cells were incubated with different doses of CD52-Fc or Fc control in presence of LPS, medium collected and the concentration of IL-1β measured by ELISA.

Figure 25:
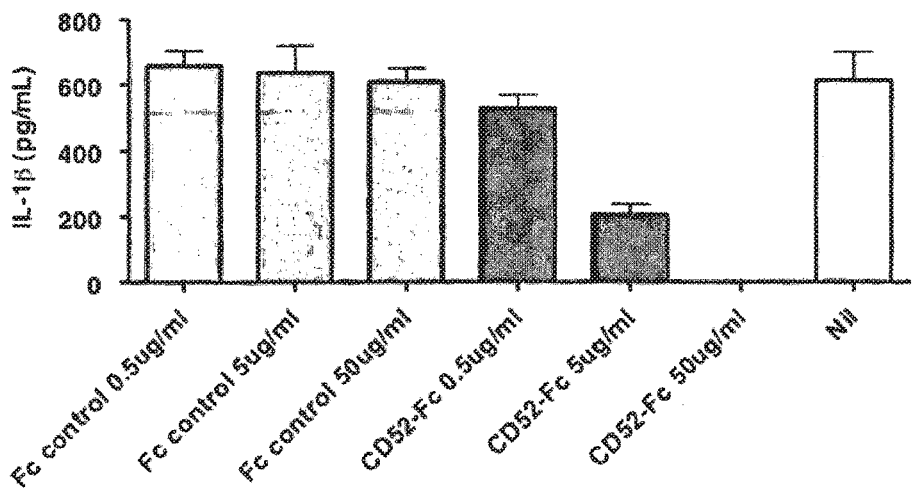

FIG. 25: hCD52-Fc suppresses IL-1β secretion by THP1 cells in response to Pam3CSK.

THP-1 cells were incubated with different doses of CD52-Fc or Fc control in presence of the TLR-2 agonist Pam3CSK, media collected and the concentration of IL-1β measured by ELISA.

Figure 26:
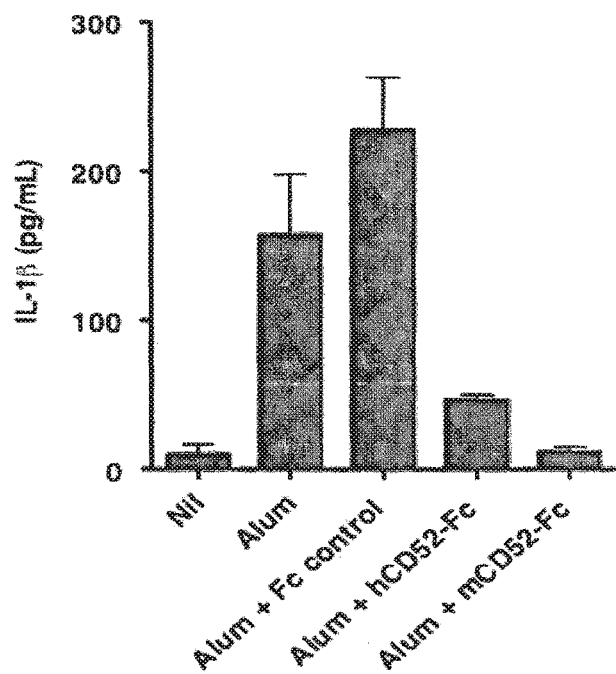

FIG. 26: hCD52-Fc (50 µg/ml) suppresses IL-1β secretion by differentiated THP1 cells in response to alum.

THP-1 cells were differentiated with phorbol-12-myristate-13-acetate (PMA), washed and incubated with CD52-Fc or Fc control. Medium was collected and the concentration of IL-1β measured by ELISA.

Figure 27:
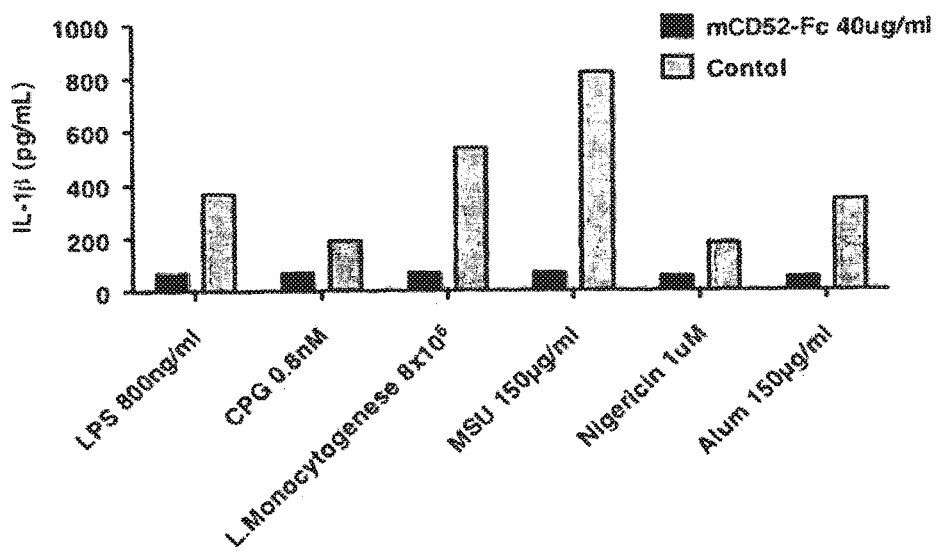

FIG. 27: mCD52-Fc suppresses secretion of IL-1β by mouse bone marrow-derived dendritic cells in response to a range of innate immune stimuli.

Bone marrow-derived dendritic cells (BMDCs) from C57/B6 mice were incubated with mouse CD52-Fc or PBS (Control) in presence of LPS, CPG or *Listeria monocytogenes*, primed with LPS and then stimulated with the known inflammsome agonists, monosodium urate (MSU), alum and nigericin. Cytokine concentrations in the media were measured by multiplex cytokine array assay.

Figure 28:
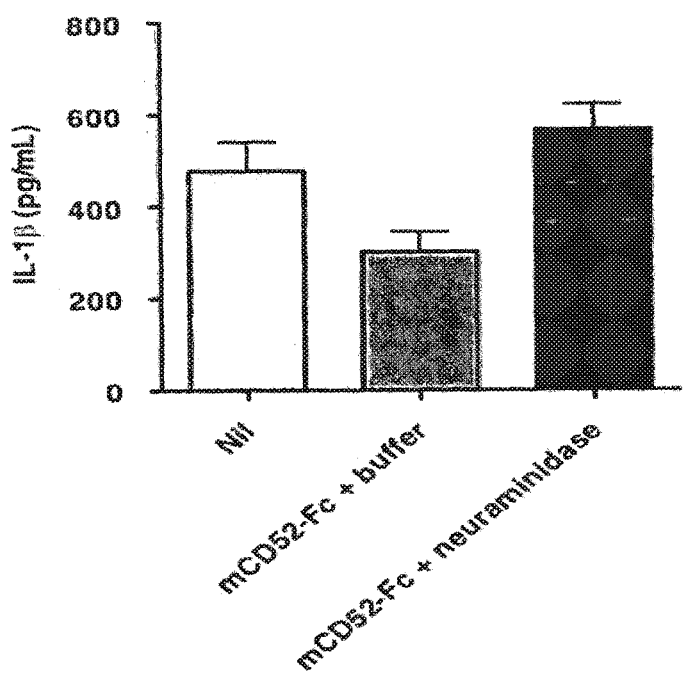

FIG. 28: Treatment with *A. ureafaciens* neuraminidase abolishes the suppressive effect of mCD52-Fc on LPS-induced IL-1β production by THP-1 cells.

THP-1 cells were incubated with neuraminidase- or reaction buffer-treated mCD52-Fc in presence of LPS. Media were collected and the concentration of IL-1β measured by ELISA.

Figure 29:
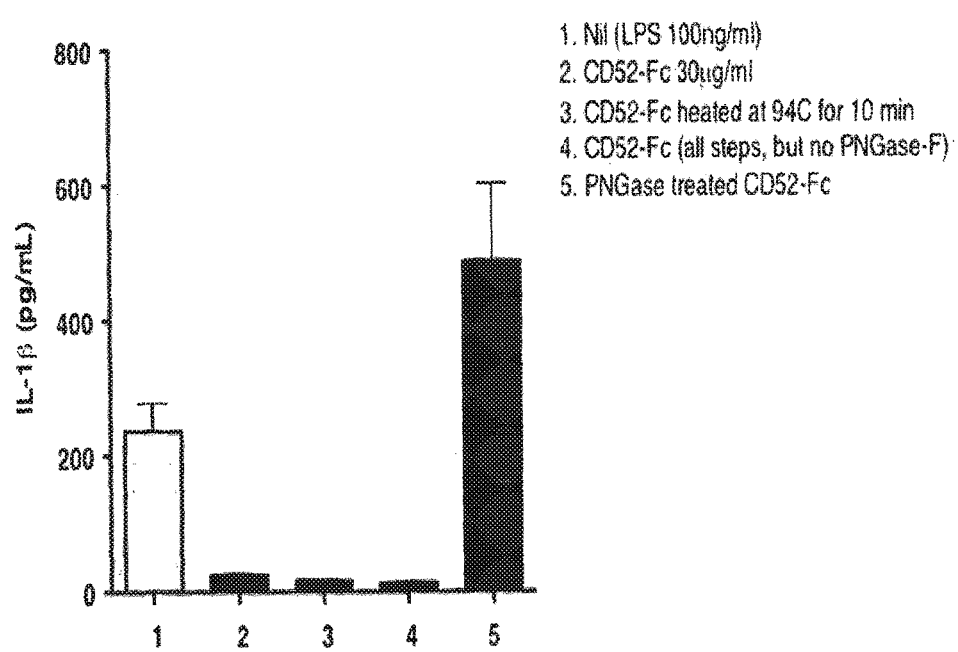

FIG. 29: Treatment with PNGase-F to remove N-linked oligosaccharide abolishes the suppressive effect of hCD52-Fc on LPS-induced IL-1β section by THP-1 cells.

Human CD52-Fc (300 µg) treated with or without PNGase F to remove N-linked oligosaccharide was used to treat THP-1 cells in the presence of LPS. Media were collected and the concentration of IL-1β measured by ELISA.

FIGS. 30A-30C: Carbohydrate moieties that may be attached to soluble CD52 peptide fragment are depicted.

KEY TO THE SEQUENCE LISTING

SEQ ID NO: 1 Human CD52 mRNA transcript (NCBI Reference Sequence: NM_001803.2)
SEQ ID NO: 2 Amino acid sequence of human CD52
SEQ ID NO: 3 12 amino acid soluble peptide of human CD52
SEQ ID NO: 4 Orthologous monkey soluble CD52 peptide
SEQ ID NO: 5 Orthologous mouse soluble CD52 peptide
SEQ ID NO: 6 Orthologous rat soluble CD52 peptide
SEQ ID NO: 7 Orthologous dog soluble CD52 peptide
SEQ ID NO: 8 CD52 F primer
SEQ ID NO: 9 CD52 R primer
SEQ ID NO: 10 FOXP3 F primer
SEQ ID NO: 11 FOXP3 R primer
SEQ ID NO: 12 CTLA-4 F primer
SEQ ID NO: 13 CTLA-4 R primer
SEQ ID NO: 14 GITR F primer
SEQ ID NO: 15 GITR R primer
SEQ ID NO: 16 CD127 F primer
SEQ ID NO: 17 CD127 R primer
SEQ ID NO: 18 IL-2α forward primer
SEQ ID NO: 19 IL-2α reverse primer
SEQ ID NO: 20 IL-27β forward primer
SEQ ID NO: 21 IL-27β reverse primer
SEQ ID NO: 22 IL-12α forward primer
SEQ ID NO: 23 IL-12α reverse primer
SEQ ID NO: 24 1F1 primer
SEQ ID NO: 25 1R1 primer
SEQ ID NO: 26 1F2 primer
SEQ ID NO: 27 1R2 primer
SEQ ID NO: 28 2F primer
SEQ ID NO: 29 2R1 primer
SEQ ID NO: 30 2R2 primer
SEQ ID NO: 31 CD52 forward primer
SEQ ID NO: 32 CD52 reverse primer
SEQ ID NO: 33 IL-2 forward primer
SEQ ID NO: 34 IL-2 reverse primer
SEQ ID NO: 35 IL-4 forward primer
SEQ ID NO: 36 IL-4 reverse primer
SEQ ID NO: 37 IL-10 forward primer
SEQ ID NO: 38 IL-10 reverse primer
SEQ ID NO: 39 IL-13 forward primer
SEQ ID NO: 40 IL-13 reverse primer
SEQ ID NO: 41 FoxP3 forward primer
SEQ ID NO: 42 FoxP3 reverse primer
SEQ ID NO: 43 CD127 forward primer
SEQ ID NO: 44 CD127 reverse primer
SEQ ID NO: 45 CTLA-4 forward primer
SEQ ID NO: 46 CTLA-4 reverse primer
SEQ ID NO: 47 FASLG forward primer
SEQ ID NO: 48 FASLG reverse primer SEQ ID NO: 49 TGFb1 forward primer
SEQ ID NO: 50 TGFb1 reverse primer
SEQ ID NO: 51 TGFb2 forward primer
SEQ ID NO: 52 TGFb2 reverse primer
SEQ ID NO: 53 IFNg forward primer
SEQ ID NO: 54 IFNg reverse primer
SEQ ID NO: 55 IL-12 alpha forward primer
SEQ ID NO: 56 IL-12 alpha reverse primer
SEQ ID NO: 57 Ebi3 forward primer
SEQ ID NO: 58 Ebi3 reverse primer
SEQ ID NO: 59 RARA forward primer
SEQ ID NO: 60 RARA reverse primer
SEQ ID NO: 61 GITR forward primer
SEQ ID NO: 62 GITR reverse primer
SEQ ID NO: 63 GRANZMB forward primer
SEQ ID NO: 64 GRANZMB reverse primer
SEQ ID NO: 65 ALDH1A2 forward primer
SEQ ID NO: 66 ALDH1A2 reverse primer
SEQ ID NO: 67 ACTIN forward primer
SEQ ID NO: 68 ACTIN reverse primer
SEQ ID NO: 69 Human Siglec-10 protein sequence (GenBank Accession No. AF310233.1)

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−20%, more preferably +/−10%, more preferably +/−5%, of the designated value. For the avoidance of doubt, the term "about" followed by a designated value is to be interpreted as also encompassing the exact designated value itself (for example, "about 10" also encompasses 10 exactly).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "immune response" has its ordinary meaning in the art, and includes both humoral and cellular immunity. An immune response may be mediated by one or more of, T-cell activation, B-cell activation, natural killer cell activation, activation of antigen presenting cells (e.g., B cells, DCs, monocytes and/or macrophages), cytokine production, chemokine production, specific cell surface marker expression, in particular, expression of co-stimulatory molecules. In a preferred embodiment, the immune response which is suppressed using the methods of the invention is at least effector T cell function by reducing the survival, activity and/or proliferation of this cell type. In another preferred embodiment, the immune response which is suppressed using the methods of the invention is at least one or more of monocyte, macrophage or dendritic cell function by reducing the survival, activity and/or proliferation of one or more of these cell types. In a further preferred embodiment, the immune response is suppressed to an extent such that it induces tolerance to an antigen such as an autoantigen.

As used herein, "tolerance" refers to a state of immune unresponsiveness to a specific antigen or group of antigens to which a subject is normally responsive Immune tolerance is achieved under conditions that suppress the immune reaction and is not just the absence of an immune response.

As used herein, the terms "treating", "treat" or "treatment" include administering a therapeutically effective amount of an agent sufficient to reduce or eliminate at least one symptom of disease.

As used herein, the terms "preventing", "prevent" or "prevention" include administering a therapeutically effective amount of an agent sufficient to prevent the manifestation of at least one symptom of disease.

As used herein, the term "suppressing" includes reducing by any quantifiable amount.

As used herein, the term "subject" refers to an animal, e.g., a mammal. In a preferred embodiment, the subject is mammal, for example a human. Other preferred embodiments include livestock animals such as horses, cattle, sheep and goats, as well as companion animals such as cats and dogs.

As used herein, the term "host" refers to any organism from which soluble CD52 can be isolated or in which soluble CD52 can be produced, by any means. The host may be whole organism or may be a cell derived therefrom. The host may be an animal, e.g., a mammal. In a preferred embodiment, the host is mammalian, for example a human. Other preferred hosts include mice, rats, monkeys, hamsters, guinea-pigs, rabbits, and any animal or cell which may serve as a suitable host from which soluble CD52 can be isolated or in which soluble CD52 can be produced.

As used herein, the terms "linked", "attached", "conjugated", "bound", "coupled" or variations thereof are used broadly to refer to any form of covalent or non-covalent association which joins one entity to another for any period of time.

Soluble CD52

The present disclosure describes, for the first time, the suppression of immune cells such as effector T-cells, monocytes and dendritic cells by a soluble CD52 glycoprotein fragment. CD52 is a surface glycosylphosphatidylinositol (GPI)-anchored glycoprotein present on most lymphoid cells, initially recognised as the target of complement-binding CAMPATH monoclonal antibodies used therapeutically to deplete lymphocytes (Treumann et al., 1995; Xia et al., 1991; Hale, 2001). The mRNA transcript of the human CD52 gene is shown in SEQ ID NO: 1 and the translated amino acid sequence is shown in SEQ ID NO: 2. Mature CD52 tethered by its GPI anchor comprises only 12 amino acids and an asparagine (N)-linked terminal carbohydrate.

Unless stated otherwise, the terms "soluble CD52 glycoprotein", "soluble CD52", "soluble glycoprotein" and variations thereof are used interchangeably herein.

Membrane-anchored CD52 can be cleaved (for example, enzymatically) to release a soluble peptide fragment comprising the amino acid sequence GQNDTSQTSSPS (SEQ ID NO: 3). The soluble CD52 glycoprotein disclosed herein may comprise an amino acid sequence at least 60% identical to the amino acid sequence of SEQ ID NO: 3 or at least 60% identical to the amino acid sequence of other known, orthologous CD52 soluble fragment sequences. Thus, orthologous sequences of the soluble CD52 peptide fragment are encompassed by the present disclosure. Such sequences include but are not limited to the monkey sequence SQNATSQSSPS (SEQ ID NO: 4), the mouse sequence GQATTAASGTNKNSTSTKKTPLKS (SEQ ID NO: 5), the rat sequence GQNSTAVTTPANKAAT-TAAATTKAAATTATKTTTAVRKTPGKPPKA (SEQ ID NO: 6), the dog sequence GNSTTPRMTTKKVKSATPA (SEQ ID NO:7), and other orthologous sequences readily identifiable from known CD52 polypeptide and polynucleotide sequences.

Percentage identity to any of the amino acid or polynucleotide sequences disclosed herein may be determined by methods known in the art. For example, amino acid and polynucleotide sequences can be compared manually or by using computer-based sequence comparison and identification tools that employ algorithms such as BLAST (Basic Local Alignment Search Tool; Altschul et al., 1993); see also www.ncbi.nlm nih.gov/BLAST/), the Clustal method of alignment (Higgins and Sharp, 1989) and others, wherein appropriate parameters for each specific sequence comparison can be selected as would be understood by a person skilled in the art. The amino acid sequence of the peptide portion of the glycoprotein disclosed herein can be at least 65%, at least 70%, at least 75%, at least 80%, at least 85%, at least 90%, at least 95% identical, or at least 99% identical to any one or more of the amino acid sequences identified in SEQ ID NOs: 3, 4, 5, 6 or 7. For example, the amino acid sequence of the peptide portion of the glycoprotein disclosed herein can be 100% identical to any one of the amino acid sequences identified in SEQ ID NOs: 3, 4, 5, 6 or 7.

Isolated soluble CD52 glycoprotein may be used to produce pharmaceutical compositions of the invention. The term "isolated" is used herein to define the isolation of the soluble CD52 glycoprotein so that it is present in a form suitable for application in a pharmaceutical composition. Thus, the glycoprotein disclosed herein is isolated from other components of a host cell or fluid or expression system to the extent that is required for subsequent formulation of the glycoprotein as a pharmaceutical composition. The isolated glycoprotein is therefore provided in a form which is substantially free of other components of a host cell (for example, proteins) which may hinder the pharmaceutical effect of the glycoprotein. Thus, the isolated glycoprotein may be free or substantially free of material with which it is naturally associated such as other glycoproteins, polypeptides or nucleic acids with which it is found in its natural environment, or the environment in which it is prepared (e.g. cell culture) when such preparation is by recombinant DNA technology practised in vitro or in vivo. Soluble glycoprotein can be isolated from a host cell or fluid or expression system by methods known in the art.

The term "soluble" is used herein to define a peptide or glycoprotein which is not bound to a cell membrane. The soluble peptide or glycoprotein may be able to move freely in any solvent or fluid, such as a bodily fluid. For example, the soluble peptide or glycoprotein may be able to circulate in blood.

The carbohydrate may be any carbohydrate moiety attached to the soluble CD52 peptide fragment. For example, the carbohydrate may be any carbohydrate moiety found to be attached to the extracellular portion of the CD52 protein in a host. Thus, the carbohydrate may be any carbohydrate capable of being attached to the extracellular portion of the CD52 protein by a glycosylation reaction known to take place in a host.

Carbohydrate moieties present on a naturally occurring CD52 glycoprotein can be identified by known methods, such as those described in Schröter et al. (1999). Such carbohydrate moieties may be identified from CD52 glycoproteins present in any host cell expressing CD52, and particularly lymphocytes, such as $CD4^+$ or $CD8^+$ T-cells, monocytes or genital tract cells, such as sperm cells or epididymal duct cells. Thus, the precise structure of the carbohydrate moiety can be determined by applying methods such as mass spectrometry (e.g. Matrix-assisted Laser Desorption/Ionization-Time of Flight Mass Spectrometry (MALDI-TOF)), Mono-Q anion-exchange chromatography, high pH anion exchange chromatography (HPAEC-PAD), methylation analysis, endo-β-galactosidase digestion, and other methods. The N-glycans may be separated from a naturally occurring CD52 glycoprotein using known cleavage enzymes such as peptide-N4-(N-acetyl-β-D-glucosaminyl)asparagines amidase F ('PNGase F' from *Flavobacterium meningosepticum*, recombinant from *Escherichia coli*; obtainable from commercial suppliers such as Roche). The N-glycans can be isolated for further characterisation using known chromatographic methods, such as C8-reversed phase chromatography. In one example, the carbohydrate may comprise one or more bi-, tri- or tetra-antennary sugars, which may be terminally sialylated. For example, the carbohydrate may comprise one or more tetra-antennary sugars. The sugars may be branched or unbranched. The sugars may comprise a proximal fucose. Thus, the carbohydrate may be fucosylated. The sugars may comprise one or more N-acetyllactosamine repeats. Thus, the sugars may comprise polylactosamine units. In addition, the sugars may comprise a mannose core.

The carbohydrate may have any one or more of the structures described in Treumann et al. (1995). Thus, for example, the carbohydrate may have any of the structures depicted in FIGS. 30A-30C.

Thus, the carbohydrate may comprise one or more sialic acids. The one or more sialic acids may be located in any portion of the carbohydrate. For example, the one or more sialic acids may be terminal sialic acids. In one particular example, the carbohydrate may comprise terminal α2-6 sialic acids. Thus, the carbohydrate may comprise one or more surface α2-6-sialyllactose groups. The one or more sialic acids may be attached to galactose in β1-4 linkage with N-acetylglucosamine The present disclosure demonstrates that the soluble CD52 glycoprotein exerts its suppressive effect at least in part via binding to the sialic acid binding Ig-like lectin-10 (Siglec-10), a cell surface transmembrane receptor and immunoglobulin superfamily member bearing two cytoplasmic immunoreceptor tyrosine-based inhibition motifs (IT- IMs) (Munday et al., 2001; Crocker et al., 2007). Thus, the soluble glycoprotein disclosed herein may be capable of binding to Siglec-10. For example, the soluble glycoprotein disclosed herein may comprise a carbohydrate moiety capable of binding to Siglec-10. In one example, the carbohydrate moiety comprises one or more surface α2-6- or α2-3-sialyllactose groups that are capable of binding to Siglec-10. Alternatively, the carbohydrate moiety may comprise any other surface groups that are capable of binding to Siglec-10.

The soluble glycoprotein disclosed herein may be capable of binding to Siglec-10 derived from any species. For example, the soluble glycoprotein disclosed herein may be capable of binding to Siglec-10 derived from any mammalian species. Preferably, the soluble glycoprotein disclosed herein is capable of binding to human Siglec-10. The polypeptide sequence of human Siglec-10 is defined in Munday et al. (2001), in GenBank Accession No. AF310233.1, and in SEQ ID NO: 69.

The soluble glycoprotein disclosed herein may be capable of effecting signalling via the Siglec-10 receptor. Thus, the soluble glycoprotein disclosed herein may be capable of binding to Siglec-10 to any extent sufficient to effect signalling via the Siglec-10 receptor. Thus, the precise level of binding to Siglec-10 can vary. Methods for determining whether a given glycoprotein is capable of binding to Siglec-10, and for determining whether a given glycoprotein is capable of effecting signalling via the Siglec-10 receptor are known in the art.

Further examples of the N-linked CD52 carbohydrate which the glycoprotein disclosed herein may comprise are those derived or derivable from host lymphocyte CD52 glycoproteins or genital tract cell CD52 glycoproteins.

Due to the complex nature of many naturally occurring carbohydrate moieties known to be linked to the extracellular protein portion of human CD52 and the many variations in these structures that may arise from varying glycosylation patterns, it will be understood that the precise nature of the carbohydrate moiety present in the glycoprotein disclosed herein may vary. As stated above, methods are available to precisely identify particular carbohydrate moieties from naturally occurring CD52 glycoproteins. In addition, a number of different carbohydrate moieties can be added to the soluble peptide fragment of CD52 by expressing CD52 under varying glycosylation conditions. For example, the soluble glycoprotein disclosed herein may be expressed in and/or isolated from host lymphocyte cells, monocytes or host genital tract cells (e.g. sperm cells, or epididymal duct cells) or seminal fluid and may therefore comprise different carbohydrate groups as a result. The inventors have shown that soluble CD52 present in human semen, similarly to soluble CD52 released from lymphocytes such as Daudi B cells, is capable of suppressing T-cell function and/or an immune response. Alternative host cells providing different glycosylation conditions may be selected for expression of soluble CD52 in order to provide alternative forms of carbohydrate on the soluble glycoprotein.

The carbohydrate may be attached to any one or more amino acid in the peptide which is capable of having a carbohydrate moiety attached thereto. For example, the carbohydrate may be attached to one or more asparagine, serine, threonine, tyrosine, hydroxylysine, hydroxyproline, phosphoserine or tryptophan residues if present in the amino acid sequence. In one example, the carbohydrate is attached to the asparagine (N) residue in a peptide portion having a sequence at least 60%, at least 65%, at least 70%, at least 75%, at least 80%, at least 85%, at least 90%, at least 95% identical, or is 100% identical, to the amino acid sequence set out in SEQ ID NO: 3.

The present disclosure also provides variants, mutants, biologically active fragments, modifications, analogs and/or derivatives of the glycoprotein disclosed herein. Such compounds can be identified by screening for compounds which mimic the structure and/or function of the polypeptide disclosed herein, using methods including any of the methods disclosed herein.

Soluble CD52 Function

The glycoprotein disclosed herein is preferably capable of suppressing the activity ("function") of immune cells including lymphocytes (such as a T-cell) and monocytes. For example, the glycoprotein disclosed herein is capable of suppressing one or more of effector T-cell, monocyte, macrophage and dendritic cell function. Effector T-cells, monocytes, macrophages and dendritic cells and their functions will be known to a person skilled in the art.

T-cells can be readily identified by the presence of any of one or more T-cell markers known in the art. The glycoprotein disclosed herein is capable of reducing T-cell proliferation in response to antigen challenge, and/or capable of reducing T-cell cytokine production (such as production of any one or more of IFN-γ, IL-2, IL-10, IL-17, G-CSF, TNF-α, and other cytokines known to be secreted by activated T-cells). For example, soluble CD52 is capable of reducing IFN-γ production by T-cells.

In another example, soluble CD52 is capable of reducing IL-1β secretion by monocytes, macrophages and dendritic cells.

Accordingly, the glycoprotein disclosed herein is capable of reducing an immune response in a host. The inventors have shown that the glycoprotein disclosed herein is capable of reducing effector T-cell function in response to challenge with any antigen. The suppressive function is not dependent on the particular antigen used in the challenge. Thus, the glycoprotein disclosed herein is capable of reducing an immune response to any antigen. In one example, the antigen is an autoantigen.

Any known methods of determining the suppression of T-cell function and/or an immune response can be used, such as (but not limited to) those described in the examples herein. Thus, the methods may comprise determining the effect of the glycoprotein disclosed herein on one or more of effector T-cell, monocyte, macrophage and dendritic cell proliferation and/or on the production of any one or more of IFN-γ, IL-2, IL-10, IL-17, G-CSF, TNF-α, and other cytokines known to be secreted by activated T-cells, monocytes, macrophages or dendritic cells.

Fusion Proteins

The peptide portion of the CD52 glycoprotein disclosed herein may, for example, be conjugated to a second protein as a fusion protein. The second protein may be any protein capable of increasing the stability and/or solubility of the glycoprotein, of enhancing the process of making the glycoprotein by recombinant methods, or of enhancing the therapeutic effect of the glycoprotein. Thus, the second protein may capable of increasing the half life of the glycoprotein disclosed herein.

The second protein can be of any suitable length. In one embodiment, the second protein may be relatively short. For example, the second protein may consist of any of 1, 2, 3, 4, 5, 6, 7, 8, 9, 10, or more amino acids. The second protein may comprise at least 1, at least 2, at least 3, at least 4, at least 5, at least 6, at least 7, at least 8, at least 9 or at least 10 amino acids. The second protein may also comprise more than 10 amino acids. For example, the second protein may comprise at least 10, at least 15, at least 20, at least 25, at least 30, or at least 50 amino acids.

In one example, the second protein is an antibody fragment. Suitable antibody fragments include any antibody fragment that is capable of activating the immune system. The antibody fragment may be a fragment crystallizable (Fc) region (which can be a single polypeptide) or any one or more heavy chain constant domains (e.g. $C_H$ domains 2, 3 and/or 4) from an Fc region. In one example, the second protein is an Fc fragment.

In another example, the second protein may be a purification tag. Many examples of purification tags are known, and include (without limitation) a His tag, T7 tag, FLAG tag, S-tag, HA tag, c-Myc tag, DHFR, a chitin binding domain, a calmodulin binding domain, a cellulose binding domain, a Strep 2 tag (a purification tag encoding eight amino acids that binds to Strep-Tactin, a specifically engineered streptavidin (Schmidt and Skerra, 2007), and others.

The second protein may increase the solubility of the expressed protein. Such proteins include (without limitation) NusA, thioredoxin, small ubiquitin-like modifier (SUMO), ubiquitin and others known in the art.

The second protein may increase the solubility of the expressed protein as well as enhancing purification methods. Such proteins include (without limitation) GST, MBP, T7 gene 10, and others known in the art.

The purification tag may optionally be removed from the fusion protein after its production. Suitable methods of removing a purification tag from a fusion protein will vary depending on the particular purification tag used. Such methods will be generally known in the art.

The fusion protein disclosed herein may comprise one or more of any of the second proteins described above, in any combination. Thus, the fusion protein may comprise an antibody fragment (such as an Fc) and a purification tag (such as a Strep 2 tag).

Polynucleotides

The present disclosure further provides isolated or recombinant polynucleotides encoding the protein component of the soluble CD52 glycoprotein, or the fusion protein. The sequences of such polynucleotides are derivable from the amino acid sequences of the CD52 protein and soluble CD52 peptide fragment described herein and of the second protein comprised within the fusion protein. The polynucleotides disclosed herein may also encode a full length CD52 protein, which may, for example, be a mature form thereof, or a precursor thereof.

The term "isolated polynucleotide" is intended to mean a polynucleotide which has generally been separated from the polynucleotide sequences with which it is associated or linked in its native state. Preferably, the isolated polynucleotide is at least 60% free, more preferably at least 75% free, and more preferably at least 90% free from other components with which it is naturally associated. Furthermore, the term "polynucleotide" is used interchangeably herein with the terms "nucleic acid molecule", "gene" and "mRNA".

The term "recombinant" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. A recombinant polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

"Polynucleotide" refers to an oligonucleotide, a polynucleotide or any fragment thereof. It may be DNA or RNA of genomic or synthetic origin, double-stranded or single-stranded, and combined with carbohydrate, lipids, protein, or other materials to perform a particular activity defined herein.

The polynucleotides disclosed herein may possess, when compared to naturally occurring molecules (such as genomic polynucleotides encoding CD52 or a soluble fragment thereof), one or more mutations which are deletions, insertions, or substitutions of nucleotide residues. Mutants can be either naturally occurring (that is to say, isolated from a natural source) or synthetic (for example, made by performing site-directed mutagenesis or DNA shuffling techniques as broadly described by Harayama (1998)). It is thus apparent that polynucleotides of the invention can be either naturally occurring or recombinant The particular sequence of the polynucleotide can be determined from the peptide sequence. Due to the redundancy of the genetic code, different sequences can be used to encode the same peptide. In addition, the polynucleotide sequence may be specifically altered so as to enhance its expression in a particular host cell. Such a process is well known in the art as "codon optimization". Thus, the polynucleotide disclosed herein may be codon optimized to enhance expression in a host cell.

Vectors

The polynucleotide disclosed herein can be inserted into a nucleotide vector in order to facilitate expression of the protein component of the glycoprotein or the fusion protein. Accordingly, the present disclosure provides a vector comprising a polynucleotide encoding the protein component of the glycoprotein disclosed herein or the fusion protein disclosed herein. The vector can be either RNA or DNA, either prokaryotic or eukaryotic, and may be a transposon (such as described in U.S. Pat. No. 5,792,294), a virus or a plasmid.

Preferably, the polynucleotide encoding the protein component of the glycoprotein or the fusion protein is operably linked to a promoter which is capable of expressing the peptide under suitable conditions. "Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as a polynucleotide defined herein, if it stimulates or modulates the transcription of the coding sequence in an appropriate cell or cell-free expression system. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

The vector is preferably an expression vector. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. The expression vectors disclosed herein include any vectors that function (i.e., direct gene expression) in the recombinant cells disclosed herein (including in animal cells) or in a suitable cell-free expression system.

In particular, the expression vectors disclosed herein may contain regulatory sequences such as transcription control sequences, translation control sequences, origins of replication, and other regulatory sequences that are compatible with the recombinant cell or cell-free expression system and that control the expression of polynucleotide molecules disclosed herein. In particular, the vectors disclosed herein may include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells or cell-free expression systems described herein. A variety of such transcription control sequences are known to those skilled in the art.

The vectors disclosed herein may also contain (a) secretory signals (i.e., signal segment nucleic acid sequences) to enable an expressed protein or peptide to be secreted from a cell that produces the peptide and/or (b) fusion sequences which lead to the expression of peptides disclosed herein as fusion proteins. Examples of suitable signal segments include any signal segment capable of directing the secretion of a glycoprotein or fusion protein disclosed herein. The vectors may also include intervening and/or untranslated sequences surrounding and/or within the nucleic acid sequence(s) encoding the peptide disclosed herein.

The polynucleotide or vector can be expressed in a host cell or in a cell-free expression system in order to produce the glycoprotein or fusion protein disclosed herein. Such expression may be performed, for example in a mammalian cell, a baculovirus expression system, a fungal expression system (which may be selected so as to permit glycosylation of the expressed protein).

The host cell can be any cell capable of producing the glycoprotein or fusion protein disclosed herein. Thus, in one example, the host cell is capable of permitting glycosylation of the protein component of the glycoprotein disclosed herein. Suitable host cells can be readily identified by the skilled artisan, and include, for example, animal cells, such as mammalian cells. In one example, the host cell is a CHO cell, a myeloma cell (such as the mouse myeloma NS—O or SP2-O cells) or a HEK293T cell. In another example, the host cell is a Daudi B lymphoblast cell (Hu et al., 2009).

In addition, the polynucleotide or vector can be introduced into a host cell for administration to a subject. Thus, the pharmaceutical composition disclosed herein may comprise a cell comprising the polynucleotide or vector disclosed herein. The cell may be an isolated cell. The cell is preferably a recombinant cell. Thus, the cell is preferably transfected with a polynucleotide or vector disclosed herein. Any host cell suitable for administration to a subject may be used. In one example, the cell may be a cell taken from the subject to be treated. Thus, the cell may be an autologous cell. Accordingly, one or more cells may be taken from a subject, a polynucleotide or vector as disclosed herein may be introduced into the subject's cell, and the cell may then be administered to the same subject. In one example, the cell may be a lymphocyte, such as a T-cell, such as a $CD4^+$ T-cell. Methods for taking a suitable cell sample from a subject in this regard will be known in the art. Where the cell to be used is a lymphocyte, the methods may include lymphocytapheresis. Other suitable host cells, which need not necessarily be derived from the subject to be treated, can equally be used. Expression of the polynucleotide or vector in the cell preferably results in the production and/or secretion of the glycoprotein disclosed herein.

Transformation of a polynucleotide into a host cell can be accomplished by any suitable method known in the art. Transformation techniques include, but are not limited to, transfection, electroporation, microinjection, lipofection, and adsorption. A recombinant cell may remain unicellular or may grow into a tissue, organ or a multicellular organism. Transformed polynucleotide molecules as disclosed herein can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide as disclosed herein. Host cells can be either endogenously (i.e., naturally) capable of producing polypeptides of the present invention or can be rendered capable of producing such polypeptides after being transformed with at least one polynucleotide molecule as disclosed herein.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules as disclosed herein include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules as disclosed herein to correspond to the codon usage of the host cell, and the deletion of sequences that destabilize transcripts.

The host cell may be cultured under conditions effective to produce the glycoprotein or fusion protein. Once expressed in the host cell, the glycoprotein or fusion protein can be isolated by conventional methods known in the art. Thus, in one embodiment, an isolated glycoprotein or fusion protein as described herein is produced by culturing a cell capable of expressing the glycoprotein or fusion protein under conditions effective to produce the glycoprotein or fusion protein, and isolating the glycoprotein or fusion protein. Effective culture conditions include, but are not limited to, effective media, bioreactor, temperature, pH and oxygen conditions that permit glycoprotein or fusion protein production, and in particular, that permit glycosylation. An effective medium refers to any medium in which a cell is cultured to produce a glycoprotein or fusion protein as disclosed herein. Such medium typically comprises an aqueous medium having assimilable carbon, nitrogen and phosphate sources, and appropriate salts, minerals, metals and other nutrients, such as vitamins. Host cells can be cultured in conventional fermentation bioreactors, shake flasks, test tubes, microtiter dishes, and Petri plates. Culturing can be carried out at a temperature, pH and oxygen content appropriate for a recombinant cell. Such culturing conditions are within the expertise of one of ordinary skill in the art.

Any cell-free expression system suitable for the expression of the polynucleotide disclosed herein can also be used. Suitable cell-free expression systems include those that permit glycosylation of the protein component of the glycoprotein or fusion protein. Such conditions can be determined by a person skilled in the art.

The glycoprotein disclosed herein may also be produced by inducing expression of CD52 in an isolated host cell and isolating soluble CD52 glycoprotein produced by the host cell. Thus, the glycoprotein may be produced using a cell which naturally produces soluble CD52. Suitable cells will be identifiable to the person skilled in the art and include (without limitation) lymphocytes, cells of the genital tract area (such as sperm cells), Daudi B lymphoblast cells (Hu et al., 2009), K562 cells, and others. Additional cell lines capable of naturally producing soluble CD52 can be identified by screening for soluble CD52 secretion. Thus, cancer cells can be screened for their ability to secrete soluble CD52.

The methods of producing the glycoprotein disclosed herein from an isolated host cell which naturally produces soluble CD52 may comprise stimulating the host cell to produce higher levels of soluble CD52. This may be achieved, for example, by contacting the host cell with an antigen. Any antigen may be used. In one example, the antigen is an autoantigen, such as GAD65. In another example, the antigen is tetanus toxoid.

The methods of producing the glycoprotein disclosed herein from an isolated host cell which naturally produces soluble CD52 may also comprise selecting a cell which naturally expresses CD52 and contacting the cell with an enzyme capable of cleaving the extracellular portion of membrane-bound CD52 to release soluble CD52. Suitable enzymes are known in the art and include phospholipases such as phospholipase C.

The methods described herein can be performed on isolated cells or cell populations of a size sufficient to produce the desired quantity of soluble CD52.

$CD52^{hi}$ Cells

The present disclosure also provides isolated cells and cell populations exhibiting high levels of expression of CD52. By "high" it is meant that the expression levels of CD52 are relatively high compared to CD52 expression levels in a given population of cells. The given population of cells may be, for example, a population of lymphocytes. The lymphocyte population may comprise Treg cells and non-Treg cells. In addition, the lymphocyte population may have been contacted with an antigen in order to stimulate lymphocyte activity. Alternatively, the population of cells may be cells of the genital tract, such as sperm cells. By contrast, $CD52^{lo}$ cells exhibit relatively low levels of CD52 relative to a given population of cells.

In one example, a cell may be determined to be a $CD52^{hi}$ cell if the level of expression of CD52 in that cell falls within the top 1%, 5%, 10%, 20%, 30%, 40% or 50% CD52 expression levels in a population of cells. Preferably, a $CD52^{hi}$ cell has an expression level within the top 10% of CD52 expression observed in a population of cells.

In one example, a cell may be determined to be a $CD52^{lo}$ cell if the level of expression of CD52 in that cell falls within the bottom 1%, 5%, 10%, 20%, 30%, 40% or 50% CD52 expression levels in a population of cells. Preferably, a $CD52^{lo}$ cell has an expression level within the bottom 10% of CD52 expression observed in a population of cells.

The $CD52^{hi}$ cell may be isolated from the population of cells from which it is identified. Alternatively, a population of $CD52^{hi}$ cells may be isolated from the initial cell population from which the $CD52^{hi}$ cells are identified. Thus, the cell populations disclosed herein may be enriched for $CD52^{hi}$ cells.

The present disclosure therefore provides an isolated cell population comprising a plurality of $CD52^{hi}$ cells. The $CD52^{hi}$ cells may comprise at least 15%, 20%, 30%, 40%, 50%, 60%, 70%, 80%, 90% or 95% of the total enriched cell population.

The isolated $CD52^{hi}$ cells and populations of $CD52^{hi}$ cells disclosed herein are capable of producing the soluble CD52 glycoprotein disclosed herein.

These isolated cells and cell populations may be further defined by the presence of one or more additional cell markers. In one example, the $CD52^{hi}$ cells are $CD4^+$ $CD52^{hi}$ cells. Alternatively, the $CD52^{hi}$ cells are $CD8^+CD52^{hi}$ cells. Additional markers that characterise these cells include any one or more of glucocorticoid-induced tumor necrosis factor receptor related protein (GITR), CD127, Fas ligand (FasL or CD95L), sphingosine-1-phosphate receptor (S1PR), the GPI-anchored glycoprotein CD24, CD25, FoxP3, CTLA-4, and other markers, in any combination. The inventors have found that GITR, CD127, Fas L, S1PR and CD24 expression levels may be higher in $CD52^{hi}$ Treg cells compared to $CD52^{lo}$ cells. These markers can therefore be used to further define a $CD52^{hi}$ cell or a $CD52^{hi}$ cell population as described herein.

In addition, the function of a given cell may be used to define a $CD52^{hi}$ cell or a $CD52^{hi}$ cell population as described herein. For example, the ability of a cell expressing CD52 to reduce effector T-cell function as described herein can be used to identify a $CD52^{hi}$ cell or a $CD52^{hi}$ cell population.

Cell Culture Medium $CD52^{hi}$ cells or a $CD52^{hi}$ cell population as described herein may be cultured so as to produce medium comprising the soluble glycoprotein disclosed herein. Suitable culture conditions will be apparent to the person skilled in the art. The cultured cells may additionally be induced to increase their level of expression of soluble CD52 by any suitable method, including by contacting the cells with antigen.

Ex Vivo Cell Treatment

The present invention also provides a pharmaceutical composition comprising cells, preferably immune cells, and a pharmaceutically acceptable carrier, wherein the cells have been treated ex vivo with any one or more of:
  i) soluble CD52 glycoprotein,
  ii) a fusion protein comprising soluble CD52 glycoprotein as a first protein, and a second protein;
  iii) a polynucleotide encoding the peptide portion of soluble CD52 glycoprotein of part i) or the fusion protein of part ii);
  iv) a vector comprising the polynucleotide of part iii);
  v) an isolated cell comprising the polynucleotide of part iii) or the vector of part iv);
  vi) an isolated $CD52^{hi}$ cell capable of producing soluble CD52 glycoprotein;
  vii) an isolated cell population comprising a plurality of $CD52^{hi}$ cells capable of producing soluble CD52 glycoprotein;
  viii) cell culture medium, or a fraction thereof comprising soluble CD52 glycoprotein, isolated from a cell culture comprising the cell of part vi) or the cell population of part vii); and
  ix) an agent capable of increasing the level of expression of soluble CD52 glycoprotein by a cell;

The cells of the composition may be, for example, whole blood or a cellular fraction thereof such as peripheral blood mononuclear cells (PBMCs).

Such ex vivo treated cells can be used in the present invention, for example for treating or preventing a disease or condition mediated by effector T-cell function, inflammation or sepsis.

In one embodiment, the cells are autologous in respect to the subject to which they will be administered. In another embodiment, the cells are allogeneic.

Pharmaceutical Compositions

The present disclosure provides a pharmaceutical composition comprising any one or more of the soluble CD52 glycoprotein, fusion protein, polynucleotide, vector, cell, cell populations and cell medium described herein, and any agent capable of increasing the level of expression of CD52 in a cell, and a pharmaceutically acceptable carrier.

A pharmaceutically acceptable carrier includes a carrier suitable for use in administration to animals, such as mammals and at least preferably humans. In one example, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like.

Therapeutic compositions can be prepared by mixing the desired compounds having the appropriate degree of purity with optional pharmaceutically acceptable carriers, excipients, or stabilizers (Remington's Pharmaceutical Sciences, 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG). Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances.

A pharmaceutical composition as disclosed herein is formulated to be compatible with its intended route of administration. Examples of routes of administration include parenteral (e.g., intravenous, intradermal, subcutaneous, intramuscular, intraperitoneal, intrathecal), mucosal (e.g., oral, rectal, intranasal, buccal, vaginal, respiratory), enteral (e.g., orally, such as by tablets, capsules or drops, rectally) and transdermal (topical, e.g., epicutaneous, inhalational, intranasal, eyedrops, vaginal). Solutions or suspensions used for parenteral, intradermal, enteral or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Transdermal delivery is accomplished by exposing the therapeutic agent to a patient's skin for an extended period of time. Transdermal patches have the added advantage of providing controlled delivery of a pharmaceutical agent to the body (see, for example, Transdermal and Topical Drug Delivery: From Theory to Clinical Practice, Williams (ed), Pharmaceutical Press, U K (2003); Transdermal Drug Delivery: Developmental Issues and Research Initiatives, Hadgraft and Guy (eds.), Marcel Dekker, Inc., (1989)). For example, a simple adhesive patch can be prepared from a backing material and an acrylate adhesive. The therapeutic agent and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the therapeutic agent. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

For passive delivery systems, the rate of release is typically controlled by a membrane placed between the reservoir and the skin, by diffusion from a monolithic device, or by the skin itself serving as a rate-controlling barrier in the delivery system (see U.S. Pat. Nos. 4,816,258; 4,927,408; 4,904,475; 4,588,580, 4,788,062). The rate of delivery will be dependent, in part, upon the nature of the membrane. For example, the rate of delivery across membranes within the body is generally higher than across dermal barriers.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to the invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

Another embodiment of this invention provides for the topical delivery of pharmaceutical composition. This treatment regimen is suitable either for the systemic administration of the pharmaceutical agent or for localized therapy, i.e., directly to pathological or diseased tissue. Topical preparations can be prepared by combining the pharmaceutical agent-chemical modifier complex with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

Dosage forms for the topical administration include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels also may contain excipients, such as animal and vegetable fats, oils, waxes, paraffins, starch, tragacanth, cellulose derivatives, polyethylene glycols, silicones, bentonites, talc and zinc oxide, or mixtures thereof. Powders and sprays also can contain excipients such as lactose, talc, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Mucosal (for example, gastrointestinal, sublingual, buccal, nasal, pulmonary, vaginal, conical, and ocular membranes) drug delivery provides for an efficient entry of active substances to systemic circulation and reduce immediate metabolism by the liver and intestinal wall flora (see, for example, Lee, 2001; Song et al., 2004; Hearnden et al., 2012) Transmucosal drug dosage forms (e.g., tablet, suppository, ointment, gel, salves, creams, pessary, membrane, and powder) are typically held in contact with the mucosal membrane and disintegrate and/or dissolve rapidly to allow immediate systemic absorption.

For delivery to the buccal or sublingual membranes, typically an oral formulation, such as a lozenge, tablet, or capsule will be used. The method of manufacture of these formulations are known in the art, including but not limited to, the addition of the harmaceutical agent-chemical modifier complex to a pre-manufactured tablet; cold compression of an inert filler, a binder, and either a pharmaceutical agent-chemical modifier complex or a substance containing the complex (as described in U.S. Pat. No. 4,806,356) and encapsulation.

Oral compositions generally include an inert diluent or an edible carrier. They can be enclosed in gelatin capsules or compressed into tablets. For the purpose of oral therapeutic administration, the active compound is incorporated with excipients and used in the form of tablets, troches, or capsules. Oral compositions are also prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmaceutical agent-chemical modifier complex into the mouth and through the buccal mucosa.

For delivery to the nasal and/or pulmonary membranes, typically an aerosol formulation will be employed. The term "aerosol" includes any gas-borne suspended phase of the pharmaceutical agent-chemical modifier complex which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the pharmaceutical agent-chemical modifier complex suspended in air or other carrier gas, which may be delivered by inhalation from an inhaler device.

For mucosal or transdermal administration, penetrants appropriate to the barrier to be permeated can be used in the formulation. Such penetrants are generally known in the art, and include, for example, for mucosal administration, detergents, bile salts, and fusidic acid derivatives.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier is a solvent or dispersion medium containing, for example, water, ethanol, polyol (e.g., glycerol, propylene glycol, and liquid polyetheylene glycol, and the like), and suitable mixtures thereof. The proper fluidity is maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid and the like. In many cases, it is preferable to include isotonic agents, for example, sugars, polyalcohols such as manitol, sorbitol, sodium chloride in the composition. Prolonged absorption of the injectable compositions is brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

A pharmaceutically acceptable vehicle is understood to designate a compound or a combination of compounds entering into a pharmaceutical composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen.

Pharmaceutical compositions to be used for in vivo administration should be sterile. This is readily accomplished by filtration through sterile filtration membranes, prior to or following lyophilization and reconstitution. The composition may be stored in lyophilized form or in solution if administered systemically. If in lyophilized form, it is typically formulated in combination with other ingredients for reconstitution with an appropriate diluent at the time for use. An example of a liquid formulation is a sterile, clear, colourless unpreserved solution filled in a single-dose vial for subcutaneous injection.

Pharmaceutical compositions generally are placed into a container having a sterile access port, for example, an intravenous solution bag or vial having a stopper pierceable by a hypodermic injection needle. The compositions are preferably administered parenterally, for example, as intravenous injections or infusions or administered into a body cavity.

The pharmaceutical compositions disclosed herein may further comprise an additional therapeutic agent known to suppress effector T-cell function and/or an immune response.

In one embodiment, the composition further comprises insulin.

In another embodiment, the composition further comprises an autoantigen. Examples of autoantigens useful in compositions of the invention include, but are not limited to, those listed in Table 1 (Lernmark, 2001).

TABLE 1

Recombinant or purified autoantigens recognized by autoantibodies associated with human autoimmune disorders.

| Autoantigen | Autoimmune disease |
| --- | --- |
| A. Cell or organ-specific autoimmunity | |
| Acetylcholine receptor | Myasthenia gravis |
| Actin | Chronic active hepatitis, primary biliary cirrhosis |
| Adenine nucleotide translocator (ANT) | Dilated cardiomyopathy, myocarditis |
| β-Adrenoreceptor | Dilated cardiomyopathy |
| Aromatic L-amino acid decarboxylase | Autoimmune polyendocrine syndrome type I (APS-I) |
| Asialoglycoprotein receptor | Autoimmune hepatitis |
| Bactericidal/permeability-increasing protein (Bpi) | Cystic fibrosis vasculitides |
| Calcium-sensing receptor | Acquired hypoparathyroidism |
| Cholesterol side-chain cleavage enzyme (CYPIIa) | APS-I |
| Collagen type IV $\alpha_3$-chain | Goodpasture syndrome |
| Cytochrome P450 2D6 (CYP2D6) Desmin | Autoimmune hepatitis |
| Desmin | Crohn disease, coronary artery disease |
| Desmoglein 1 | Pemphigus foliaceus |
| Desmoglein 3 | Pemphigus vulgaris |
| F-actin | Autoimmune hepatitis |
| GM gangliosides | Guillain-Barré syndrome |
| Glutamate decarboxylase (GAD65) | Type 1 diabetes, stiff man syndrome |
| Glutamate receptor (GLUR) | Rasmussen encephalitis |
| H/K ATPase | Autoimmune gastritis |
| 17-α-Hydroxylase (CYP17) | APS-I |
| 21-Hydroxylase (CYP21) | Addison disease |
| IA-2 (ICA512) | Type 1 diabetes |
| Insulin | Type 1 diabetes, insulin hypoglycemic syndrome (Hirata disease) |
| Insulin receptor | Type B insulin resistance, acanthosis, systemic lupus erythematosus (SLE) |
| Intrinsic factor type 1 | Pernicious anemia |
| Leukocyte function-associated antigen (LFA-1) | Treatment-resistant Lyme arthritis |
| Myelin-associated glycoprotein (MAG) | Polyneuropathy |
| Myelin basic protein | Multiple sclerosis, demyelinating diseases |
| Myelin oligodendrocyte glycoprotein (MOG) | Multiple sclerosis |
| Myosin | Rheumatic fever |
| p-80-Coilin | Atopic dermatitis |
| Pyruvate dehydrogenase complex-E2 (PDC-E2) | Primary biliary cirrhosis |
| Sodium iodide symporter (NIS) | Graves disease, autoimmune hypothyroidism |
| SOX-10 | Vitiligo |
| Thyroid and eye muscle shared protein | Thyroid associated ophthalmopathy |
| Thyroglobulin | Autoimmune thyroiditis |
| Thyroid peroxidase | Autoimmune Hashimoto thyroiditis |
| Thyrotropin receptor | Graves disease |
| Tissue transglutaminase | Coeliac disease |
| Transcription coactivator p75 | Atopic dermatitis |
| Tryptophan hydroxylase | APS-I |
| Tyrosinase | Vitiligo, metastatic melanoma |
| Tyrosine hydroxylase | APS-I |

TABLE 1-continued

Recombinant or purified autoantigens recognized by autoantibodies associated with human autoimmune disorders.

| Autoantigen | Autoimmune disease |
| --- | --- |
| B. Systemic autoimmunity | |
| ACTH | ACTH deficiency |
| Aminoacyl-tRNA histidyl synthetase | Myositis, dermatomyositis |
| Aminoacyl-tRNA synthetase (several) | Polymyositis, dermatomyositis |
| Cardiolipin | SLE |
| Carbonic anhydrase II | SLE, Sjögren syndrome, systemic sclerosis |
| Collagen (multiple types) | Rheumatoid arthritis (RA), SLE, progressive systemic sclerosis |
| Centromere-associated proteins | Systemic sclerosis |
| DNA-dependent nucleosome-stimulated ATPase | Dermatomyositis |
| Fibrillarin | Scleroderma |
| Fibronectin | SLE, RA, morphea |
| Glucose-6-phosphate isomerase | RA |
| β32-Glycoprotein I (β32-GPI) | Primary antiphospholipid syndrome |
| Golgin (95, 97, 160, 180) | Sjögren Syndrome, SLE, RA |
| Heat shock protein | Various immune-related disorders |
| Hemidesmosomal protein 180 | Bullous pemphigoid, herpes gestationis, cicatricial pemphigoid |

Methods of Treatment

The soluble CD52 glycoprotein, fusion protein, polynucleotide, vector, cell, cell populations, cell medium and pharmaceutical composition described herein, and any agent capable of increasing the level of expression of CD52 in a cell, may be used to suppress effector T-cell function, inflammation or sepsis. Thus, the soluble CD52 glycoprotein, fusion protein, polynucleotide, vector, cell, cell populations, cell medium and pharmaceutical composition described herein, and any agent capable of increasing the level of expression of CD52 in a cell, may be used to treat any disease or condition mediated by effector T-cells, involving inflammation or sepsis.

In one example, the disease or condition mediated by effector T-cells may be an autoimmune disease, allograft rejection, a graft-versus-host reaction, or an allergic disease. The term "autoimmune disease" refers to any disease in which the body produces an immunogenic (i.e., immune system) response to some constituent of its own tissue. Autoimmune diseases can be classified into those in which predominantly one organ is affected (eg, hemolytic anemia and anti-immune thyroiditis), and those in which the autoimmune disease process is diffused through many tissues (eg, systemic lupus erythematosus). The autoimmune disease may be (but is not limited to) any one or more of insulin-dependent diabetes mellitus (or type 1 diabetes), insulin autoimmune syndrome, rheumatoid arthritis, psoriatic arthritis, chronic lyme arthritis, lupus, multiple sclerosis, inflammatory bowel disease including Crohn's disease, ulcerative colitis, celiac disease, autoimmune thyroid disease, autoimmune myocarditis, autoimmune hepatitis, pemphigus, anti-tubular basement membrane disease (kidney), familial dilated cardiomyopathy, Goodpasture's syndrome, Sjogren's syndrome, myasthenia gravis, polyendocrine failure, vitiligo, peripheral neuropathy, autoimmnune polyglandular syndrome type I, acute glomerulonephritis, adult-onset idiopathic hypoparathyroidism (AOIH), alopecia totalis, Hashimoto's thyroiditis, Graves' disease, Addison's disease, chronic beryllium syndrome, ankylosing spondylitis, juvenile dermatomyositis, polychondritis, scleroderma, regional enteritis, distal ileitis, granulomatous enteritis, regional ileitis, and terminal ileitis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barr syndrome, hemochromatosis, Henoch-Schonlein purpura, idiopathic IgA nephropathy, insulin autoimmune syndrome, juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, inflammatory bowel disease, osteoarthritis, thyroiditis, and others. In one example, the autoimmune disease is type 1 diabetes. In another example, the autoimmune disease is rheumatoid arthritis. In another example, the condition is an allograft rejection or a graft-versus-host reaction. Thus, the methods disclosed herein may comprise administering any one or more of the soluble CD 52 glycoprotein, fusion protein, polynucleotide, vector, cell, cell populations, cell medium, agent and pharmaceutical composition to a transplant recipient.

The allergic disease may be (but is not limited to) any one or more of a food allergy, airborne allergy, house dust mite allergy, cat allergy, or bee venom allergy, or other allergy.

Inflammation may arise as a response to an injury or abnormal stimulation caused by a physical, chemical, or biologic agent. An inflammation reaction may include the local reactions and resulting morphologic changes, destruction or removal of injurious material such as an infective organism, and responses that lead to repair and healing.

Inflammation occurs in inflammatory disorders. The term "inflammatory" when used in reference to a disorder refers to a pathological process which is caused by, resulting from, or resulting in inflammation that is inappropriate or which does not resolve in the normal manner Inflammatory disorders may be systemic or localized to particular tissues or organs. Inflammation is known to occur in many disorders (some of which are autoimmune diseases) which include, but are not limited to, Systemic Inflammatory Response (SIRS); Alzheimer's Disease (and associated conditions and symptoms including: chronic neuroinflammation, glial activation; increased microglia; neuritic plaque formation; Amyotrophic Lateral Sclerosis (ALS), arthritis (and associated conditions and symptoms including, but not limited to: acute joint inflammation, antigen-induced arthritis, arthritis associated with chronic lymphocytic thyroiditis, collagen-induced arthritis, juvenile arthritis, rheumatoid arthritis, osteoarthritis, prognosis and *streptococcus*-induced arthritis, spondyloarthropathies, and gouty arthritis), asthma (and associated conditions and symptoms, including: bronchial asthma; chronic obstructive airway disease, chronic obstructive pulmonary disease, juvenile asthma and occupational asthma); cardiovascular diseases (and associated conditions and symptoms, including atherosclerosis, autoimmune myocarditis, chronic cardiac hypoxia, congestive heart failure, coronary artery disease, cardiomyopathy and cardiac cell dysfunction, including: aortic smooth muscle cell activation, cardiac cell apoptosis and immunomodulation of cardiac cell function); diabetes (and associated conditions, including autoimmune diabetes, insulin-dependent (Type 1) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations such as viral and other types of hepatitis, cholesterol gallstones and hepatic fibrosis; HIV infection (and associated conditions, including—degenerative responses, neurodegenerative responses, and HIV associated Hodgkin's Disease); Kawasaki's Syndrome (and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis); nephropathies (and associated diseases and conditions, including diabetic nephropathy, endstage renal disease, acute and chronic glomerulonephritis, acute and chronic interstitial nephritis, lupus nephritis, Goodpasture's syndrome, hemodialysis survival and renal ischemic reperfusion injury); neurodegenerative diseases or neuropathological conditions (and associated diseases and conditions, including acute neurodegeneration, induction of IL-I in aging and neurodegenerative disease, IL-I induced plasticity of hypothalamic neurons and chronic stress hyperresponsiveness, myelopathy); ophthalmopathies (and associated diseases and conditions, including diabetic retinopathy, Graves' ophthalmopathy, inflammation associated with corneal injury or infection including corneal ulceration, and uveitis), osteoporosis (and associated diseases and conditions, including alveolar, femoral, radial, vertebral or wrist bone loss or fracture incidence, postmenopausal bone loss, fracture incidence or rate of bone loss); otitis media (adult or paediatric); pancreatitis or pancreatic acinitis; periodontal disease (and associated diseases and conditions, including adult, early onset and diabetic); pulmonary diseases, including chronic lung disease, chronic sinusitis, hyaline membrane disease, hypoxia and pulmonary disease in SIDS; restenosis of coronary or other vascular grafts; rheumatism including rheumatoid arthritis, rheumatic Aschoff bodies, rheumatic diseases and rheumatic myocarditis; thyroiditis including chronic lymphocytic thyroiditis; urinary tract infections including chronic prostatitis, chronic pelvic pain syndrome and urolithiasis; immunological disorders, including autoimmune diseases, such as alopecia aerata, autoimmune myocarditis, Graves' disease, Graves ophthalmopathy, lichen sclerosis, multiple sclerosis, psoriasis, systemic lupus erythematosus, systemic sclerosis, thyroid diseases (e.g. goitre and struma lymphomatosa (Hashimoto's thyroiditis, lymphadenoid goitre); lung injury (acute hemorrhagic lung injury, Goodpasture's syndrome, acute ischemic reperfusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical wounds and spinal cord injuries), septicaemia, acute phase response (e.g. febrile response), general inflammatory response, acute respiratory distress response, acute systemic inflammatory response, wound healing, adhesion, immuno-inflammatory response, neuroendocrine response, fever development and resistance, acute-phase response, stress response, disease susceptibility, repetitive motion stress, tennis elbow, and pain management and response.

The methods of treatment may comprise administering a therapeutically effective amount of any one or more of the soluble CD52 glycoprotein, fusion protein, polynucleotide, vector, cell, cell populations, cell medium or pharmaceutical composition described herein, or any agent capable of increasing the level of expression of CD52 in a cell, to a subject in need thereof.

The 'therapeutically effective amount' may be determined by a clinician and may vary from one patient to another, depending on factors such as age, weight, gender, and other factors.

Diagnostic Methods

Based on the inventors' finding that soluble CD52 is a mediator of Treg function, the present disclosure also provides methods of determining a subject's susceptibility to any disease or condition mediated by effector T-cells, inflammation or sepsis as described herein. The diagnostic methods may be based on the detection of any one or more of the level of soluble CD52, the frequency of $CD52^{hi}$ cells and the function of $CD52^{hi}$ cells in a sample taken from the subject.

The level of soluble CD52 may be determined by any suitable method known in the art. For example, the level of soluble CD52 may be determined by immunoassay, using antibodies that bind to soluble CD52. Suitable antibodies include the humanized rat monoclonal antibody CAMPATH-1G, fluorescent-labelled mouse monoclonal antibodies to human CD52 (such as CF1D12), rabbit polyclonal antibody to CD52 (Santa Cruz Biotechnology, Santa Cruz, Calif., USA) and others.

The frequency of $CD52^{hi}$ cells may be detected, for example, by detecting the level of cell membrane bound CD52 in the sample, by detecting the level of expression of CD52 protein in the sample, and/or by detecting the level of expression of CD52 mRNA in the sample.

The function of $CD52^{hi}$ cells may be determined using any suitable method, including any of the methods disclosed herein.

The diagnostic methods may be performed on any suitable sample taken from the subject. In one example, the sample is taken from a mammalian subject such as a human subject, and may originate from a number of sources, including for example, peripheral blood mononuclear cells (PMBC), leukopheresis or apheresis blood product, bone marrow, cord blood, liver, thymus, tissue biopsy, tumour, lymph node tissue, gut associated lymphoid tissue, mucosa associated lymph node tissue, spleen tissue, or any other lymphoid tissue, or from any disease site, including the pancreas. In a preferred embodiment, the cell sample originates from PBMC from a blood sample obtained from the peripheral blood of a subject.

The diagnostic methods may comprise detecting the level of any one or more of soluble CD52, the frequency of $CD52^{hi}$ cells and the function of $CD52^{hi}$ cells in a sample comprising PMBCs which have been contacted with an antigen. Thus, the methods may comprise a step of contacting the sample with an antigen. In one example, the antigen may be an autoantigen.

In one particular application of the diagnostic methods disclosed herein, the level of soluble CD52, the frequency of $CD52^{hi}$ cells and/or the function of $CD52^{hi}$ cells may be determined in order to identify a subject's suitability for entry into a drug screening trial. Thus, if a subject exhibits a lower level of soluble CD52 glycoprotein, a lower frequency of $CD52^{hi}$ cells, and/or a decreased function of $CD52^{hi}$ cells, that subject may be identified as particularly suitable for inclusion in a screening trial for a drug intended to be used in the treatment of any disease or condition mediated by effector T-cells, inflammation, or sepsis, as described herein. In one example, the screen may be performed in order to identify putative anti-diabetic drugs (in particular, anti-type 1 diabetes drugs).

The diagnostic methods described herein may further comprise a step of determining a reference level of soluble CD52, of the frequency of CD52$^{hi}$ cells and/or of the function of CD52$^{hi}$ cells from a sample taken from one or more healthy subjects. Alternatively, the reference level may be predetermined. Comparing the level of soluble CD52, frequency of CD52$^{hi}$ cells and/or function of CD52$^{hi}$ cells in a sample taken from a subject to the reference level can indicate the subject's susceptibility to any disease or condition mediated by effector T-cells, inflammation, or sepsis, as described herein. For example, if the level of soluble CD52, frequency of CD52$^{hi}$ cells and/or function of CD52$^{hi}$ cells in the sample taken from a subject is lower than the reference level, that subject may be deemed to be more susceptible to developing a disease or condition mediated by effector T-cells, inflammation, or sepsis, as described herein. A greater difference between the sample level and the reference level may indicate a greater susceptibility of the subject to developing a disease or condition mediated by effector T-cells, inflammation, or sepsis, as described herein. It will be appreciated that the exact values indicating an increased risk of a subject developing a disease or condition mediated by effector T-cells, inflammation, or sepsis, will vary depending on a number of factors including the particular disease or condition being diagnosed, the sample used for the diagnosis, the population of healthy individuals used to prepare the reference level, and other factors as will be understood by a person skilled in the art.

The present disclosure also provides a method of screening for an agent capable of suppressing effector T-cell function and/or an immune response, the method comprising contacting a cell or cell population described herein (for example, a CD52$^{hi}$ cell or cell population) with a test agent and subsequently detecting the level of soluble CD52, the frequency of CD52$^{hi}$ cells and/or the function of CD52$^{hi}$ cells, wherein a higher level of soluble CD52 glycoprotein, a higher frequency of CD52$^{hi}$ cells, and/or an enhanced function of CD52$^{hi}$ cells after contact with the test agent indicates that the test agent may be potentially suitable for use as an agent capable of suppressing effector T-cell function and/or an immune response.

In another embodiment, the present disclosure also provides a method of identifying an agent capable of mimicking the effector T-cell-suppressing, and/or immune system suppressing, function of a soluble CD52 glycoprotein, the method comprising contacting a cell or cell population described herein (for example, a CD52$^{hi}$ cell or cell population) with a test agent and subsequently detecting the level of soluble CD52, the frequency of CD52$^{hi}$ cells and/or the function of CD52$^{hi}$ cells, wherein a lower level of soluble CD52 glycoprotein, a lower frequency of CD52$^{hi}$ cells, and/or a reduced function of CD52$^{hi}$ cells after contact with the test agent indicates that the test agent is capable of mimicking the effector T-cell-suppressing, and/or immune system suppressing, function of a soluble CD52 glycoprotein.

The invention will now be further described with reference to the following, non-limiting examples.

EXAMPLES

Experimental Procedures

Blood Donors

Venous blood drawn into sodium heparin tubes was obtained with informed consent and Human Research Ethics Committee approval from 5 healthy young adults (3 males, 2 females) and a young adult male at risk for T1D, all known to have blood T-cell responses to GAD65. All donors had been vaccinated to tetanus toxoid. Peripheral blood mononuclear cells (PBMCs) were isolated on Ficoll/Hypaque (Amersham Pharmacia Biotech AB, Uppsala, Sweden), washed twice in human tonicity phosphate buffered saline (PBS) and resuspended in Iscove's modified Dulbecco's medium (Gibco, Melbourne, Australia) containing 5% pooled, heat-inactivated human serum, 100 mM non-essential amino acids, 2 mM glutamine and $5 \times 10^{-5}$ M 2-mercaptoethanol (complete Iscove's modified Dulbecco's medium [IMDM]).

Antibodies and Other Reagents

Reagents and suppliers were as follows: fluorescent-labelled mouse monoclonal antibodies to human CD52 (clone CF1D12) and CD24 (clone SN3) (Caltag), FoxP3, GITR, ICOS, CD25, CD127 and human Siglec-10 (clone 5G6) (Biolegend, San Diego, Calif., USA); mouse IgG3 (Caltag); rabbit polyclonal antibody to CD52 (Santa Cruz Biotechnology, Santa Cruz, Calif., USA); HRP-conjugated horse anti-rabbit IgG and anti-mouse IgG (Cell Signaling, Arundal, QLD, Australia); ECL reagent (GE Healthcare, Rydalmere, NSW, Australia), humanized rat monoclonal antibody (CAMPATH-1G) to CD52 (Bayer Healthcare, Pymble, NSW, Australia), mouse monoclonal antibodies to human IFN-γ (Mabtech, Sydney, NSW, Australia), and IL-10Ra (clone 37607), goat anti-human TGF-PRII and goat affinity-purified antibody to human Siglec-10 and recombinant human Siglec-10-Fc (R & D Systems, Minneapolis, Minn.); IL-2 (NCIBRB Preclinical Repository, Rockville, Md.); synthetic human CD52 peptide (GL Biochem, Shanghai); indomethacin, nitro-L-arginine methylester, 1-methyl-dl-tryptophan, SCH58261 (adenosine A2A receptor antagonist) (Sigma-Aldrich, St. Louis, Mo., USA); carboxyfluorescein diacetate succinimidyl ester (CFSE) (Molecular Probes, Eugene, Oreg., USA); neuraminidase (C. perfringens type V) (Sigma-Aldrich, Castle Hill, Australia); $^3$H-thymidine (ICN, Sydney, Australia); 0.4 μm Corning Costar transwells (Crown Scientific, Minto, NSW, Australia); Protein G and A-Sepharose (WEHI Monoclonal Lab, Bundoora, Victoria Australia), phospholipase C (U7322) and D (1,10-phenanthroline) inhibitors (Sigma-Aldrich Pty. Ltd. NSW, Australia), phospholipase C (Molecular Probes, Eugene, Oreg., USA), PNGase F (New England Biolabs, Ipswich, Mass., USA), Strep-Tactin Sepharose (IBA GmbH Gottingen, Germany) Tetanus toxoid (TT) was generously provided by CSL (Parkville, Victoria, Australia). Recombinant GAD65 produced in Baculovirus and purified as described (Bach et al., 1997) was purchased from Dr Peter Van Endert, Hôpital Necker, Paris. The endotoxin concentration of the GAD65 stock solution, measured by Limulus lysate assay (BioWhittaker, Walkerville, Md., USA), was 1.2 EU/mg/ml. TT and GAD65 were used at concentrations of 10 Lyons flocculating units (LFU)/ml and 5 μg/ml, respectively, unless otherwise stated. Cytokines and soluble IL-2 receptor-α (CD25) were assayed in media by Milliplex MAP bead arrays (Abacus ALS, Brisbane, Australia).

Statistical Analysis

Replicates were expressed as mean±sem. Significance between groups was determined by unpaired (2-tail) Student

Example 1: Analysis of GAD65-Specific CD4$^+$ T-Cell Clones

Methods

GAD65-specific CD4$^+$ T-cell clones, previously generated and screened for GAD65-specific suppressor function, were thawed and cultured as described (Dromey et al., 2011). Initially, suppressor and non-suppressor clones were screened for surface markers against an array of solid phase antibodies (Medsaic Ptd Ltd, Sydney, Australia) (Belov et al., 2003). Clones (1×10$^6$) were taken directly from culture and analysed resting or after stimulation for 24 hrs with plate-bound anti-CD3 (5 μg/ml). For phenotyping by flow cytometry, cells were stained on ice with the appropriate concentrations of labelled antibodies. Staining for intracellular FoxP3 and intracellular CTLA-4 was combined.

Results

Screening pairs of autologous suppressor and non-suppressor clones for differences in surface phenotype using a CD antibody array revealed that activated suppressor clones were consistently found to have higher expression of CD52, a result which was confirmed by flow cytometry (see FIG. 1). Thus, CD52 was identified as a potential marker of Treg cells.

Example 2: Analysis of Blood CD4$^+$ CD52$^{hi}$ T-Cells

Methods

PBMCs stained with carboxyfluorescein succinimidyl ester (CFSE) were cultured in IMDM in 96-well round-bottom plates, without or with GAD65 or TT, at 2×10$^5$ in 200 μl in replicates of six. After 7 days, replicates were pooled, washed in 0.1% BSA-PBS and stained on ice with anti-human CD4-PE, -PECy7 or -APC and CD52-PE (clone CF1D12) antibodies. Viable (propidium-iodide negative) CFSE$^{dim}$ CD4$^+$ cells that had undergone division in response to GAD65 were sorted in a FACSAria (BD Biosciences, North Ryde, NSW, Australia) into fractions with the highest to the lowest CD52 expression, and single cells cloned as described (Dromey et al., 2011). Subsequently, in response to GAD65 or TT, CD52$^{hi}$ and CD52$^{lo}$ populations corresponding, respectively, to the upper 10% and lower 10% of CD52 expression on undivided CD4$^+$ cells were sorted for further study. These cut-offs were chosen because the majority of GAD65-specific suppressor clones generated were from the upper 10% of CD52$^+$ cells (see Table 1).

Using PBMCs from the same donor over 4 consecutive weeks, the inter-assay coefficient of variation of the CD52$^{hi}$ to CD52$^{lo}$ ratio in response to GAD65 was 21.8%. Resting PBMCs were sorted into CD4$^+$ CD52$^{hi}$ and CD52$^{lo}$ cells, and also collected unsorted as a control. In separate experiments, prior to CFSE labelling, PBMCs were depleted of CD25$^+$ cells by AutoMACS selection (Miltenyi Biotec); isotype-matched monoclonal antibodies were used for control 'depletions'.

The function of GAD65- or TT-activated CD52$^{hi}$ and CD52$^{lo}$ CD4$^+$ cells was analysed in two ways. First, sorted CD52$^{hi}$ or CD52$^{lo}$ cells were co-cultured with TT-activated CD4$^+$ T-cells at a 1:1 ratio (1×10$^4$/well) in 6 wells of a 96-well plate. Each well also contained 5×10$^4$ irradiated autologous PBMCs as APCs and TT to stimulate proliferation of the autologous TT-activated CD4$^+$ T-cells. GAD65 was added to 3 of the 6 wells to re-stimulate sorted cells. As a control, irradiated PBMCs were also cultured with or without GAD65. After 48 hrs, $^3$H thymidine (37 kBq) was added to each well, and the cells harvested 16 hrs later. Second, sorted CD52$^{hi}$ or CD52$^{lo}$ CD4$^+$ cells (5-20,000 each) were cultured alone or in combination at a 1:1 ratio in 6 replicate wells of a 96-well ELISpot plate (Millipore PVDF MultiScreen HTS) containing pre-bound anti-IFN-γ antibody. Each well also contained four times the number of irradiated autologous PBMCs as APCs. GAD65 or TT was added to 3 of the 6 wells to re-stimulate sorted cells. After 24 hrs, cells were removed by washing and spots developed by incubation with biotinylated second antibody, followed by streptavidin-alkaline phosphatase and BCIP/NBT colour reagent. Results were expressed as IFN-γ spots/5,000 CD4$^+$ cells.

Results

A majority (22/29, 76%) of GAD65-specific suppressor clones was found to be derived from GAD65-activated CD4$^+$ T-cells with the highest CD52 expression (upper 10%) (Table 1). Thus, suppressor clones appeared to be derived from primary blood CD52$^{hi}$ CD4$^+$ T-cells rather than being an artifact of the cloning conditions.

TABLE 1

Suppressor clones derived from GAD65-activated CD4$^+$ T-cells fractionated according to CD52 expression*

| CD52 fraction† (%) | Number of clones generated | GAD65-specific suppressor clones |
|---|---|---|
| Upper 5% | 86 | 9 (10.5) |
| Upper 10% | 94 | 13 (13.8) |
| Upper 20% | 87 | 5 (5.7) |
| Lower 80% | 60 | 2 (3.3) |

*PBMCs from a healthy individual known to have GAD65-reactive T-cells were labeled with CFSE and incubated with GAD65 for 7 days. From each CD52$^+$ fraction, 240 single, viable (Propidium-iodide negative) CFSE$^{dim}$ CD4$^+$ cells that had undergone division were FACS sorted into wells of 96-well plates and cloned as previous described (Dromey et al, 2001).
†Corresponding to CD52 expression on undivided CD4$^+$ T-cells As the majority of GAD65-specific CD4$^+$ suppressor clones were derived from divided cells with CD52 expression corresponding to the upper 10% on undivided CD4$^+$ cells this threshold could be used to define a CD52$^{hi}$ CD4$^+$ population after activation. When re-activated with GAD65, sorted CD52$^{hi}$ but not CD52$^{lo}$ CD4$^+$ cells suppressed proliferation of autologous TT-specific CD4$^+$ T-cells (FIG. 2A). To ensure that suppression was specific for CD52$^{hi}$ cells and not due to the method of their selection GAD65-activated CD4$^+$ cells were sorted for high expression of two other GPI-anchored glycoproteins, CD24 and CD59, as well as for CD62L, HLA-DR, CD80 and ICOS, but these populations did not suppress proliferation of TT-specific T-cells (data not shown).

Functional differences between sorted CD52$^{hi}$ and CD52$^{lo}$ CD4$^+$ T-cells after reactivation with GAD65 were also demonstrated by ELISpot assay. A lower proportion of CD52$^{hi}$ than CD52$^{lo}$ cells secreted IFN-γ and addition of CD52$^{hi}$ to CD52$^{lo}$ cells reduced the number of IFN-γ secreting cells in response to re-activation [compare CD52$^{hi}$ CD52$^{lo}$ (p<0.002) with CD52$^{lo}$+CD52$^{lo}$ cells (p<0.0002) in FIG. 2B]. Suppression was not unique to CD52$^{hi}$ CD4$^+$ T-cells activated by GAD65 and was also observed when tetanus toxoid (TT) was used as the activating antigen (FIG. 2C). Because T-cell responses to TT were stronger, subsequent studies mostly employed TT as antigen. Supplementation with a low concentration of IL-2 (10 U/ml) increased the number of both CD52$^{hi}$ and CD52$^{lo}$ IFN-γ secreting cells in response to reactivation, but did not alter suppression by CD52$_{hi}$ cells (FIG. 2C). CD52$^{hi}$ CD4$^+$ cells that were sorted from non-activated, polyspecific PBMCs exhibited weak, usually significant suppression of T-cells activated by GAD65 or TT (data not shown). However, after antigen activation, suppressor CD52$^{hi}$ CD4$^+$ cells were most likely derived from pre-existing CD52$^{hi}$ CD4$^+$ cells because depletion of these cells from resting PBMCs increased the response of residual T-cells to GAD65 (FIG. 2D).

Example 3: CD52$^{hi}$ CD4$^+$ T-Cells are Distinct from CD4$^+$ CD25$^+$ Treg Cells Methods PBMCs were labelled with anti-CD25α antibody and depleted of CD25$^{hi}$ cells on an AutoMACS column (84% compared to isotype control antibody 'depletion'). Cells were then labelled with CFSE and incubated with TT for 7 days before being sorted into CD52$^{hi}$ and CD52$^{lo}$ cells, reactivated by TT and analysed by ELISpot assay.

Results

Following depletion of CD25$^{hi}$ cells, the proportion of divided CD52$^{hi}$ CD4$^+$ cells in response to TT increased (18.1% versus 11.8% with control depletion) but their suppressor function after reactivation with TT remained unchanged (FIG. 3). Thus, suppressor CD52$^{hi}$ CD4$^+$ cells do not appear to be derived from the population of CD4$^+$ CD25$^+$ T-cells.

Example 4: Phenotypic Analysis of CD52$^{hi}$ CD4$^+$ T-Cells

Methods

Flow cytometric expression of (A) CD25α, (B) FoxP3, (C) surface and (D) intracellular CTLA-4, (E) GITR, (F) CD127, (G) CD24 and (H) CD59 on divided CD52$^{hi}$ (black line) and CD52$^{lo}$ (grey line) CD4$^+$ T-cells, following incubation of PBMCs with TT for 7 days. Staining by isotype control antibody is shown as grey fill. Results are representative of 5 individuals.

Results

CD4$^+$CD25$^+$ Treg cells have high expression of CD25, FoxP3, CTLA-4 and glucocorticoid-induced tumor necrosis factor receptor related protein (GITR) (Sakaguchi et al., 2008; Shevach, 2006) and low expression of CD127 (Seddiki et al., 2006; Liu et al., 2006). In contrast, except for higher expression of GITR, CD52$^{hi}$ CD4$^+$ T-cells had similar expression of CD25, FoxP3 and CTLA-4, and consistently higher expression of CD127, compared to CD52$^{lo}$ CD4$^+$ T-cells (FIG. 4). Expression of the GPI-anchored glycoprotein, CD24, structurally related to CD52 (Tone et al., 1999), was higher on CD52$^{hi}$ CD4$^+$ T-cells but this was not the case for GPI-anchored CD59 (FIG. 4) or CD73, or for CD103, CD40, β7 integrin, ICOS and PD-1 (data not shown). Thus, CD52$^{hi}$ CD4$^+$ T-cells are a novel population of suppressor cells which are not characterized by expression of markers used to define human CD4$^+$CD25$^+$ Treg cells, and which are detected in the context of activation by antigen, implying that they contribute to T-cell homeostasis during T-cell division.

Example 5: Gene Expression Analysis of CD52$^{hi}$ CD4$^+$ T-Cells

Methods

The expression of the CD52 gene and of genes for proteins found to have increased expression on CD52$^{hi}$ CD4$^+$ T-cells was investigated by quantitative real time RT-PCR. CFSE-labelled CD52$^{hi}$ and CD52$^{lo}$ CD4$^+$ T-cells were sorted from three individuals, 7 days after activation by GAD65. Total RNA was extracted from cells with the RNAeasy Mini Kit (Qiagen, Melbourne, Australia), treated with RNase-free DNase (Qiagen) and quantified with the Agilent 2100 Bioanalyser. cDNA was reverse transcribed from 10 ng RNA/reaction. Primers for PCR, designed with PrimerExpress software and synthesized by Sigma-Aldrich (Castle Hill, NSW, Australia), were:

```
CD52 F:
                                   (SEQ ID NO: 8)
CAA ACT GGA CTC TCA GGA CAA A

CD52 R:
                                   (SEQ ID NO: 9)
CAA CTG AAG CAG AAG AGG TGG A

FOXP3 F:
                                   (SEQ ID NO: 10)
ATG GTT TCT GAA GAA GGC AAA C

FOXP3 R:
                                   (SEQ ID NO: 11)
GGA CTA CTT CAA GTT CCA CAA CA

CTLA-4 F:
                                   (SEQ ID NO: 12)
AAC CTA CAT GAT GGG GAA TGA G

CTLA-4 R:
                                   (SEQ ID NO: 13)
TTA CAT AAA TCT GGG TTC CGT T

GITR F:
                                   (SEQ ID NO: 14)
GGG AAA TTC AGT TTT GGC TTC

GITR R:
                                   (SEQ ID NO: 15)
ACA GCG TTG TGG GTC TTG TT

CD127 F:
                                   (SEQ ID NO: 16)
CCT TTT GAC CTG AGT GTC GTC T

CD127 R:
                                   (SEQ ID NO: 17)
CGT CCA TTT GTT TTC ATC CTT T
```

Power SYBR Green PCR Master Mix was from Applied Biosystems. Triplicate samples of cDNA were subjected to 40 cycles of amplification in an ABI Prism 7900 instrument, according to the manufacturer's protocol. mRNA expression, normalized to endogenous β-actin expression, was quantified by the comparative critical threshold (Ct) method according to the formula 2-ΔΔCt, as described in the ABI User Bulletin 2 (docs.appliedbiosystems.com/pebiodocs/04303859.pdf).

Results

Consistent with the flow cytometric expression analysis, CD52, CD127 and GITR transcripts were higher in CD52$^{hi}$ cells than CD52$^{lo}$ cells (FIG. 5).

Example 6: Suppression by CD52$^{hi}$ Cells is not Influenced by the Level of Expression of CD24

Methods

In order to analyze expression of the structurally related CD24 GPI-anchored glycoprotein, CFSE-labelled PBMCs were incubated with TT for 7 days and sorted into CD52$^{hi}$CD24$^{lo}$, CD52$^{hi}$CD24$^{hi}$, CD52$^{lo}$CD24$^{lo}$ and CD52$^{lo}$CD24$^{hi}$ CD4$^+$ T-cells. Each population (5,000 cells) was incubated with sorted CD52$^{lo}$ responder cells (5,000 and irradiated PBMCs (20,000) and analysed by ELISpot assay. Results are mean+sem of triplicates.

Results

Expression of the GPI-anchored glycoprotein, CD24, structurally related to CD52 (Tone et al, 1999), was higher on $CD52^{hi}$ $CD4^+$ T-cells. Although antigen-activated $CD24^{hi}$ $CD4^+$ T-cells, unlike $CD52^{hi}$ $CD4^+$ T-cells, were not suppressive it was important to determine if CD24 better delineated $CD52^{hi}$ $CD4^+$ T-cells with suppressor function. TT-activated PBMCs were sorted into four distinct $CD4^+$ populations according to both CD52 and CD24 expression and then tested for suppressor function after re-activation with TT. This revealed that suppression by $CD52^{hi}$ cells was not influenced by expression of CD24 (FIG. 6).

Example 7: $CD52^{hi}$ Treg Function does not Require Cell-Cell Contact

Methods $^3$H-thymidine uptake (cpm) by TT-activated and sorted $CD52^{hi}$ and $CD52^{lo}$ $CD4^+$ cells either combined or separated by a semi-permeable 0.4 µm transwell and re-activated with TT. CFSE-labelled PBMCs were incubated with TT for 7 days and sorted into $CD52^{hi}$ and $CD52^{lo}$ $CD4^+$ cells. Sorted cells (100,000 each) were incubated with irradiated autologous PBMCs (400,000) and TT in 48-well plates; in the presence of the transwell both compartments contained irradiated PBMCs and TT. $^3$H-thymidine uptake by cells in the bottom compartment was measured after 48 hrs.

Results

The suppressor function of antigen-activated $CD52^{hi}$ $CD4^+$ T-cells was retained across a transwell without cell-cell contact (FIG. 7). Thus, the present disclosure demonstrates that $CD52^{hi}$ $CD4^+$ Treg suppression is mediated at least in part by a soluble mediator. As discussed in Vignali et al. (2008), inhibitory cytokines have previously been investigated as possible soluble mediators of Treg suppression, though results have been inconclusive and the general perception has remained that cell-cell contact is essential for Treg suppressor function. The results disclosed herein suggested that $CD52^{hi}$ $CD4^+$ T-cells either removed a soluble factor required for the function of responder T-cells or produced a soluble factor that suppressed responder T-cells.

Example 8: Analysis of IL-2 in $CD52^{hi}$ Treg Function

Methods

The role of IL-2 was investigated in a number of experiments including the use of quantitative real time RT-PCR to determine expression levels. In the quantitative RT-PCR analysis, total RNA was extracted from cells with the RNAeasy Mini Kit (Qiagen, Melbourne, Australia), treated with RNase-free DNase (Qiagen) and quantified with the Agilent 2100 Bioanalyser. cDNA was reverse transcribed from 10 ng RNA/reaction. Primers for PCR, designed with PrimerExpress software and synthesized by Sigma-Aldrich (Castle Hill, NSW, Australia), were:

IL-2α

(SEQ ID NO: 18)
'5 TACAGGATGCAACTCCTGTCTT, (SEQ ID NO: 19)
'3 GCTCCAGTTGTAGCTGTGTTTT;

IL-2713

(SEQ ID NO: 20)
'5 GCTGTTCTCCATGGCTCCCTAC, (SEQ ID NO: 21)
'3 GTCGGGCTTGATGATGTGCT;

IL-12a (SEQ ID NO: 22)
'5 CTCCAGAAGGCCAGACAAACTC, (SEQ ID NO: 23)
'3 CCAATGGTAAACAGGCCTCCAC.

Power SYBR Green PCR Master Mix was from Applied Biosystems. cDNA was subjected to 40 cycles of amplification in an ABI Prism 7900 instrument, according to the manufacturer's protocol. mRNA expression, normalized to endogenous β-actin expression, was quantified by the comparative critical threshold (Ct) method according to the formula 2-AACt, as described in the ABI User Bulletin 2 (docs.appliedbiosystems.com/pebiodocs/04303859.pdf).

Results

Consumption or degradation of IL-2 by $CD52^{hi}$ $CD4^+$ T-cells was considered an unlikely mechanism of suppression for several reasons: i) exogenous IL-2 did not overcome suppression (FIG. 2C); ii) quantitative RT-PCR revealed that IL-2 gene expression was actually higher in $CD52^{hi}$ cells; thus, 24 h after re-activation by GAD65 the expression of IL-2α mRNA in $CD52^{hi}$ relative to $CD52^{lo}$ cells was 1.54±0.15 (mean±sem, n=3); iii) IL-2 concentration in the medium of $CD52^{hi}$ cells was higher than for $CD52^{lo}$ cells, both resting (89.5±4.82 v 64.9±3.10 µg/ml) and after re-activation with GAD65 (138.7±4.16 v 82.4±1.78 µg/ml) (mean±sem, n=3; P=0.02, Kruskal-Wallis test); iv) in the media in which IL-2 was measured, soluble IL-2 receptor-α (CD25) was undetectable (data not shown). Thus, the removal of IL-2 was thought to be an unlikely mechanism of $CD52^{hi}$ Treg suppression.

Example 9: Analysis of Other Putative Mediators of $CD52^{hi}$ Treg Function

Treg suppression was then found to be unchanged in the presence of agents that block the action or production of factors reported to mediate suppression by $CD4^+$ Treg cells (Sakaguchi et al., 2008, 2009; Shevach, 2006, 2009; Vignali et al., 2008). These included neutralizing monoclonal antibodies to IL-10Rα or TGF-βRII singly or in combination (10 µg/ml each), the cyclooxygenase-2 (COX-2) inhibitor indomethacin (20 µM) (which blocks prostaglandin E2 production), the pan nitric oxide synthase inhibitor N(G)-monomethyl-L-arginine (800 µM) (which blocks nitric oxide production), the indoleamine-2,3-dioxygenase (IDO) inhibitor 1-methyl-dl-tryptophan (200 µM) (which blocks production of inhibitory tryptophan metabolites) and the adenosine A2A receptor antagonist SCH58261 (20 µM) (which blocks the action of adenosine) (data not shown). Recently, a novel suppressor cytokine, IL-35, a heterodimer of IL-27β (EBi3) and IL-12α (p35) subunits, was shown to be secreted by $CD4^+$ $CD25^+$ Treg cells (which also required cell-cell contact for suppression) (Collison et al., 2007). IL-35 was unable to be measured directly because antibodies to IL-35 or its receptor were not available. However, 24 h after re-activation by GAD65 the expression of IL-270 and IL-12α mRNA was lower in $CD52^{hi}$ than $CD52^{lo}$ $CD4^+$ cells (0.423±0.188 vs 1.38±0.224; mean±sem, n=3), indicating that IL-35 is unlikely to account for suppression by $CD52^{hi}$ $CD4^+$ T-cells.

Example 10: Soluble CD52 is a Mediator of CD52$^{hi}$ Treg Suppression

Methods

CFSE-labelled PBMCs were incubated with GAD65 for 7 days and sorted into CD52$^{hi}$ and CD52$^{lo}$ CD4$^+$ T-cells. Sorted cells were re-activated with GAD65 and media collected after 24 hrs. Media were concentrated 10-fold, fractionated by SDS-PAGE, transferred to a PDVF membrane and blotted with a rabbit polyclonal antibody to CD52 in order to detect the presence of soluble CD52 in the media.

The phospholipase C inhibitor U73122 was then analysed as a potential inhibitor of soluble CD52 production. CFSE-labelled PBMCs were incubated with TT for 7 days and sorted into CD52$^{hi}$ CD4$^+$ T-cells. Sorted cells were re-activated with TT and media collected after 24 hrs and subjected to immunoblotting as above. Separately, CFSE-labelled PBMCs were incubated with TT for 7 days and sorted into CD52$^{hi}$ and CD52$^{lo}$ CD4$^+$ T-cells, which then were incubated together (5,000 of each) in ELISpot plates with irradiated PBMCs (20,000) and TT±phospholipase C inhibitor U73122. Results are mean+sem of triplicates.

In addition, antibody to the carbohydrate moiety of CD52 was analysed as another potential inhibitor of suppression by TT-activated CD52$^{hi}$ CD4$^+$ T-cells. Procedures were as described for the phospholipase C inhibitor U73122 above except that cells in the ELISpot assay were incubated with or without TT and either 10 µg/ml anti-CD52 (CF1D12) or isotype control (IgG3) monoclonal antibody. Results (mean±sem) are representative of three independent experiments.

Results

Immunoblotting revealed that CD52 was present in the medium of CD52$^{hi}$CD4$^+$ T-cells that had divided in response to GAD65, and increased in quantity after their re-activation by GAD65 (FIG. 8A). The same result was found with TT as antigen and the phospholipase C inhibitor, U73122, added before re-activation with TT reduced the quantity of CD52 in the medium (FIG. 8B). Moreover, inhibition of phospholipase C reversed suppression by CD52$^{hi}$CD4$^+$ T-cells in a dose-dependent manner (FIG. 8C). The monoclonal antibody CF1D12, which interacts with the terminal carbohydrate on the CD52 peptide (Hale, 2001), prevented suppression by CD52$^{hi}$ of CD52$^{lo}$ CD4$^+$ T-cells (FIG. 8D). Together, these findings indicated that suppression by CD52$^{hi}$CD4$^+$ T-cells was due to soluble CD52, released by phospholipase cleavage in response to stimulation by antigen.

Example 11: Further Analysis of Soluble CD52 Effector Function

In considering a more abundant source of native soluble CD52 it was postulated that CD52 might be released spontaneously from some cell lines, such as the Daudi B lymphoblast cell line in which GPI biosynthesis is defective due to a deficiency of the PIGY gene product (Hu et al., 2009).

Methods

Media from sorted CD4$^+$CD52$^{hi}$ and CD52$^{lo}$ cells were collected 24 hrs after re-activation of cells with GAD65 or TT. Media from cell lines (Daudi, Raji, Jurkat and K562) were collected and concentrated 10-fold by freeze-drying. Samples were fractionated by SDSPAGE and transferred to a PVDF membrane. After blocking with 5% non-fat milk the membrane was incubated with rabbit polyclonal antibody to CD52 (1 ug/mL), washed, incubated with goat anti-rabbit IgG-horseradish peroxidase antibody and visualized by enhanced chemiluminescence.

Separately, PBMCs (200,000 cells) were cultured for 7 days in IMDM containing 20% Daudi cell conditioned medium with TT and either anti-CD52 (CF1D12) or isotype control antibody (10 µg/mL). To deplete soluble CD52, Daudi medium was incubated overnight with rabbit anti-CD52 polyclonal antibody (1 µg/ml medium) followed by precipitation with protein G-Sepharose for 1 h at 4° C. Results (mean±sem) are representative of three independent experiments.

Results

Screening several cell lines revealed the presence of CD52 in culture media of Daudi and K562 cells (FIG. 9A). Daudi medium suppressed TT-activated proliferation of PBMCs and suppression was reversed either by CF1D12 antibody or by immunodepletion (confirmed by immunoblotting) of CD52 (FIG. 9B), demonstrating that T-cell suppression was due to CD52 in the medium. CD52 was soluble and not present in exosomes or membrane particles because suppression was unaffected by centrifuging the medium at 100,000×g for 30 min (data not shown).

Example 12: Replication of Soluble CD52 Effector Function with CD52-Fc

Methods

To further explore the immunosuppressive function of soluble CD52, mature cell surface CD52 was cloned in a lentivirus vector as a fusion protein in-frame with the Fc fragment of immunoglobulin G and a C-terminal Strep-tag sequence for purification. An Fc only construct was cloned as a control. Constructs were expressed stably in Daudi cells or transiently in HEK293T cells and soluble recombinant proteins purified from medium by elution with desthiobiotin from Streptactin resin.

The scheme for constructing DNAs encoding fusion proteins is shown in FIG. 10. A mutated human IgG1 Fc fragment (Armour et al., 2003) joined to the signal peptide (SigP) sequence of CD52 was generated by PCR. This included a flexible GGSGG linker and two cleavage sites for Precission and Factor Xa proteases between the SigP and Fc fragment, and a Strep-tag II sequence for purification (Schmidt and Skerra, 2007) at the terminus of the Fc fragment. Primers, as designated in FIG. 10, used to generate and clone Fc constructs, were:

```
1F1:
                                        (SEQ ID NO: 24)
GAAGTTCTGTTCCAGGGGCCCATCGAAGGTCGTGGTG;

1R1:
                                        (SEQ ID NO: 25)
TCATTTTTCGAACTGCGGGTGGCTCCAGGCGCTTTTACCCGGAGACAG;

1F2:
                                        (SEQ ID NO: 26)
GGGGGTTCCGGGGGACTGGAAGTTCTGTTC;

1R2:
                                        (SEQ ID NO: 27)
CTTGATATCGAATTCTCATTTTTCGAACTG;

2F:
                                        (SEQ ID NO: 28)
CGCTGTTACGGATCCCCACCATGAAGCGCTTCCTC;

2R1:
                                        (SEQ ID NO: 29)
TCCACCGCTACCTCCTGAGGGGCTGCTGGT;
```

2R2:
(SEQ ID NO: 30)
TCCACCGCTACCTCCTGAGAGTCCAGTTTG.

A CD52-Fc construct comprising the CD52 SigP and extracellular domain (ECD) joined to the Fc fragment was generated by PCR. Primers used were: 2F, 2R1, 1F2 and 1R2. PCR products were digested with BamHI/EcoRI and ligated into the FTGW lentivirus vector (Herold M J et al., 2008). Clones were also verified by sequencing. Lentivirus particles were produced by CaPO4-mediated transfection of HEK293T cells seeded in 6 cm dishes with 10 ug of vector DNA together with three helper plasmids (pMDLRRE, pRSV-REV, and pVSV-g). Virus-containing cell culture medium was collected 48 hrs after transfection and passed through a 0.45 μm filter. One milliliter was used to transduce $1 \times 10^6$ Daudi cells grown in DME media supplemented with 10% FCS, 100 mM non-essential amino acids, 2 mM glutamine and $5 \times 10^{-5}$ M 2-mercaptoethanol. Cells were screened for the highest expression of protein by intracellular staining and flow cytometry. CD52-Fc or Fc control proteins were purified from medium by single-step affinity chromatography on Streptactin resin and elution with 2.5 mM desthiobiotin in 100 mM Tris-HCl, 150 mM NaCl, 1 mM EDTA, pH 8.0, as per the manufacturer's instructions. After dialysis, SDS-PAGE revealed single Coomassie blue-stained bands of predicted size whose specificity was confirmed by Western blotting.

Assays for Effects of Recombinant Fc Fusion Proteins

PBMCs ($2 \times 10^5$ cells/well) or purified CD4$^+$ T-cells ($5 \times 10^4$ cells/well) in complete IMDM medium-5% heat-inactivated pooled human serum were incubated in round-bottomed 96-well plates with or without 10 Lfu/ml TT and different concentrations of CD52-Fc or Fc proteins, in a total volume of 200 μl, at 37° C. in 5% CO$_2$-air for up to 7 days. $^3$H-thymidine (1 μCi/well) was added and after a further 18 h cells were harvested and radioactivity incorporated into DNA was measured by scintillation counting. Medium was sampled for assay of cytokines after 48 hr incubation. Dendritic cells (DCs) were isolated from PBMCs as described (Mittag et al., 2011). In brief, PBMCs were first enriched for DCs by magnetic bead depletion of cells labelled with antibodies to lineage markers (CD3, CD19, CD56). Cells were then stained with fluorescent antibodies to HLA-DR, CD11c, CD1b/c, CD304 and CD14 and flow sorted to purify CD1b/c+HLA-DR+CD11c+ conventional DC, CD304+HLA-DR+CD11c-plasmacytoid DC and CD14+CD16-CD11c+ monocytes. Purified DCs were pre-incubated with CD52-Fc or Fc protein at 3.3 μM for 30 min at 37° C. and washed twice. They were then serially diluted from 6000 cells/well in a 96-round bottom well plate and incubated with CFSE-labelled CD4$^+$ T-cells ($5 \times 10^4$/well) isolated from a different donor. After 6 days, the allogeneic T-cell response was measured as frequency of dividing CFSE$^{lo}$ cells determined by flow cytometry.

As described above, PBMCs (200,000) were cultured with TT for 7 days and purified CD4$^+$ T-cells (20,000) with anti-CD3 (100 ng/ml) and anti-CD28 (200 ng/ml) antibody for 48 hr, with 4 times the number of irradiated PBMCs in 200 μl round bottom wells, in the presence of recombinant CD52-Fc or Fc protein control protein at the indicated concentrations. $^3$H-thymidine uptake was measured over the final 16 h of incubation. Results (mean±sem of triplicates) are representative of six independent experiments.

Media from PBMCs activated with TT±3.3 μM CD52-Fc or Fc proteins were sampled after 48 h incubation and assayed for cytokines by multiplex bead array.

CD52-Fc (20 μg) was incubated with or without PNGase F (1,000 units) in 20 μl PBS overnight at 37° C. in order to cleave N-linked carbohydrate, and the reaction terminated by heating at 75° C. for 10 min Specifically, PNGase F cleaves asparagine-linked oligosaccharides between two N-acetylglucosamine subunits immediately adjacent to the asparagine residue to generate a truncated carbohydrate with one N-acetylglucosamine residue remaining on the asparagine. PBMCs were incubated with TT and treated or untreated CD52-Fc (final 2.5 μM) for 7 days at 37° C., and 3H-thymidine uptake then measured as above.

Results

With PBMCs, the proliferative response of T-cells to TT was suppressed by CD52-Fc in a dose-dependent manner (FIG. 11A), and CD52-Fc suppressed the secretion of cytokines typifying different T-cell lineages (FIG. 11C). The effect of CD52-Fc on T-cell function was direct because it suppressed proliferation of purified CD4$^+$ T-cells in response to T-cell receptor cross-linking with anti-CD3 antibody and co-stimulation with anti-CD28 antibody (FIG. 11B). Evidence that CD52-Fc did not require antigen-presenting cells for T-cell suppression was obtained by showing that exposure of purified dendritic cells to CD52-Fc did not affect their ability to elicit an allogeneic T-cell response (FIG. 13).

As shown (FIG. 8D), the ability of the CF1D12 antibody to block suppression by native CD52 implied that suppression may be mediated by the carbohydrate moiety of CD52. To examine its role in recombinant CD52-Fc, the N-linked carbohydrate was cleaved with the endoglycosidase PNGase F. This reduced the molecular weight of CD52-Fc from ~48 to ~30 kDa as predicted from loss of the carbohydrate and reduced its suppressive effect (FIG. 11D), confirming the role of the carbohydrate moiety in mediating the suppressive effect of soluble CD52.

Example 13: Further Analysis of CD52 Carbohydrate Function

Methods

To further explore the role of the CD52 carbohydrate moiety in mediating T-cell suppression, CD52-Fc (3.3 μM) was incubated with neuraminidase (1 unit) or carrier buffer only in 20 μl for 30 min at 37° C., as recommended by the supplier. PBMCs were then incubated with TT±neuraminidase-treated or untreated CD52-Fc (final 3.4 μM) in an ELISpot plate and developed after 24 h at 37° C. for IFN-γ spots. Separately, PBMCs were incubated in an ELISpot plate with TT and CD52-Fc (3.4 μM) and different concentrations of affinity-purified goat antibody to the extracellular domain of Siglec-10, or Fc (3.4 μM)±antibody, or different concentrations of recombinant Siglec-10-Fc, before non-adherent cells were transferred to an ELISpot plate for 24 hrs before development of IFN-γ spots.

In order to investigate the possibility that soluble CD52 may act via other Siglec receptors than Siglec-10, CD4$^+$ T-cells (20,000) were incubated in triplicate ELISpot plate wells at 37° C. with TT, together with CD52-Fc or Fc (3.4 μM each) and anti-human Siglec antibodies (10 μg/ml each) or recombinant human Siglec 2-Fc (20 μg/ml), as indicated in FIG. 12E. After 20 h, wells were washed and developed for IFN-γ spots.

Results

Treatment with neuraminidase to remove terminal sialic acids reduced suppression by CD52-Fc (FIG. 12A). The complex polylactosamine structure of the CD52 carbohydrate is proposed to terminate in α2-6 and possibly α2-3 sialic acids decorating galactose in β1-4 linkage with N-acetylglucosamine (Treumann et al., 1995). This sialoside sequence is recognized by human sialic acid binding Ig-like lectin-10 (Siglec-10), a cell surface transmembrane receptor and immunoglobulin superfamily member bearing two cytoplasmic immunoreceptor tyrosine-based inhibition motifs (ITIMs) (Munday et al., 2001; Crocker et al., 2007). Although Siglec-10 has not been detected on mouse T-cells (Crocker et al., 2007) and some other Siglecs are not expressed on human T-cells (Nguyen et al., 2006) we found that Siglec-10 was expressed on human CD4$^+$ T-cells and was upregulated by activation (FIG. 12B). Notably, suppression of T-cell function by CD52-Fc was reduced either by antibody to the extracellular domain of Siglec-10 (FIGS. 12C, 12E) or by soluble recombinant Siglec-10-Fc (FIG. 12D). The same concentrations of Siglec-10-Fc also reduced suppression by CD52$^{hi}$CD4$^+$ T-cells (data not shown), indicating that both recombinant and native CD52 recognize Siglec-10. T-cell suppression by CD52-Fc was not reduced to the same extent by antibodies to other Siglecs than Siglec-10 or by recombinant human Siglec 2-Fc. These findings show that suppression by CD52 could be accounted for at least in part by its interaction with Siglec-10.

Example 14: CD52$^{hi}$ T-Cells Protect Against Autoimmune Disease

Materials and Methods
Mice

C57/Bl6, NODLt and RIP.B7/NODSCID mice were bred and maintained at the Walter and Eliza Hall Institute of Medical Research. OVA-specific class I restricted TCR transgenic mice (Hogquist et al., 1993) and OVA-specific class II restricted TCR transgenic mice (Barnden et al., 1998) have been previously described. Foxp3$^{GFP}$ reporter mice were provided by Dr Yifan Zhang.
Reagents, Antibodies and Flow Cytometry Cells were cultured in RPMI media supplemented with 10% FCS, 1:100 GIBCO™ GlutaMAX™-I Supplement (Invitrogen), 1:1000 2-mercaptoethanol (Sigma), 1:100 NEAA (gibco). Monoclonal anti-CD52 antibodies were obtained from MBL International, clone BTG-2, PE conjugation or unlabeled. Polyclonal anti-CD52 antibody obtained from Santa Cruz Biotechnology, Inc (sc27555) was used for Western Blot analysis. Monoclonal anti-CD4 (L3T4, clone GK1.5) and anti-CD8a (Ly-2, clone 53-6.7) antibodies were obtained from eBiosciences. Anti-CD25 (clone 3c7) was obtained from BioLegend. CD3-FITC antibody, FoxP3 staining kit was obtained from eBioscience. Anti-CD3 (clone 2c11), anti-CD28 (clone 37.51) and isotype control monoclonal antibodies were from WEHI Monoclonal Antibody Lab. Flow cytometric analyses were done on a FACSAria with the FACS Diva software. Cells were sorted with a MoFlow cell sorter (Cytomation, Fort Collins, Colo.).
Cell Isolation Spleens were harvested and passed through a 70 μm mesh, treated with erythrocyte lysis buffer and washed. For activation of cells, splenocytes were cultivated on plate bound anti-CD3 (2 μg/ml) plus soluble anti-CD28 (1 μg/ml) for 3 days. OTI or OTII splenocytes were incubated with 0.5 μg/ml OTI or 5 μg/ml OTII peptide for 4 days before analysed. For cell sorting experiments, naïve or activated splenocytes from C57/Bl6, OTI or OTII, NODLt or Foxp3-GFP mice were labelled with either CD3-FITC (eBioscience), CD4-APC (eBioscience), CD8-APC (eBisoscience) and CD52-PE (MBL International). Labelled cells were separated with a MoFlow Cytometer and purity was ~95%. Isolated cells were either used for RNA purification, for T-cell proliferation assays or in vivo experiments.
Proliferation Assays Sorted naïve or activated CD4$^+$CD52$^{hi}$ or CD8$^+$CD52$^{hi}$ T-cells (2×10$^4$, in transwell experiments 1×10$^5$) were cultured with CD4$^+$CD52$^{lo}$ or CD8$^+$CD52$^{lo}$ T-cells at a ratio of 1:1 and stimulated with 1 μg/ml soluble anti-CD3 (2c11) plus (8×10$^4$, in transwell experiment 4×10$^5$) irradiated T-cell depleted APCs (2000 rad irradiation dose). 0.4 μM transwells (Corning, polycarbonate membrane transwell inserts Cat No 3413) were placed in between cells. In blocking experiments, 15 μg/ml anti-CD52 (rat IgG2a, MBL International) or isotype control was added. Proliferation assays were performed for 72 h in 96 well round bottom plates in a final volume of 200 μl RPMI medium that contained 10% fetal calf serum. 1 μCi/well [$^3$H] thymidine was added for the last 10 hours of the experiment and thymidine incorporation was measured by scintillation counting. Alternatively, CFSE labelled responder cells were used as readout for proliferation. Naïve splenocytes or CD4$^+$CD52$^{lo}$ or CD8$^+$CD52$^{lo}$ T-cells were resuspended in warm PBS+0.1% BSA at a cell number of 10×10$^6$ per ml. 5 μM CFSE was added and quickly resuspended. Cells were incubated at 37 degrees for 5 min before washed 3 times with cold buffer containing at least 10% BSA or FCS. CFSE labelled responder cells were incubated with CD4$^+$CD52$^{hi}$ or CD8$^+$CD52$^{hi}$ T-cells (plus additional controls) for up to 7 days and analysed using the FACS Aria.
Two Colour Assay CD4$^+$CD52$^{hi}$ or CD8$^+$CD52$^{hi}$ T-cells were stained with the cell division marker PKH.26 (Sigma) according to manufacturers recommendations. Briefly, up to 1×10$^7$ cells were resuspended in Diluent C (provided by the kit) and mixed with 2 μM PKH.26 for 4 min at room temperature. Cells were washed 3 times with buffer containing at least 10% FCS. Responding CD4$^+$CD52$^{lo}$ or CD8$^+$CD52$^{lo}$ T-cells were stained with CFSE as described above. Cells were cultivated alone or together for 4-6 days.
Realtime RT-PCR Total RNA was prepared from sorted T-cells using the RNeasy kit from Qiagen. The cDNA was synthesized using oligo-dT primers (Qiagen, 0.4 μg/μl) and M-MLV reverse transcriptase (4000 U, Applied Biosystems), following the manufacturers recommendations. Realtime RT-PCR was performed in an ABI PRISM 7900 cycler (Applied Biosystems) using a Quantitect SYBR Green PCR Kit (Qiagen, Cat No 204143) and specific primers optimised to amplify 100-150 bp fragments of different genes. A threshold was set in the linear part of the amplification curve and the number of cycles needed to reach the threshold was calculated for every gene. Relative mRNA expression was determined by normalization to a reference gene (b-Actin or RPS9).
Primer sequences are:

```
CD52
                                    (SEQ ID NO: 31)
FORW-GTT GTG ATT CAG ATA CAA ACA GGA (SEQ ID NO: 32)
REV-AGG TAT TGG CAA AGA AGA GGA A

IL-2
                                    (SEQ ID NO: 33)
FORW-TCA AGC TCC ACT TCA AGC TCT AC
```

-continued

REV- CCT GTA ATT CTC CAT CCT GCT C (SEQ ID NO: 34)

IL-4
FORW-TGA GAG AGA TCA TCG GCA TTT T (SEQ ID NO: 35)

REV-CTC TCT GTG GTG TTC TTC GTT G (SEQ ID NO: 36)

IL10
FORW-TCG GAA ATG ATC AGT TTT TAC C (SEQ ID NO: 37)

REV-ATC CTG AGG GTC TTC AGC TTC (SEQ ID NO: 38)

IL-13
FORW-GAG-CTG-AGC-AAC-ATC-ACA-CAA (SEQ ID NO: 39)

REV-AATCCAGGGCTACACAGAACC (SEQ ID NO: 40)

FoxP3
FORW-ATG-TTC-GCC-TAC-TTC-AGA-AAC-C (SEQ ID NO: 41)

REV-CAA-ATT-CAT-CTA-CGG-TCC-ACA-C (SEQ ID NO: 42)

CD127
FORW-GCC CAC CAG AAA CAG TTA GAA G (SEQ ID NO: 43)

REV-AGT CAG GGG ACC TAG AGG AAA G (SEQ ID NO: 44)

CTLA-4
FORW-AGT TTC CTG GTC ACT GCT GTT T (SEQ ID NO: 45)

REV-TTT TCA CAT TCT GGC TCT GTT G (SEQ ID NO: 46)

FASLG
FORW-CGG-TGG-TAT-TTT-TCA-TGG-TTC-T (SEQ ID NO: 47)

REV-TGA-TAC-TTT-AAG-GCT-TTG-GTT-GG (SEQ ID NO: 48)

TGFβ1
FORW-TAT GCT TCA GCT CCA CAG AGA A (SEQ ID NO: 49)

REV-CAG ACA GAA GTT GGC ATG GTA G (SEQ ID NO: 50)

TGFb2
FORW-TAA GAG GGA TCT TGG ATG GAA A (SEQ ID NO: 51)

REV-CTG AGG ACT TTG GTG TGT TGA G (SEQ ID NO: 52)

IFNg
FORW-CAA-AAG-GAT-GGT-GAC-ATG-AAA-A (SEQ ID NO: 53)

REV-TTG CTG TTG CTG AAG AAG GTA G (SEQ ID NO: 54)

IL-12alpha
FORW-TCA CGC TAC CTC CTC TTT TTG G (SEQ ID NO: 55)

REV-CAT CTG TGG TCT TCA GCA GGT TT (SEQ ID NO: 56)

Ebi3
FORW-CCT TCC CGG ACA TCT TCT CTC T (SEQ ID NO: 57)

REV-GCA ATA CTT GGC ATG GGG TTT (SEQ ID NO: 58)

RARA
FORW - GGA CAA GAA CTG CAT CAT CAA C (SEQ ID NO: 59)

REV-GCT TGG GTG CCT CTT TCT TC (SEQ ID NO: 60)

GITR
FORW-CCT-AGG-TCA-GCC-GAG-TGT-AGT-T (SEQ ID NO: 61)

REV-CAC-ATA-TGC-ACC-TTT-CTT-TTG-G (SEQ ID NO: 62)

GRANZMB
FORW-TCC TTA TTC GAG AGG ACT TTG TG (SEQ ID NO: 63)

REV-CTG GGT CTT CTC CTG TTC TTT G (SEQ ID NO: 64)

ALDH1A2
FORW-ACA GGA GAG CAA GTG TGT GAA G (SEQ ID NO: 65)

REV-TCC ACA CAG AAC CAA GAG AGA A (SEQ ID NO: 66)

ACTIN
FORW-GAT CTG GCA CCA CAC CTT CT (SEQ ID NO: 67)

REV-GGG GTG TTG AAG GTC TCA AA (SEQ ID NO: 68)

Adoptive Transfer of $CD52^{hi}$ Depleted Splenocytes into NOD Recipients $CD52^{hi}$ depleted total splenocytes or splenocytes depleted of CD3+, $CD4^+$ or $CD8^+CD52^{hi}$ T-cells were injected iv into recipient mice. Recipient mice were either irradiated male NOD mice (8 week old male NOD mice, 750 rad irradiation dose, 4 hours before transfer of 1 to $1.2 \times 10^7$ cells) or 8-week old RIP.B7/NOD.SCID mice, receiving $2 \times 10^6$ cells. Mice were monitored for signs of diabetes measuring urine glucose 3 times a week using Diastix from Bayer. If urine glucose exceeds 20 mM, blood glucose is measured. Mice are designated diabetic if consecutive blood glucose readings are above 20 mM glucose.

Insulitis Score 4 weeks postadoptive transfer of cells mice were sacrificed. Pancreata were harvested and fixed overnight in Bouin's solution and then transferred to 70% ethanol. Fixed pancreata were embedded in paraffin blocks, a minimum of 12 8-μm sections were cut at least 150 μm apart. The sections were stained with haematoxylin-eosin and evaluated for incidence and severity of insulitis in light microscopy independently by two investigators. A minimum of 10 islets from each mouse were observed and the degree of mononuclear cell infiltration was scored using the following ranking: 0=no infiltration; 1=peri-ductal infiltrate; 2=peri-islet infiltrate; 3=intra-islet infiltrate; 4=beta cell destruction.

Results

Transfer of $CD52^{hi}$-depleted splenic lymphocytes from 8 week-old NOD mice into NOD.scid mice lead to rapid onset of diabetes; non-depleted cells had no effect (FIG. 14). Transfer of $CD52^{hi}$-depleted $CD3^+$ T-cells accelerated diabetes onset, but was not as efficient as the depletion of total lymphocyte CD52$^{hi}$ cells (FIG. 15). Thus, CD52$^{hi}$ lymphocytes were shown to protect against autoimmune diabetes.

Example 15: The Frequency of CD52$^{hi}$ CD4$^+$ T-Cells Generated in Response to Simulation by GAD65 is Impaired in Type 1 Diabetes Methods PBMCs stained with CFSE were cultured with GAD65 or TT for 7 days before determination of CD52$^{hi}$ CD4$^+$ T-cell frequency by flow cytometric analysis.

Results

Individuals with and at risk for type 1 diabetes have fewer CD52$^{hi}$CD4$^+$ T-cells than healthy individuals in response to GAD65 but not TT (FIG. 16). The horizontal bar is the median for each group. Overall P values for analysis of variance were determined by the Kruskal-Wallis test; Dunn's multiple comparison test then revealed significant differences between both Pre-T1D and T1D compared Healthy or T2D at P<0.05.

Example 16: T-Cell Suppression by CD52$^{hi}$ CD4$^+$ Cells Generated in Response to GAD65 is Impaired in Pre-Clinical Type 1 Diabetes Methods CFSE-labelled PBMCs from individuals with islet cell autoantibodies at risk for type 1 diabetes were incubated with GAD65 for 7 days and sorted into CD52$^{hi}$ and CD52$^{lo}$ CD4$^+$ T-cells according to the methods described herein. Sorted cells (5,000) were incubated in ELISpot plates with irradiated PBMCs (20,000).

Results

As shown in FIG. 17, suppressor function of CD52$^{hi}$ CD4$^+$ cells generated in response to GAD65 is impaired in comparison to suppressor function of CD52$^{hi}$ CD4$^+$ cells generated in response to TT. Results are representative of 6 at-risk subjects. Thus, CD52$^{hi}$ CD4$^+$ cell suppressor function is impaired in pre-clinical T1D.

Example 17: Soluble CD52 Dramatically Reduces Blood Glucose Levels in NOD Mice

Methods Female NOD mice were monitored by weekly testing for urine glucose and diabetes was diagnosed in mice with a positive urine test by a blood glucose concentration >14 mM. As soon as hyperglycemia was confirmed mice were given either CD52-Fc or Fc, 20 µg i.p., six doses on alternate days, and their blood glucose concentrations then monitored twice weekly.

Results

Soluble CD52-Fc was shown to reduce blood glucose levels (FIG. 18). As shown, administration of CD52-Fc had a rapid and significant effect to reduce blood glucose levels, demonstrating the suitability of soluble CD52 as a therapeutic for the treatment of autoimmune diseases such as type 1 diabetes.

Example 18: Development of Diabetes in NOD.SCID Mice after Transfer from Diabetic NOD Mice of Splenocytes Treated Ex Vivo with hCD52-Fc or Fc Methods 5×10$^6$ rhCD52 Fc- or Fc-treated diabetic NOD splenocytes were injected into NOD.SCID mice. Splenocytes from female diabetic mice were isolated and incubated with either 50 ug/ml recombinant human CD52-Fc or Fc protein for 1.5 hr in 'CD52 buffer' (Tris buffered saline+2 mM of MgCl2, CaCl2 and MnC12+5 mM glucose+1% mouse serum). Cells were re-suspended in PBS and 1×10$^7$ cells were injected into male NOD.SCID mice (12 per group).

Results

Treatment of splenocytes from diabetic NOD mice ex vivo with CD52-Fc resulted in an increase in the diabetes-free survival in NOD.SCID mice into which the treated splenocytes were implanted (FIG. 19). This is yet further evidence of the therapeutic use of soluble CD52 for the treatment of autoimmune diseases such as type 1 diabetes.

Example 19: Human CD52-Fc Suppresses Mouse OT-II Cells

Methods

Mouse ovalbumin (Ova)-specific TCR transgenic CD4 (OT-II) T-cells are a convenient model for testing immune suppression since approximately half of the CD4 T-cells are specific for ovalbumin and T-cell responses are therefore strong and predictable. Splenocytes (1×10$^5$) from 10 week-old female OT-II mice were incubated for 3 days in round bottom 96-well plates in 200 ml RPMI-1640 medium containing 5% FCS and the concentrations indicated in FIG. 20 of ova protein or peptide, or anti-CD3 antibody (clone 2C-11), and recombinant human CD52-Fc or Fc protein. $^3$H-thymidine uptake was measured over the last 16 h of culture. Results are mean±sem of triplicates.

Results

As shown in FIG. 20, CD52-Fc significantly reduced T-cell proliferation in response to stimulation by ova protein or peptide in a dose-dependent manner, providing further evidence of the therapeutic potential of soluble CD52 in treating autoimmune diseases.

Example 20: Seminal Fluid-Derived Soluble CD52 Suppresses Human T-Cell Proliferation Methods CD52 was identified in human semen samples using the following ELISA protocol. Initially, seminal fluid (SF) was centrifuged at 500 g for 5 min to pellet sperm, confirmed by microscopic inspection of the supernatant. Anti-human CD52 antibody (Biolegend #338202) was used as the capture agent (1:100 in PBS; 50 µl/well overnight; 4° C.). Wells were washed 3 times in PBS-0.01% Tween, followed by 3 times in PBS. A solution of 5% BSA/PBS (BSA Sigma A7906) was used to block wells (200 µl/well, 1 hr at room temperature (RT)). Washing was performed as above. Blank wells were included as controls. Semen samples were diluted in 5% BSA/PBS and added at 50 µl/well. Samples were incubated in the wells for 3 hr at RT. Washing was performed as above. For detection, Campath mAb-HRP was used at 1:1000 in 5% BSA/PBS (100 µl/well; 1 h at RT). Washing was performed as above. 3,3',5,5'-Tetramethylbenzidine (TMB) was added and the plates read at 450 nm.

CD52 immunodepletion was performed according to the following protocol. 200 µl Protein G-Sepharose was aliquoted into 2 Eppendorf tubes, followed by washing ×2 with 1 ml PBS, the supernatant being discarded. 5 mg Campath mAb was added to one Eppendorf and 5 mg 'Octagam' (pooled human immunoglobulin) to the other. The tubes were rotated for 1.5 h at 4° C. followed by washing ×3 with 1 ml PBS each. Supernatants were discarded. 500 µl PBS was added, mixed well and samples split evenly into 5× Eppendorf tubes for each sample. Tubes containing Campath and Octagam were spun and supernatants discarded. Semen samples were added to the appropriate tubes (5× different semen samples), i.e. semen 160 µl+160 µl PBS followed by rotation overnight at 4° C. Tubes were spun and supernatants collected for use in T-cell assays at 1:20 (already diluted 1:2 therefore 1:10 into assay).

T-cell proliferation in response to antigen (TT) in PBMCs from healthy donors was measured by CFSE dye dilution (Mannering et al., 2003). CFSE-labelled cells ($2 \times 10^5$/well, 100 µl) were cultured in 96-well round bottom plates in replicates of 6 with medium alone or with TT±CF1D12 anti-CD52 mAb (final concentration 20 µg/ml). The latter was added at either at 0 or 20 hr, the later time to allow initiation of activation of T-cells given that the receptor for soluble CD52, Siglec-10, was shown to be up-regulated by activation (FIG. 12B). Unstained cells were also included and used to set the compensations on the flow cytometer. The cell division index (CDI) was calculated as the ratio of the number of divided $CFSE^{dim}$ $CD4^+$ cells per 20,000 undivided $CFSE^{bright}$ $CD4^+$ cells in the presence of antigen to the number of divided $CFSE^{dim}$ $CD4^+$ cells per 20,000 undivided $CFSE^{bright}$ $CD4^+$ in the absence of antigen.

Results

FIG. 21 illustrates the presence of soluble CD52 in 26 semen samples over serial dilutions. Generally, semen contains high levels of soluble CD52 that titer out over several log dilutions.

As shown in FIG. 22, antigen (TT) alone dramatically increased T-cell proliferation (see 'No semen' bars in FIG. 22). However, this effect was significantly reduced in the presence of semen (see 'TT' for semen samples #1 and #15 in FIG. 22). A single round of immunodepletion of CD52 using the anti-CD52 antibody Campath partially reversed the inhibitory effect of semen (see 'Campath+TT' bars for semen samples #1 and #15 in FIG. 22). No significant reversal was seen with the control IgG immunodepleted samples.

As shown in FIG. 23, antigen (TT) alone dramatically increased T-cell proliferation (see 'No semen' bars in FIG. 23). Addition of the anti-CD52 antibody CF1D12 further increased T-cell proliferation. However, in the presence of semen, T-cell proliferation was dramatically reduced (see 'TT' for semen samples #14, #20 and #22 in FIG. 23). Thus, semen increases unstimulated and decreased antigen-stimulated proliferation. Addition of the anti-CD52 antibody CF1D12 partially reversed the inhibitory effect of semen.

Thus, semen-derived soluble CD52 achieved the same suppressive effect on effector T-cell function (exemplified in this Example by T-cell proliferation) as lymphocyte-derived soluble CD52, demonstrating that alternative carbohydrate moieties can be present on the soluble glycoprotein disclosed herein without diminishing its inhibitory function.

Example 21: CD52-Fc Effects on Monocytes

Methods and Results

THP-1 cells (human acute monocytic leukemia cell line) were grown in RPMI-1640 medium supplemented with 10% FCS, 2 mM glutamine and 50 µM 2-mercaptoethanol Cells were seeded at $2 \times 10^5$/well in IMDM containing 5% pooled, heat-inactivated human serum, 100 mM non-essential amino acids, 2 mM glutamine and 50 µM 2-mercaptoethanol (IP5 medium) at 37° C. under 5% $CO_2$.

Cells were incubated with different doses of CD52-Fc or Fc control in presence of LPS (100 ng/ml) for 24 hr. Medium was collected and the concentration of IL-1ß measured by ELISA. The results of this experiment are summarized in FIG. 24.

In a further experiment, cells were incubated with different doses of CD52-Fc or Fc control in presence of the TLR-2 agonist Pam3CSK (100 ng/ml) for 24 hr. Media were then collected and the concentration of IL-1B measured by ELISA. The results of this experiment are summarized in FIG. 25.

THP-1 cells were also differentiated for 3 hr with 500 nM phorbol-12-myristate-13-acetate (PMA). The cells were then washed and seeded at $2 \times 10^5$/well in IP-5 medium and incubated overnight at 37° C. under 5% $CO_2$. The next morning the medium was changed and cells were incubated with CD52-Fc or Fc control (50 µg/ml) in presence of alum (100 µg/ml) for 16 hour. Medium was collected and the concentration of IL-1B measured by ELISA. The results of this experiment are summarized in FIG. 26.

Bone marrow from 10 week-old C57/B6 mice was differentiated for 7 days in granulocyte-macrophage colony stimulating factor (10 ng/ml) in KDS-RPMI medium-10% FCS. Bone marrow-derived dendritic cells (BMDCs) were collected, washed and seeded at $2 \times 10^4$/well in a 96-well plate. Cells were incubated with 40 µg/ml mouse CD52-Fc or PBS (Control) in presence of LPS (800 ng/ml), CPG (0.8 pM) or *Listeria monocytogenes* ($8 \times 106$/well). In addition, cells were primed for 3 hr with LPS (100 ng/ml) and then stimulated with the known inflammsome agonists, monosodium urate (MSU) (150 µg/ml), alum (150 µg/ml) and nigericin (1 µM). After 24 hr, media were collected and cytokine concentrations measured by multiplex cytokine array assay. The results of this experiment using IL-1β are summarized in FIG. 27. Similar results were obtained for IL-1α, TNF-α, MCP-1, IL-6, IL-9 and IL-12 (data not shown).

Mouse CD52-Fc (250 µg) was incubated with neuraminidase from *Arthrobacter ureafaciens* (2 unit) or reaction buffer (250 mM sodium phosphate, pH 6.0) at 37° C. overnight, and the reaction terminated by heating at 75° C. for 5 minutes. THP-1 cells were incubated with neuraminidase- or reaction buffer-treated mCD52-Fc (final 12.5 µg/ml) in presence of LPS (100 ng/ml) for 24 hr. Media were collected and the concentration of IL-1ß measured by ELISA. The results of this experiment are summarized in FIG. 28.

Mouse CD52-Fc (300 µg) was treated with or without PNGase F under the same conditions, according to the instructions of the manufacturer (BioLabs Inc.). Removal of N-linked oligosaccharide with reduction in the molecular weight of CD52-Fc was confirmed by SDS-PAGE and Coomassie Blue staining. The protein solutions were then desalted by dialysis against pure sterile water. THP-1 cells were seeded at $2 \times 10^5$/well in IP5 medium and incubated with treated CD52-Fc (final 30 µg/ml) or glycosylated CD52-Fc in presence of 100 ng/ml LPS for 24 hr. Media were collected and the concentration of IL-1B measured by ELISA. The results of this experiment are summarized in FIG. 29.

Discussion

In response to a range of inflammatory stimuli, CD52-Fc in a dose-dependent manner suppressed IL-1β secretion by the human THP1 monocyte line and by mouse bone marrow-derived dendritic cells. Furthermore, as shown for T cells, this suppressive effect of CD52-Fc depends on its oligosaccharide moiety because it was abrogated by prior treatment of CD52-Fc with neuraminidase to remove terminal sialic acids or with PNGase-F to remove the N-linked oligosaccharide itself. These findings demonstrate that the suppressive effects of CD52-Fc shown for T cells extend to other cell types that participate in innate immunity and, again similar to T cells, are presumably mediated by a Siglec receptor.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/560,254 filed 15 Nov. 2011 and U.S. 61/705,633 filed 26 Sep. 2012, the entire contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Allan et al. (2007). Int. Immunol. 19: 345-354.
Altschul et al. (1993) J. Mol. Biol. 215: 403410
Armour (2003) Mol. Immunol. 40: 585-93.
Bach et al (1997) J Autoimmun 10:375-386.
Barnden et al. (1998) Immunol. Cells Biol. 76: 34.
Belov et al. (2003) Proteomics 3: 2147-2154.
Bergerot et al. (1994) J. Autoimmun. 7: 655-663.
Collison et al. (2007) Nature 450: 566-569.
Crocker et al. (2007) Nat. Rev. Immunol. 7: 255-266.
Dromey et al. (2011) J. Autoimmunity 36: 47-55.
Every et al. (2006) J. Immunol. 176: 4608-4615.
Fontenot et al. (2003) Nat. Immunol. 4: 330-336.
Gavin et al. (2006) Proc. Natl. Acad. Sci. U.S.A. 103: 6659-6664.
Hale (2001) J. Biol. Regul. Homeost. Agents 15: 386-91.
Harayama (1998) Trends Biotechnol. 16: 76-82.
Hearnden et al. (2012) Ad. Drug Deliver. Rev. 64:16-28.
Herold et al. (2008) Proc. Natl. Acad. Sci. U.S.A. 105: 18507-18512.
Higgins and Sharp (1989) CABIOS. 5: 151-153.
Hogquist et al. (1993) J. Exp. Med. 177: 1469.
Hori et al. (2003) Science 299: 1057-1061.
Hu et al. (2009) Exp. Hematol. 237: 423-434.
Lee (2001) J. Natl. Inst. Monogr. (2001) 29: 41-44.
Lernmark (2001) J Clin Invest 108:1091-1096.
Liu et al. (2006) J Exp Med 203: 1701-1711.
Mannering et al. (2003) J. Immunol. Meth. 283:173-83.
Mittag et al. (2011) J. Immunol. 186: 6207-17.
Miyara et al. (2009) Immunity 30: 899-911.
Munday et al. (2001) Biochem. J. 355: 489-497.
Ngyuen et al. (2006) Proc. Natl. Acad. Sci. 103: 7765-7770.
Roncarolo and Gregori (2008) Eur. J. Immunol. 38: 925-927.
Sakaguchi et al. (2008) Cell 133: 775-787.
Sakaguchi et al. (2009) Int. Immunol. 21: 1105-1111.
Schmidt and Skerra (2007) Nat. Protoc. 2: 1528-35.
Schroter et al (1999) J. Biol. Chem. 274: 29862-29873.
Seddiki et al. (2006) J. Exp. Med. 203: 1693-1700.
Shevach (2006) Immunity 25: 195-201.
Shevach (2009) Immunity 30: 636-645.
Song et al. (2004) Crit. Rev. Ther. Drug Carrier Syst. 21:195-256.
Tang et al. (2004) J. Exp. Med. 199: 1455-1465.
Tisch et al. (1999) J. Immunol. 163: 1178-1187.
Tone et al. (1999) Biochim Biophys. Acta. 1446: 334-340.
Treumann et al. (1995) J. Biol. Chem. 270: 6088-6099.
Vignali et al. (2008) Nat. Rev. Immunol. 8: 523-532.
von Herrath and Harrison (2003) Nat. Rev. Immunol. 3: 223-232.
Xia et al. (1991) Eur. J. Immunol. 21: 1677-1684.

The invention claimed is:

1. A method of treating an autoimmune disorder in a mammalian subject, the method comprising:
   administering to the subject a composition comprising:
   a therapeutically effective amount of soluble CD52 glycoprotein, wherein the soluble CD52 glycoprotein comprises the amino acid sequence GQNDTSQTSSPS (SEQ ID NO: 3), or
   a therapeutically effective amount of a fusion protein comprising a first protein and a second protein, wherein the first protein is a soluble CD52 glycoprotein having the amino acid sequence GQNDTSQTSSPS (SEQ ID NO: 3); and
   a pharmaceutical acceptable carrier.

2. The method of claim 1, wherein the administering is at a mucosal or transdermal site.

3. The method of claim 1, wherein the administering is parenteral.

4. The method of claim 1, wherein the method comprises administering to the subject the composition comprising the therapeutically effective amount of the soluble CD52 glycoprotein and the pharmaceutical acceptable carrier.

5. The method of claim 1, wherein the method comprises administering to the subject the composition comprising the therapeutically effective amount of the fusion protein comprising the first protein and the second protein and the pharmaceutical acceptable carrier.

6. The method of claim 5, wherein the second protein is an Fc polypeptide.

7. A method of suppressing regulatory T cells in a subject having an autoimmune disorder, the method comprising:
   administering to the subject a composition comprising:
   a therapeutically effective amount of soluble CD52 glycoprotein, wherein the soluble CD52 glycoprotein comprises the amino acid sequence GQNDTSQTSSPS (SEQ ID NO: 3), or
   a therapeutically effective amount of a fusion protein comprising a first protein and a second protein, wherein the first protein is a soluble CD52 glycoprotein having the amino acid sequence GQNDTSQTSSPS (SEQ ID NO: 3); and
   a pharmaceutical acceptable carrier.

8. The method of claim 7, wherein the administering is at a mucosal or transdermal site.

9. The method of claim 7, wherein the administering is parenteral.

10. The method of claim 7, wherein the method comprises administering to the subject the composition comprising the therapeutically effective amount of the soluble CD52 glycoprotein and the pharmaceutical acceptable carrier.

11. The method of claim 7, wherein the method comprises administering to the subject the composition comprising the therapeutically effective amount of the fusion protein comprising the first protein and the second protein and the pharmaceutical acceptable carrier.

12. The method of claim 11, wherein the second protein is an Fc polypeptide.

13. The method of claim 7, wherein suppressing regulatory T cells comprises reducing regulatory T cell proliferation.

* * * * *

UNITED STATES PATENT AND TRADEMARK OFFICE
CERTIFICATE OF CORRECTION

PATENT NO. : 10,413,589 B2
APPLICATION NO. : 16/218287
DATED : September 17, 2019
INVENTOR(S) : Esther Bandala Sanchez et al.

Page 1 of 1

It is certified that error appears in the above-identified patent and that said Letters Patent is hereby corrected as shown below:

In the Specification

At Column 11, Line 46:
Delete "IL-113" and replace it with --IL-1β--

At Column 12, Line 11:
Delete "IL-1B" and replace it with --IL-1β--

At Column 44, Line 31:
Delete "Fe" and replace it with --Fc--

Signed and Sealed this
Nineteenth Day of May, 2020

Andrei Iancu
*Director of the United States Patent and Trademark Office*